(12) United States Patent
Soper et al.

(10) Patent No.: US 10,870,881 B2
(45) Date of Patent: *Dec. 22, 2020

(54) BIOMOLECULAR PROCESSING PLATFORM AND USES THEREOF

(71) Applicants: Cornell University, Ithaca, NY (US); Board of Supervisors of Louisiana State University and Agricultural and Mechanical College, Baton Rouge, LA (US); University of North Carolina at Chapel Hill, Chapel Hill, NC (US); Northeastern University, Boston, MA (US)

(72) Inventors: Steven A. Soper, Baton Rouge, LA (US); Francis Barany, New York, NY (US); George Grills, Trumansburg, NY (US); Robin McCarley, Prairieville, LA (US); Collin J. McKinney, Durham, NC (US); Dorel Moldovan, Baton Rouge, LA (US); Michael C. Murphy, Baton Rouge, LA (US); Dimitris Nikitopoulos, Baton Rouge, LA (US); Sunggook Park, Baton Rouge, LA (US); Elizabeth J. Podlaha-Murphy, West Roxbury, MA (US)

(73) Assignees: CORNELL UNIVERSITY, Ithaca, NY (US); UNIVERSITY OF NORTH CAROLINA AT CHAPEL HILL, Chapel Hill, NC (US); NORTHEASTERN UNIVERSITY, Boston, MA (US); BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 189 days.

This patent is subject to a terminal disclaimer.

(21) Appl. No.: 15/898,943

(22) Filed: Feb. 19, 2018

(65) Prior Publication Data

US 2018/0187257 A1 Jul. 5, 2018

Related U.S. Application Data

(63) Continuation of application No. 14/763,972, filed as application No. PCT/US2014/015574 on Feb. 10, 2014, now Pat. No. 9,909,173.

(Continued)

(51) Int. Cl.
*C12Q 1/68* (2018.01)
*C12Q 1/6869* (2018.01)
(Continued)

(52) U.S. Cl.
CPC ...... *C12Q 1/6869* (2013.01); *B01L 3/502761* (2013.01); *G01N 27/4473* (2013.01);
(Continued)

(58) Field of Classification Search
CPC ....... B01L 2200/027; B01L 2200/0663; B01L 2300/0645; B01L 2300/0816; B01L 2300/0896; B01L 2400/0415; B01L 2400/0421; B01L 3/502761; C12Q 1/6869; G01N 27/4473; G01N 27/44791; G01N 33/48721; G01N 33/6803; H01J 49/009

See application file for complete search history.

(56) References Cited

U.S. PATENT DOCUMENTS 6,489,121 B1    12/2002  Skilling
2007/0190546 A1  8/2007  Siddiou et al.
(Continued)

FOREIGN PATENT DOCUMENTS

EP    1047107 A2    10/2000
WO   2005076837 A2   8/2005
WO   2013012440 A2   1/2013

OTHER PUBLICATIONS

Uba et al., "Nanogap Electrical Detection of Single Molecules Translocating Through Nanochannel With Transverse Nanoelectrodes and Funnels Populated With an Array of Nanopillars," 15th International Conference on Miniaturized Systems for Chemistry and Life Sciences, pp. 401-403 (2011).

(Continued)

*Primary Examiner* — Cynthia B Wilder
(74) *Attorney, Agent, or Firm* — Troutman Pepper Hamilton Sanders LLP (Rochester)

(57) ABSTRACT

The present invention relates to a device comprising a biomolecular processor. Each biomolecular processor has one or more bioreactor chambers defined by a solid substrate; a support structure within each bioreactor; a cleaving enzyme immobilized to the support structure and operatively positioned within the bioreactor chamber to cleave monomer or multimer units of a biopolymer molecule operatively engaged by the cleaving enzyme; and one or more time-of-flight channels formed in the solid substrate and fluidically coupled to said one or more bioreactor chambers. Each of the time-of-flight channels have two or more sensors including at least (i) a first sensor contacting the time-of-flight channel proximate to the input end of the channel and (ii) a second sensor contacting the time-of-flight channel proximate to the output end of channel. The present invention further relates to methods of sequencing and identifying biopolymer molecules using the device.

23 Claims, 54 Drawing Sheets

Specification includes a Sequence Listing.

Related U.S. Application Data

(60) Provisional application No. 61/762,671, filed on Feb. 8, 2013.

(51) Int. Cl.
  *G01N 33/68* (2006.01)
  *H01J 49/00* (2006.01)
  *B01L 3/00* (2006.01)
  *G01N 27/447* (2006.01)
  *G01N 33/487* (2006.01)

(52) U.S. Cl.
  CPC . *G01N 27/44791* (2013.01); *G01N 33/48721* (2013.01); *G01N 33/6803* (2013.01); *H01J 49/009* (2013.01); *B01L 2200/027* (2013.01); *B01L 2200/0663* (2013.01); *B01L 2300/0645* (2013.01); *B01L 2300/0816* (2013.01); *B01L 2300/0896* (2013.01); *B01L 2400/0415* (2013.01); *B01L 2400/0421* (2013.01)

(56) References Cited

U.S. PATENT DOCUMENTS

| | | |
|---|---|---|
| 2009/0023146 A1 | 1/2009 | Harnack et al. |
| 2012/0129716 A1 | 5/2012 | Chee et al. |
| 2012/0305760 A1 | 12/2012 | Blick |

OTHER PUBLICATIONS

Clarke et al., "Continuous Base Identification for Single-Molecule Nanopore DNA Sequencing," Nature Nanotechnology 4:265-270 (2009).

Langecker et al., "Electrophoretic Time-of-Flight Measurements of Single DNA Molecules with Two Stacked Nanapores," Nano Lett. 11:5002-5007 (2011).

Novak et al., "Distinguishing Single DNA Nucleotides Based on Their Times of Flight Through Nanoslits: A Molecular Dynamics Simulation Study," J. Phys. Chem. B 117:3271-3279 (2013).

International Search Report and Written Opinion for corresponding application No. PCT/US2014/015574 dated May 14, 2014.

First Office Action CN201480008025.4 dated Aug. 9, 2016.

Extended Search Report and Opinion for EP14749210.2 dated Feb. 8, 2017.

NIH Project Information 1R21HG006278-01, "Polymer Based Modular Systems with Nanosensors for DNA/RNA Sequencing".

Lee et al., "Development of an Automated Digestion and Droplet Deposition Microfluidic Chip for MALDI-TOF MS," J Am Soc Mass Spectrom 19(7):964-72 (2008).

Japanese Patent Application Kokai Publication No. (JP-A) 2007-044043 (English abstract).

Notice of Reasons for Rejection in JP 2015-557162 dated Dec. 28, 2017 (English translation).

Canadian Office Action for Canadian Patent Application No. 2,896,674 (dated Dec. 18, 2019).

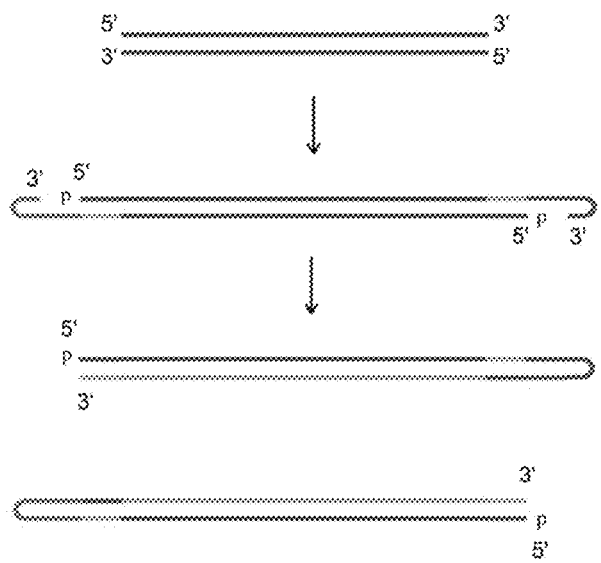

1. (Only one genomic double stranded DNA fragment is shown.)

2. Ligation of universal adaptors to each DNA fragment. Adaptors contain an optional strand ID, and a short hairpin region.

3. The 3' hairpinned ends are extended using a polymerase with strand displacement activity. The resultant double-stranded DNAs are ideally suited for X-TOF sequencing. The sequenced strand contains strand ID on both ends, allowing unique verification of their origin. Further, since the original genomic strand is sequenced, all base modifications are preserved.

Figure 8A 1. (Only one genomic double stranded DNA fragment is shown.) Extend and tail universal adaptors.

2. Ligation of universal adaptors to each DNA fragment. Adaptors contain an optional strand ID, and a short hairpin region.

3. The 3' hairpinned ends are extended using a polymerase with strand displacement activity. The resultant double-stranded DNAs are ideally suited for X-TOF sequencing. The sequenced strand contains strand ID on both ends, allowing unique verification of their origin. Further, since the original genomic strand is sequenced, all base modifications are preserved.

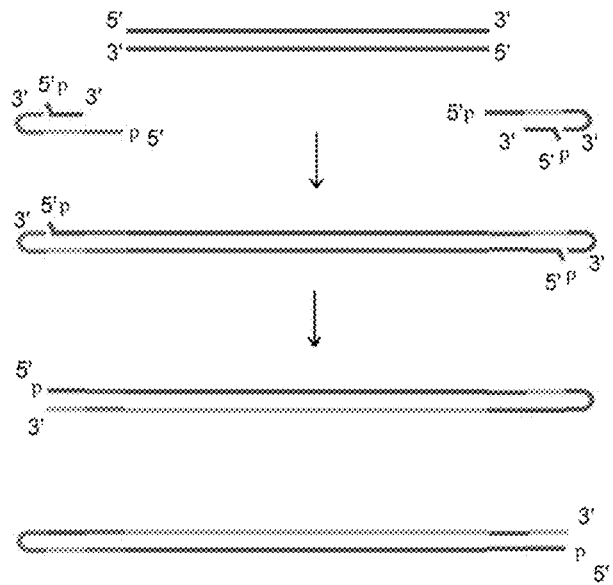

Figure 8B

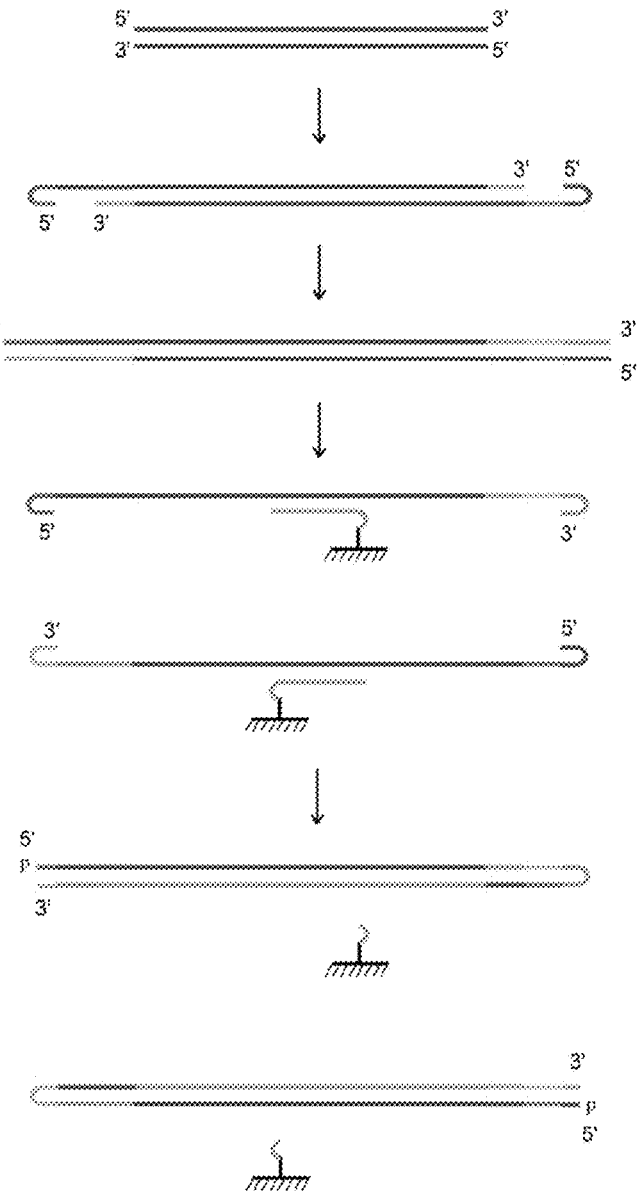

1. (Only the target double stranded DNA of interest for enrichment is shown.)

2. Ligation of universal adaptors to each DNA fragment. Adaptors contain an optional patient ID, strand ID, and a short hairpin region.

3. The 3' linker ends are extended through the hairpin using a polymerase lacking 5'-3' activity.

4. The double stranded DNA is denatured and rendered into single stranded DNA. Both the upper and lower target strands are captured by hybridization to complementary strands immobilized to a solid support. The complementary strands are spatially seperated so that neither they nor the target strands will rehybridize to each other.

5. The 3' hairpinned ends are extended using a polymerase with 5'-3' exonuclease activity. This releases double-stranded target DNA from the solid support and also liberates a 5' phosphate end, ideally suited for X-TOF sequencing. The sequenced strand contains patient ID and strand ID on both ends, allowing unique verification of their origin. Further, since the original genomic strand is sequenced, all base modifications are preserved.

Figure 9

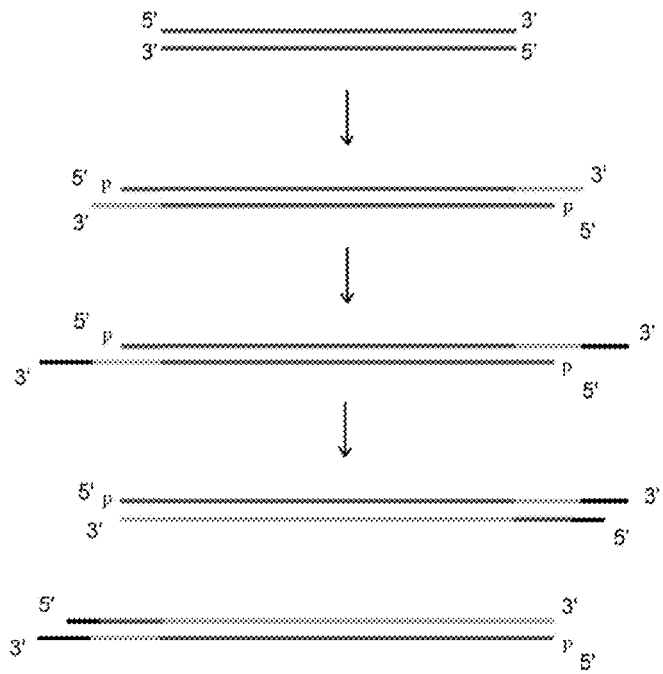

1. (Only one genomic double stranded DNA fragment is shown.)

2. Ligation of universal adaptors to each DNA fragment. Adaptors contain an optional strand ID.

3. The 3' linker ends are tailed using terminal transferase.

4. Primers are hybridized to the 3' ends of the tailed adaptor strands, and primers are extended using a polymerase. This generates double-stranded DNAs ideally suited for X-TOF sequencing. The sequenced strand contains strand ID on both ends, allowing unique verification of their origin. Further, since the original genomic strand is sequenced, all base modifications are preserved.

Figure 10

1. (Only the target double stranded
   DNA of interest for enrichment is shown.)

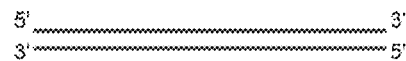

2. Ligation of universal adaptors to each
   DNA fragment. Adaptors contain an
   optional patient ID and strand ID.

3. The 3' linker ends are extended with
   polymerase and tailed using
   terminal transferase.

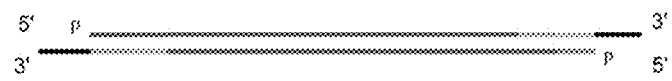

4. The double stranded DNA is denatured
   and rendered into single stranded DNA.
   Both the upper and lower target strands are
   captured by hybridization to complementary
   strands immobilized to a solid support. The
   complementary strands are spatially
   seperated so that neither they nor the target
   strands will rehybridize to each other.

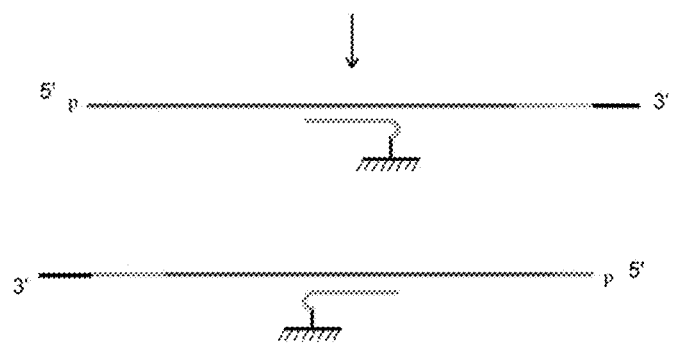

5. Primers are hybridized to the 3' ends of
   the target single strands, and primers
   are extended using a polymerase. This
   generates double-stranded target DNA,
   ideally suited for X-TOF sequencing. The
   sequenced strand contains patient ID and
   strand ID on both ends, allowing unique
   verification of their origin. Further, since
   the original genomic strand is sequenced,
   all base modifications are preserved.

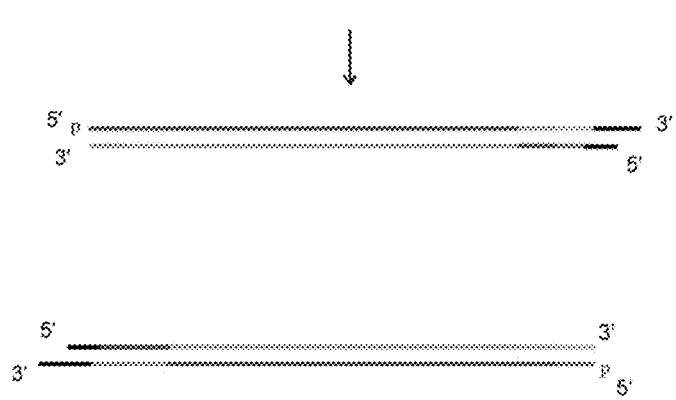

BIOMOLECULAR PROCESSING PLATFORM AND USES THEREOF

This application is a continuation of U.S. patent application Ser. No. 14/763,972, filed Jul. 28, 2015, now U.S. Pat. No. 9,909,173, issued on Mar. 6, 2018, which is a national stage application under 35 U.S.C. § 371 of PCT Application No. PCT/US2014/015574, filed Feb. 10, 2014, which claims the benefit of U.S. Provisional Patent Application Ser. No. 61/762,671, filed Feb. 8, 2013, which is hereby incorporated by reference in its entirety.

This invention was made with government support under R21-HG006278-01 awarded by National Institutes of Health, EPS-0346411, and EPS-0701491 awarded by National Science Foundation. The government has certain rights in the invention.

FIELD OF THE INVENTION

The present invention relates to a device and methods suitable for nucleic acid sequencing and protein/polypeptide identification.

BACKGROUND OF THE INVENTION

The benefits of the $1,000 genome have been well documented in the literature (Kaiser, J., "DNA Sequencing—A Plan to Capture Human Diversity in 1000 Genomes," *Science* 319:395-395 (2008); Kuehn, B. M., "1000 Genomes Project Promises Closer Look at Variation in Human Genome," *JAMA* 300:2715-2715 (2008); Mardis, E., "Anticipating the $1,000 Genome," *Genome Biol.* 7:112 (2006); Metzker, M. L., "Emerging Technologies in DNA Sequencing," *Genome Res.* 15:1767-1776 (2005); Schloss, J., "How to Get Genomes at One Ten-Thousandth the Cost," *Nature Biotechnol.* 26:1113-1115 (2008)). Some of the important consequences include; (i) personalized medicine that could assist in more effective disease prevention, improve diagnosis and prognosis to match the appropriate therapy with the specific patient through genome-wide evaluation of sequence variations; (ii) understanding genome-wide complexity; (iii) designing new therapeutics; and (iv) developing a de facto standard for in vitro diagnostics (IVD) irrespective of sequence variation type.

There are a plethora of different genetic variations that serve as effective biomarkers for a variety of diseases, such as sporadic mutations, inherited mutations, single nucleotide polymorphisms (SNPs), methylation patterns (epigenetics), gene expression, copy number variation, microsatellite instability, etc. Unfortunately, all of these structural modifications require a unique assay format and as such, are difficult to implement in the clinic due to the specialized equipment and expertise required to carry out each molecular assay (Thomas et al., "Biomedical Microelectromechanical Systems (BioMEMS) Using Electrophoresis for the Analysis of Genetic Mutations," *Molecular Review Diagnostics* 2:429-447 (2002)). A "standard" assay format that can uncover the presence/absence of all sequence variations using a single instrument with little operator expertise will expand the full utility of IVD. In many cases, extensive resequencing of selected exons in the genome can provide the necessary clinical information with the required sensitivity irrespective of the type of sequence variation.

Advances in DNA sequencing hold the promise to standardize and develop non-invasive molecular diagnosis to improve prenatal care, transplantation efficacy, cancer and other disease detection and individualized treatment. Currently, patients with predisposing or early disease are not identified, and those with disease are not given the best treatment—all because of failures at the diagnostic level. Consequently, there is an urgent need to develop automated ultra-fast sequencing platforms that may be used in the clinical laboratory. Such low-cost bench-top machines are needed to accelerate the discovery, validation and clinical use of molecular markers.

For example, in the cancer field, there is a need to develop such technology for early detection, guiding therapy, and monitoring for recurrence—all from a blood sample. This includes the need to develop (i) high sensitivity detection of promoter hypermethylation and hypomethylation (when present at 1% to 0.01% of cell-free DNA), (ii) high sensitivity detection of common and uncommon mutations in known genes (when present at 1% to 0.01% of cell-free DNA), (iii) accurate quantification of tumor-specific mRNA and miRNA isolated from tumor-derived exosomes or RISC complex in blood, (iv) accurate quantification of tumor-specific copy changes in DNA isolated from circulating tumor cells, (v) accurate quantification of mutations, promoter hypermethylation and hypomethylation in DNA isolated from circulating tumor cells. All of the above cases (except quantification of tumor-specific copy changes in DNA isolated from circulating tumor cells) require focusing the sequencing on targeted genes or regions of the genome. Further, determination of the sequence information or methylation status from both strands of the original fragment provides critically needed confirmation of rare events.

In the prenatal care field, there is an urgent need to develop non-invasive assays for, common aneuploidies, such as trisomy 21, 18, or 13, small deletions, such as those arising from deletions in the Duchenne muscular dystrophy (DMD) gene, other small copy number anomalies, such as those responsible for autism, balanced translocations to determine potential clinical manifestations, methylation changes, which may result in diseases associated with imprinting, such as Angelman's syndrome or Prader-Willi syndrome, triplet repeat changes, responsible for diseases such as Huntington's disease, point mutations, such as those in the CFTR gene responsible for cystic fibrosis.

Single molecule sequencing (SMS) provides some unique attributes not available with ensemble-based strategies, such as those based on PCR, in terms of attaining the ambitious mandates set forth by the $1,000 genome project. For example, SMS (i) streamlines the sample processing pipeline to reduce the finished base sequencing cost (Bayley, H., "Sequencing Single Molecules of DNA," *Curr. Opin. Chem. Biol.* 10:628-637 (2006)); (ii) eliminates the need for amplification and its associated biases as well as the reagents and the need for designing primers appropriate for difficult regions of the genome (i.e., highly repetitive regions); (iii) provides the ability to look directly for methylation sites, rare mutations and other sequence variations with high identification efficiency; (iv) provides high sensitivity for monitoring copy number variations; and (v) generates long reads that can reduce assembly demands, and sequence through high repeat regions.

One type of SMS approach involved synthesis of a polymerase-generated complementary DNA strand composed of fluorescently-labeled deoxynucleotides (Davis et al., "Rapid DNA Sequencing Based Upon Single Molecule Detection," *Genetic Analysis—Biomolecular Engineering* 8:1-7 (1991); Goodwin et al., "Application of Single Molecule Detection to DNA Sequencing," *Nucleosides & Nucleotides* 16:543-550 (1997); Goodwin et al., "DNA Sequencing by Single Molecule Detection," *Prog. Biophys.*

Mol. Biol. 65:SMI02-SMI02 (1996)). The complementary DNA strand is anchored to a microbead using a streptavidin: biotin linkage. Optical trapping is used to suspend the bead:DNA complex in a flow stream filled with a highly processive exonuclease, which sequentially clips the terminal mononucleotides (dNMPs) sending them through an excitation laser beam that produce fluorescent photon bursts with the color providing the mechanism for identification. While conceptually simple and, in spite of the demonstration of one-color sequencing (Werner et al., "Progress Towards Single-Molecule DNA Sequencing: A One Color Demonstration," *J. Biotechnol.* 102:1-14 (2003)), several challenges with this approach have been encountered, including the inability to build a complement using exclusively dye-modified dNTPs, diffusional misordering resulting from scaling issues, and impurity fluorescence reducing the signal-to-noise ratio during single-molecule detection (Demas et al., "Fluorescence Detection in Hydrodynamically Focused Sample Streams: Reduction of Diffusional Defocusing by Association of Analyte With High-Molecular Weight Species," *Appl. Spectroscopy* 52:755-762 (1998) and Goodwin et al., "DNA Sequencing by Single Molecule Detection," *Prog. Biophys. Mol. Biol.* 65:SMI02-SMI02 (1996)).

Recently, alternative fluorescence-based SMS strategies have been proposed that follow incorporation events of fluorescently-labeled dNTPs by polymerases and use zero-mode waveguides monitoring dNTPs labeled with spectrally distinct dyes phospholinked to the dNTPs (Eid et al., "Real-Time DNA Sequencing From Single Polymerase Molecules," *Science* 323:133-138 (2009)). Another approach uses single DNA molecules arrayed onto a solid support with each incorporation event generating a fluorescence burst of photons (Braslavsky et al., "Sequence Information Can be Obtained From Single DNA Molecules," *Proc. Nat'l. Acad. Sci., U.S.A.* 100:3660-3964 (2003)). While these are excellent examples of securing sequence information directly from single molecules, they do provide some common challenges, such as the need for fluorescence substrates, the large amount of spectral overlap between molecular systems generating cross-talk or cross-excitation and the need for extensive optical hardware to read the resulting signatures.

To circumvent the requirement for fluorescence-based reads from SMS formats, nanopore technologies have been proposed to allow for the direct read of DNA sequence data from electrical signatures of mononucleotides comprising the target DNA, obviating the need for fluorescence (Akeson et al., "Microsecond Time-Scale Discrimination Among Polycytidylic Acid, Polyadenylic Acid, and Polyuridylic Acid as Homopolymers or as Segments Within Single RNA Molecules," *Biophys. J.* 77:3227-3233 (1999); Deamer & Branton, "Characterization of Nucleic Acids by Nanopore Analysis," *Acc. Chem. Res.* 35:817-825 (2002); Meller & Branton, "Single Molecule Measurements of DNA Transport Through a Nanopore," *Electrophoresis* 23:2583-2591 (2002); Meller et al., "Voltage-Driven DNA Translocations Through a Nanopore," *Phys. Rev. Lett.* 86:3435-3438 (2001); and Meller et al., "Rapid Nanopore Discrimination Between Single Polynucleotide Molecules," *Proc. Nat'l. Acad. Sci. U.S.A.* 97:1079-1084 (2000)). In most studies, the nanopore is α-hemolysin, which is a proteinaceous membrane channel produced by the bacterium, *S. aureus*. From the application standpoint, the use of this pore has several limitations: (1) its mechanical and chemical stability are in many cases, inadequate; (2) it has a fixed pore size that allows transduction of only selected types of molecules; and (3) the ability to manufacture high-density arrays of such nanopores can be problematic. These α-hemolysin limitations have led to the use of synthetic nanopores (Rhee & Burns, "Nanopore Sequencing Technology: Research Trends and Applications," *Trends Biotechnol.* 24:580-586 (2006) and Storm et al., "Fabrication of Solid-State Nanopores With Single-Nanometre Precision," *Nat. Mater.* 2:537-541 (2003)) that can be fabricated with 1-50 nm sizes in polymer or silicon nitride membranes using electron or ion beams. The attractive feature of the synthetic nanopores is the ability to adopt different readout modalities, such as the use of transverse electrodes decorating the synthetic pore to monitor perturbations in the tunneling current or conductance changes (Lagerqvist et al., "Fast DNA Sequencing Via Transverse Electronic Transport," *Nano Lett.* 6:779-782 (2006); Lagerqvist et al., "Influence of the Environment and Probes on Rapid DNA Sequencing Via Transverse Electronic Transport," *Biophys. J.* 93:2384-2390 (2007); Zikic et al., "Characterization of the Tunneling Conductance Across DNA Bases," *Phys. Rev. E* 74(1 Pt 1):011919 (2006); and Zwolak & Di Ventra, "Colloquium: Physical Approaches to DNA Sequencing and Detection," *Rev. Modern Physics* 80:141-165 (2008)).

In principle, structural information of DNA, whether using a natural or synthetic nanopore, is obtained by deducing the identity of a nucleotide from the blockage current magnitude as an intact DNA molecule is moved through the pore. The advantages of this DNA sequencing approach include; (1) the ability to sequence large DNA fragments (≥50 kbp); (2) does not require the use of amplification or sub-cloning techniques; (3) does not require the use of deoxynucleotides or dideoxynucleotides that are fluorescently labeled; (4) small input DNA sample sizes are required, on the order of $1 \times 10^8$ copies for whole genome sequencing and; (5) the rate at which DNA sequence information can be obtained could provide near real-time readout. Unfortunately, a working demonstration of DNA sequencing directly from a nanopore has yet to be demonstrated.

There has been several reviews focused on the potential of nanopore technology for DNA sequencing, and, as these reviews point out, a number of challenges exist to realize this exciting new platform and its potential for DNA sequencing (Branton et al., "The Potential and Challenges of Nanopore Sequencing," *Nat. Biotechnol.* 26:1146-1153 (2008) and Zwolak & Di Ventra, "Colloquium: Physical Approaches to DNA Sequencing and Detection," *Rev. Modern Physics* 80:141-165 (2008)). First, the translocation times through the pore are fairly high (1-20 µs per nucleotide) requiring the bandwidth of the readout electronics to function in the MHz range. Secondly, the readout resolution requires a pore thickness equal to or less than the single base spacing of DNA molecules, ~0.34 nm. Because the thickness of both synthetic and α-hemolysin pores is much larger (5-15 nm) than this spacing, multiple bases simultaneously reside within the pore. Even if nanopores could be fabricated with this prerequisite thickness, the effective electric field read region would extend approximately 1 pore diameter unit on either side of the pore (Liu et al., "The Effect of Translocating Cylindrical Particles on the Ionic Current Through a Nanopore," *Biophys. J.* 92:1164-1177 (2007)). Third, the production of arrays of nanopores must be done in a high production mode reproducibly with the prerequisite size dimensions and at low-cost to accommodate the intended application. Fourth, high quality genomic DNA must be extracted from a diverse array of samples (blood, tissue, bone marrow, urine, saliva, etc) and then processed to produce DNA fragments (~50 kbp), which are used as the input for sequencing. The sample preparation and sequencing steps should be integrated into a single platform and operate in a basic turn-key mode to allow a broad user base.

Readout resolution limitations can be mitigated if nucleotides are physically separated from each other while maintaining their original order following clipping from the DNA, for example through the use of an exonuclease enzyme (Davis et al., "Rapid DNA Sequencing Based on Single Molecule Detection," In *Los Alamos Science* (1992)). This has been demonstrated to be feasible using a highly processive exonuclease enzyme, which sequentially clips individual nucleotides from an intact DNA fragment and directing these bases through an α-hemolysin nanopore fitted with a cyclodextrin collar (Wu et al., "Protein Nanopores With Covalently Attached Molecular Adapters," *J. Am. Chem. Soc.* 129:16142-16148 (2007) and Clarke et al., "Continuous Base Identification for Single-Molecule Nanopore DNA Sequencing," *Nature Nanotechnol.* 4:265-270 (2009)). Unfortunately, the single base identification efficiency using blockage currents is 93-98% (Astier et al., "Toward Single Molecule Sequencing: Direct Identification of Ribonucleoside and Deoxyribonucleoside 5'-Monophosphates by Using an Engineered Protein Nanopore Equipped With a Molecular Adaptor," *J Am. Chem. Soc.* 128:1705-1710 (2006)), and therefore, errors in sequencing using blockage currents alone do not generate the necessary sequencing accuracy required to identify mutational sites, for example. Also, salt conditions required for optimum exonuclease activity could not be matched to conditions required for high accuracy base identification and thus, the identification efficiency ranged from 90% to 99%. Therefore, additional base identification strategies must be considered.

The present invention overcomes these and other deficiencies in the art.

SUMMARY OF THE INVENTION

A first aspect of the present invention is directed to a device comprising a biomolecular processor. Each biomolecular processor comprises one or more bioreactor chambers defined by a solid substrate, and a support structure within each bioreactor chamber that is attached to the solid substrate. The biomolecular processor also has a cleaving enzyme immobilized to the support structure and operatively positioned within said bioreactor chamber to cleave monomer or multimer units of a biopolymer molecule operatively engaged by the cleaving enzyme. The biomolecular processor also has one or more time-of-flight channels formed in the solid substrate and fluidically coupled to the one or more bioreactor chambers. Each of the one or more time-of-flight channels has an input end and an output end, where each of the one or more time-of-flight channels has two or more sensors including at least (i) a first sensor contacting the one or more time-of-flight channels proximate to the input end of the one or more time-of-flight channels and (ii) a second sensor contacting the one or more time-of-flight channels proximate to the output end of the one or more time-of-flight channels.

Other aspects of the present invention relate to methods for nucleic acid sequencing and protein or polypeptide identification using the device of the present invention.

Another aspect of the present invention is directed to a method for identifying one or more of a plurality of nucleic acid molecules in a sample. This method involves providing a sample containing one or more nucleic acid molecules each hybridized to its respective complementary nucleic acid molecule, wherein each of the one or more nucleic acid molecules and its hybridized complement thereof comprise a target specific portion and a singled stranded 3' adapter portion suitable for hairpin formation. The sample is subjected to conditions effective for the 3' adapter portions of the one or more nucleic acid molecules and complements thereof to form a hairpin. The method further involves providing a polymerase and blending the one or more 3' hairpinned nucleic acid molecules and complements thereof with the polymerase to form an extension mixture. The one or more nucleic acid molecules and complements thereof are extended from their respective 3' hairpinned regions to form one or more full-length hairpinned nucleic acid molecules. The method further involves sequencing at least a portion of the one or more full-length hairpinned nucleic acid molecules to identify one or more nucleic acid molecules in the sample.

Another aspect of the present invention is directed to a method for identifying one or more of a plurality of nucleic acid molecules in a sample that involves immobilization on a solid support to achieve target specific enrichment of one or more desired nucleic acid molecules. This method involves providing a sample containing one or more nucleic acid molecules each hybridized to its respective complementary nucleic acid molecule, wherein each of the one or more nucleic acid molecules and its hybridized complement thereof comprise a target specific portion, a 5' adapter portion, and a 3' adapter portion, wherein each of the 5' and 3' adapter portions are suitable for hairpin formation. The method further involves denaturing the one or more nucleic acid molecules from their complements thereof to form a collection of one or more single-stranded nucleic acid molecules and complements thereof, wherein the hairpin sequences of the 5' and 3' adapter portions of each of the one or more single stranded nucleic acid molecules and complements thereof form hairpins. A solid support is provided that comprises a plurality of immobilized capture oligonucleotide probes, said capture oligonucleotide probes comprising a nucleotide sequence that is complementary to a region of the target specific portion of the one or more nucleic acid molecules or complements thereof. The one or more denatured single stranded nucleic acid molecules and complements thereof are hybridized to their complementary immobilized capture oligonucleotides on the solid support. This method further involves providing a polymerase and contacting the polymerase with the solid support containing the one or more hybridized nucleic acid molecules and complements thereof. The one or more nucleic acid molecules and complements thereof are extended from their respective 3' hairpinned regions to form one or more full-length hairpinned target nucleic acid molecules, thereby causing the one or more nucleic acid molecule to be released from the capture oligonucleotides and from the solid support. At least a portion of the one or more nucleic acid molecules is sequenced to identify the one or more nucleic acid molecules in the sample.

Another aspect of the present invention is directed to a method a method for identifying one or more of a plurality of nucleic acid molecules in a sample. This method involves providing a sample containing one or more nucleic acid molecules each hybridized to its respective complementary nucleic acid molecule, wherein each of the one or more nucleic acid molecules and its hybridized complement thereof comprise a target specific portion, a 5' adapter portion, and a 3' adapter portion comprising a single stranded homopolymer repeat sequence. The method further involves denaturing the one or more nucleic acid molecules from its complement thereof to form a collection of single-stranded nucleic acid molecules and complements thereof. A plurality of oligonucleotide primers that are complementary to the 3' ends of the one or more nucleic acid molecules or complements thereof and a polymerase are provided, and the one or more nucleic acid molecules and complements thereof are blended with the polymerase and primers to form an extension mixture. The method further involves hybridizing the oligonucleotide primers to their complementary 3' ends of the one or more nucleic acid molecule and complements thereof, and extending the hybridized primers to form full-length double stranded nucleic acid molecules. At least a portion of the one or more full-length double stranded nucleic acid molecules is sequenced to identify the one or more nucleic acid molecules in the sample.

The present invention relates to a biopolymer sequencing platform, referred to herein as a biomolecular processor, that can substantially reduce the cost, labor and time associated with acquiring sequencing information using a fully automated platform. The platform uses nano-scale sensors that identify monomer and multimer units of a biopolymer molecule, based on their characteristic flight-time through a 2-dimensional (2D) time-of-flight channel fabricated in a moldable solid support using low-cost micro- and nano-replication techniques. The monomer and multimer units are generated from an intact biopolymer, e.g., nucleic acid molecule or protein, using a cleavage enzyme, which is covalently anchored to a support structure contained within a bioreactor chamber of the biomolecular processor. The cleaved monomer or multimer units are fed into a time-of-flight channel, where the identity of the monomer or multimer is deduced from a molecular-dependent flight-time through the time-of-flight channel. The flight-time is transduced using at least two pairs of sensors poised at each end of the channel with the signal resulting from perturbations in an electrical response induced by the monomer or multimer units.

The approach proposed herein directly addresses the major challenges associated with nanopore-based technologies for DNA sequence determinations as noted by Branton et al., "The Potential and Challenges of Nanopore Sequencing," *Nat. Biotechnol.* 26:1146-1153 (2008), which is hereby incorporated by reference in its entirety. Firstly, the bandwidth limitations associated with nanopore sequencing requiring reductions in the translocation rate is negated due to the fact that individual bases are spaced ($\Delta t$) by a length determined by the enzyme clipping rate and the applied electric field as well as the electrophoretic mobility of the monomer. For example, using a $\lambda$-exonuclease clipping rate of 1,000 nucleotides $s^{-1}$ (Matsuura et al., "Real Time Observation of a Single DNA Digestion by Lambda Exonulease Under a Fluorescence Microscope Field," *Nucleic Acids Res.* 29:e79 (2001), which is hereby incorporated by reference in its entirety), and a linear velocity of 0.1 mm $s^{-1}$, the nucleotide spacing would be 100 nm. Multiple occupancy of nucleotides within the flight tube nanochannel is not an issue, because the start and stop times are measured by the at least two-electrode pairs poised within the flight tube. Secondly, the single base resolution requirement for nanopores to be <0.34 nm in thickness is not necessary because of the exonuclease-imposed spacing of the dNMPs and the fact that blockage currents are not being used to identify the nucleotide base. Indeed, the identity of the nucleotides is based on well-established chromatographic or electrophorectic properties of these entities (Czamecka et al., "Application of Solid Phase Extraction and High-Performance Liquid Chromatography to Qualitative and Quantative Analysis of Nucleotides and Nucleosides in Human Cerebrospinal Fluid," *J. Chromatogr. B* 822:85-90 (2005), which is hereby incorporated by reference in its entirety). In addition, the use of transconductance or tunneling currents and the potential issues with molecular orientation effects on the transduced signal is not present in the present invention (Zikic et al., "Characterization of the Tunneling Conductance Across DNA Bases," *Phys. Rev. E* 74(1 Pt 1):011919 (2006), which is hereby incorporated by reference in its entirety). Because the fluidic elements, both micro- and nano-, are produced using established replication technologies in moldable materials, they can be produced at low-cost and at high production rates. In addition, the nano-scale electrodes will be generated using templating methods in porous templates, or other methods described herein, to allow for high-scale production of the sensing elements. Fourth, the biomolecular processor of the present invention can be interfaced to micro-scale modules as described herein to generate autonomous systems for processing the sample prior to submission for sequence analysis. For example, the DNA can be selected from target cells, purified and sheared prior to sequencing in a fully automated fashion. In addition, the material property flexibility afforded by the vast array of moldable materials as well as the modular approach adopted, will allow the building of these systems with selection of the substrate material optimized for the application. Finally, the low-cost production of these modules and their straight-forward assembly as well as the high functionality of the assembled system will provide low-cost platforms and their automation capabilities will produce a platform for resequencing or de novo sequencing directly within a clinical setting or a small discovery-based laboratory.

BRIEF DESCRIPTION OF THE DRAWINGS

FIG. 3A is a SEM image of a v-shaped feeder channel inlet 28 containing an array of micro- and/or nanopillars. FIG. 3B is an SEM image of the feeder channel 20 containing an entropic trap 30 and coupled to the bioreactor chamber 14. FIG. 3C is an SEM image of the bioreactor chamber 14 containing the solid support 16 with the immobilized cleaving enzyme 36. The bioreactor chamber is fluidically coupled to the feeder channel 20 and the time-of-flight channel 24. FIG. 3D shows the time-of-flight channel 24 with a first 32 and second 34 pair of nanosensing electrodes located within the channel 24. As shown the nanosensing electrodes are each connected to microcontact pads 40 that couple the nanosensing electrodes to external electronic components of the device.

FIG. 4A shows SEM images of various inlets, including a groove inlet, V-shaped micro/sub-micron groove inlet, a pillar inlet with an array of micro/nanopillars, and a funnel inlet. FIG. 4B is a graph showing the enhancement of DNA capture using the various inlet designs of FIG. 4A as compared to an abrupt microfluidic-to-nanochannel interface ("original").

FIG. 6A is a top-view of a biomolecular processor 10 comprising the feeder channel 20, bioreactor chamber 14, and time-of-flight channel 24 containing a first 32, second 34, and third 33 pair of nanosensing electrodes. FIG. 6B is a perspective view showing a mononucleotide 46 entering and exiting a time-of-flight channel 24 containing three pairs of nanosensing electrodes 32, 33, 34.

FIGS. 8A-8B are schematics showing alternative methods of preparing both strands of double-stranded genomic DNA for sequence analysis in accordance with the methods of the present invention.

FIG. 9 is a schematic overview of a method for enriching a sample for target genomic DNA and preparing both strands of the enriched double stranded DNA for sequence analysis in accordance with the methods of the present invention.

FIG. 10 is a schematic showing a method of preparing both strands of double-stranded genomic DNA for sequence analysis in accordance with the methods of the present invention.

FIG. 11 is a schematic overview of a method for enriching a sample for target genomic DNA and preparing both strands of the enriched double stranded DNA for sequence analysis in accordance with the methods of the present invention.

FIG. 30A is a schematic of the assembly process. FIG. 30B is a schematic of the pressure heater used in the assembly process. FIG. 30C are images of the bonded coverplate.

FIG. 33A shows protonated 3' dAMP; FIG. 33B shows nonprotonated 3' dGMP; FIG. 33C protonated 5' dCMP; and FIG. 33D shows nonprotonated 5' dTMP. The differences between the partial charges on the encircled atoms in the structure of FIG. 33B and the corresponding atoms in the structure of FIG. 33A were applied to the structure of FIG. 33C to get the partial charges on the encircled atoms in the structure of FIG. 33D. The only structural difference between the encircled atoms in the structures of FIGS. 33B and 33D is at the C3' and C5' atoms. Structures like FIG. 33D with the four different nucleobases were used in the simulations. The identity of the nucleobase does not affect the partial charges on the phosphate group. The axes labeled axis 1 on the nucleobases were used in the analysis of dNMP adsorption and desorption to the slit walls and are discussed in.

FIG. 34A shows the simulation system containing water, sodium chloride, and a dNMP in a nanoslit. Gray spheres represent wall atoms, green represents chloride, tan represents phosphorus, yellow represents sodium, red represents non-water oxygen, white represents non-water hydrogen, cyan represents non-wall carbon, blue represents nitrogen, and purple represents water molecules. Some of the wall atoms are not shown for clarity. There are periodic boundary conditions in the x and y directions.

FIG. 34B shows two dNMPs (only polar hydrogens are shown). Single ring pyrimidine (C, T) and two ring purine (A, G) nucleobases are attached to the sugar-phosphate backbone. λ-exonucleases can digest one strand of a double-stranded DNA one nucleotide at a time starting from the 5' end and leaving the phosphate on the 5' end of each released nucleotide.

FIG. 40A depicts dAMP. FIG. 40B depicts dGMP.

FIG. 40C depicts dCMP. FIG. 40D depicts dTMP.

FIGS. 46A and 46B are Atomic Force Microscopy (AFM) scans of PMMA surfaces exposed to λ-Exo alone (FIG. 46A) or λ-Exo in combination with 3-(3-dimethylaminopropyl) carbodiimide (EDC)/N-hydroxysuccinimide (NHS) coupling reagents (FIG. 46B). FIG. 46C is a histogram showing the size distribution of immobilized λExo enzymes across the polymer surface.

FIG. 50A shows EOF in a native unmodified PMMA nanochannel (♦), and a PMMA nanochannel treated with an $O_2$ plasma (▲). FIG. 50B shows EOF in a native unmodified PMMA nanochannel (•), and a PMMA nanochannel that was plasma oxidized and treated with ethylene diamine in the presence of EDC/NHS coupling reagents (■).

FIG. 51A is a histogram showing for the single entity electrophoretic driven translocation times through PMMA nanochannels performed at an electric field strength of 4000 V/cm. Comparison of this data to that performed at lower field strengths indicated that the spread in the translocation time was inversely related field strength due to reduced dispersion effects at higher electric fields. FIG. 51B is an image (3D-plot) of a single silver nanoparticle (Ag-NP) placed in a PMMA nanochannel in the absence of an electric field. FIG. 51C is a graph showing the electrophoretic mobility and the plate numbers (measure of width of histogram shown in FIG. 51A) for the electrically driven translocation of the single entities in the PMMA nanochannel.

FIGS. 52A and 52B show ionic current spikes generated by translocation of short DNA molecules (~<5 μm). FIG. 52C is a schematic showing the short DNA molecule translocating through the nanopillar array and nanochannel of a nanofluidic device. FIGS. 52D-52F and 52G-52I show the ionic current spikes generated by translocation of longer DNAs (not full length T4 DNA) and full length T4 DNA molecules, respectively. As described herein the length of the DNA molecule correlates to the length of the generated current transient.

DETAILED DESCRIPTION OF THE INVENTION

A first aspect of the present invention is directed to a device comprising a biomolecular processor. Each biomolecular processor comprises one or more bioreactor chambers defined by a solid substrate, and a support structure within each bioreactor chamber that is attached to the solid substrate. The biomolecular processor also has a cleaving enzyme immobilized to the support structure and operatively positioned within said bioreactor chamber to cleave monomer or multimer units of a biopolymer molecule operatively engaged by the cleaving enzyme. The biomolecular processor also has one or more time-of-flight channels formed in the solid substrate and fluidically coupled to the one or more bioreactor chambers. Each of the one or more time-of-flight channels has an input end and an output end, where each of the one or more time-of-flight channels has two or more sensors including at least (i) a first sensor contacting the one or more time-of-flight channels proximate to the input end of the one or more time-of-flight channels and (ii) a second sensor contacting the one or more time-of-flight channels proximate to the output end of the one or more time-of-flight channels.

The biomolecular processor of the device may further contain a feeder channel that is also defined by walls of said solid substrate. The feeder channel has a length extending from an input end proximate to the surface of the solid substrate to an output end that is proximate to one or more of the bioreactor chambers.

In one embodiment, the device of the present invention comprises 100-1,000 biomolecular processors, 1,000-10,000 biomolecular processors, or 10,000-100,000 biomolecular processors. In another embodiment, the device of the present invention comprises more than 100,000 biomolecular processors.

Figure 1:
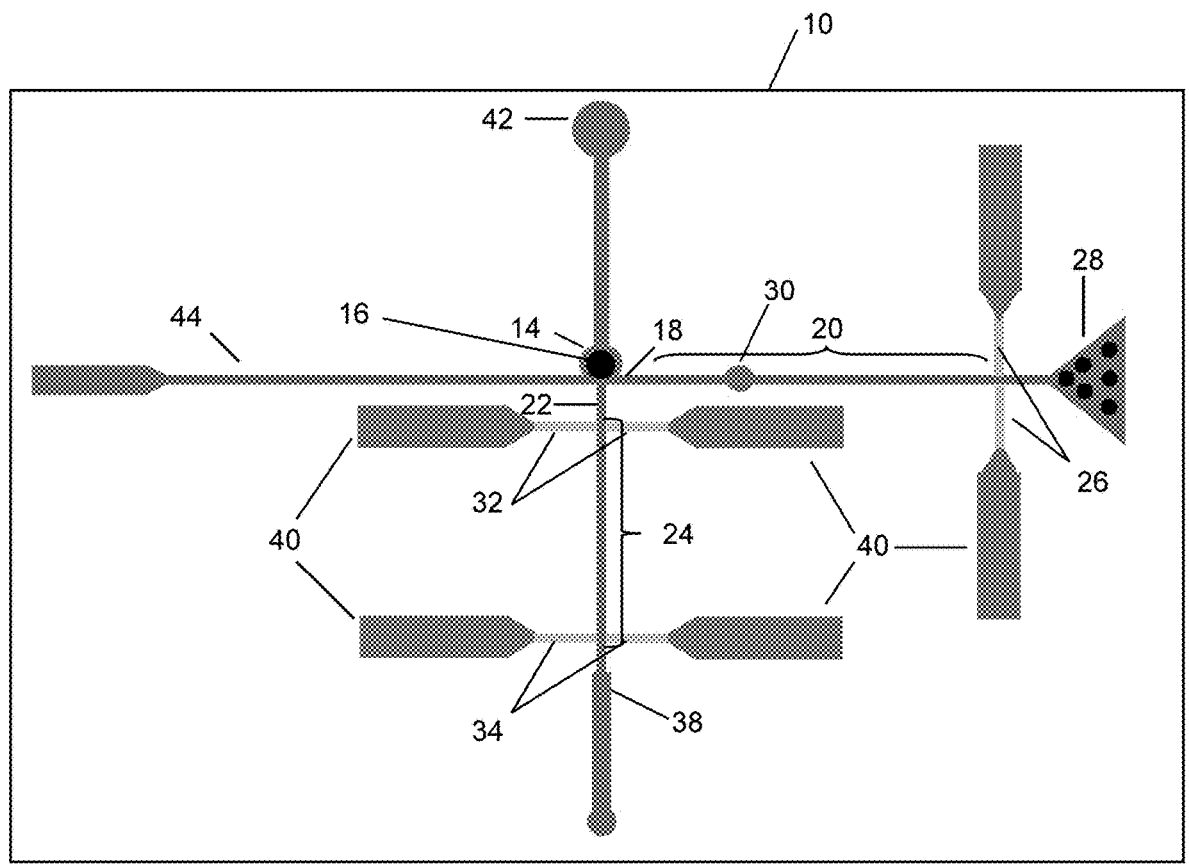
FIG. 1 is a top view schematic of a biomolecular processor of the present invention.

FIG. 1 is a top view schematic of a biomolecular processor 10 of a device of the present invention. The biomolecular processor comprises various multi-scale fluidic networks and micro- and nanostructures that function together to identify and/or sequence a biopolymer molecule present in a sample. In particular the biomolecular processor has a sample inlet 28 located at the input end of a feeder channel 20 that is capable of receiving a sample containing a biopolymer molecule, such as a nucleic acid molecule or protein. The feeder channel 20 is fluidically coupled at its output end to a bioreactor chamber 14 that contains a cleaving enzyme immobilized to a solid support structure 16 within the bioreactor chamber 14. The cleaving enzyme engages and cleaves the biopolymer into monomer or multimer units as it enters the bioreactor chamber from the feeding channel 20. The cleaved monomer or multimer units subsequently enter the fluidically coupled time-of-flight channel 24. As described in more detail herein, the time-of-flight channel contains at least two sensors 32, 34 that detect the cleaved monomer or multimer units as they are electrokinetically transported through the channel. The time it takes for a cleaved monomer or multimer unit to pass the first and second sensors in the time-of-flight channel is the "flight time" of the monomer or multimer unit. The flight time of the cleaved units is used to characterize and/or identify the monomer or multimer unit and/or the biopolymer molecule.

Figure 2A:
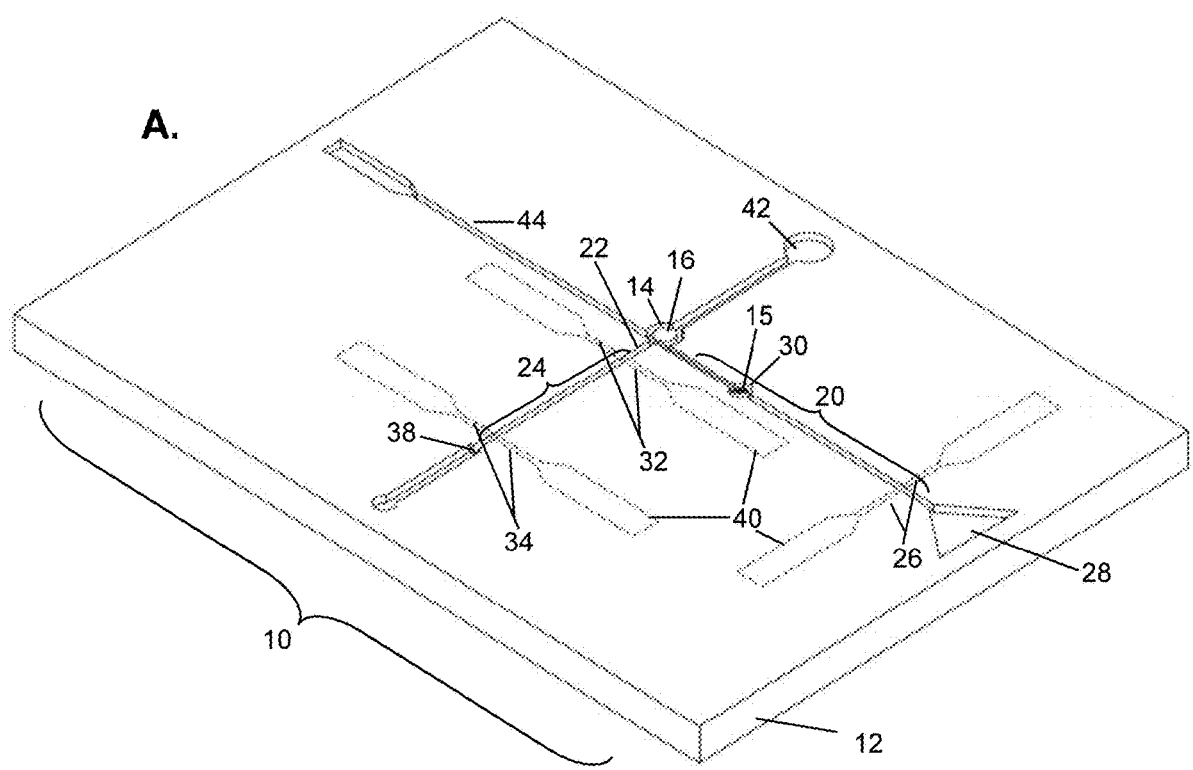
FIG. 2A is a perspective view of a biomolecular processor of the present invention.

FIG. 2 is a perspective view of the biomolecular processor of the device of the present invention. Not shown in this Figure is the coverplate of the biomolecular processor which fully encloses the microfluidic components of the device.

The solid substrate 12 of the biomolecular processor 10 may be a polymeric material or other moldable material. Suitable polymeric materials include, without limitation, poly(methyl methacrylate) (PMMA), polycarbonates (PC), epoxy-based resins, copolymers, polysulfones, elastomers, cyclic olefin copolymer (COC), and polymeric organosilicons. Alternatively, the solid substrate 12 of the biomolecular processor 10 may be glass, silica or a fused silica substrate material.

With reference to FIG. 2, the feeder channel 20 of the biomolecular processor 10 is defined by walls within the solid substrate 12. The feeder channel 20 has a sample inlet 28 at the input end, and is fluidically coupled to a bioreactor chamber 14 at its output end 18. The feeder channel receives and orientates a biopolymer molecule, e.g., a nucleic acid molecule 15, prior to feeding it into the bioreactor chamber for enzymatic processing.

Figures 3A, 3B, 3C, 3D:
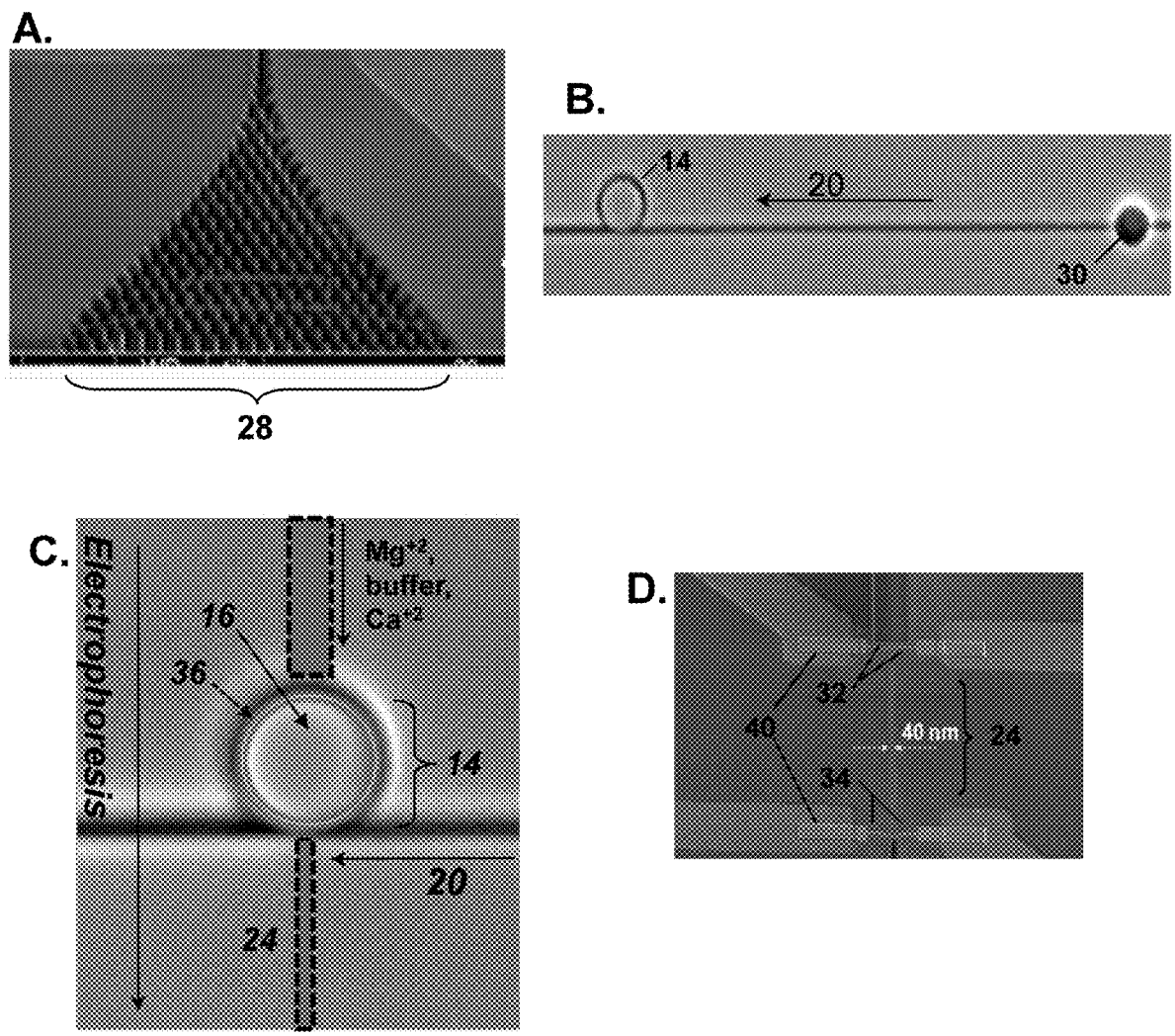
FIGS. 3A-3D are scanning electron micrograph (SEM) images of various portions of the biomolecular processor of the present invention.
Figure 4A:
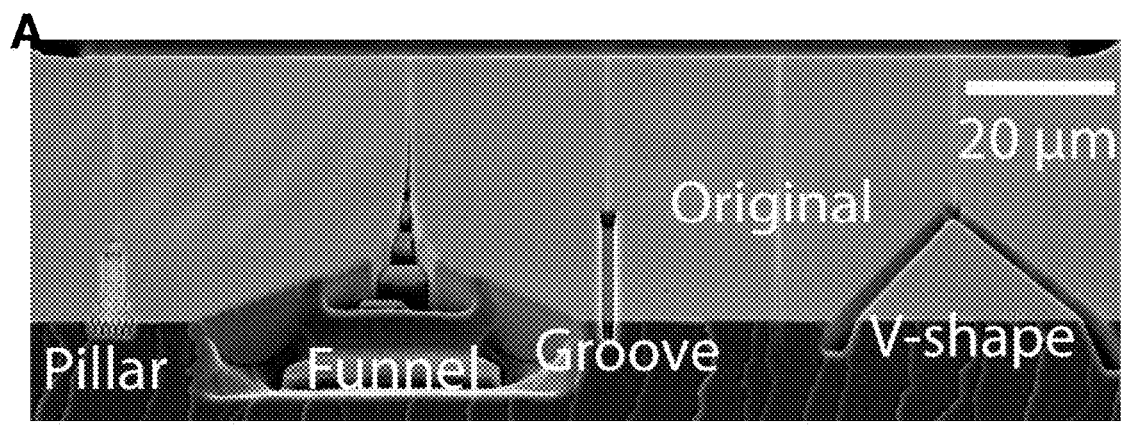
FIGS. 4A-4B show various designs of the feeder channel sample inlets.
Figure 4B:
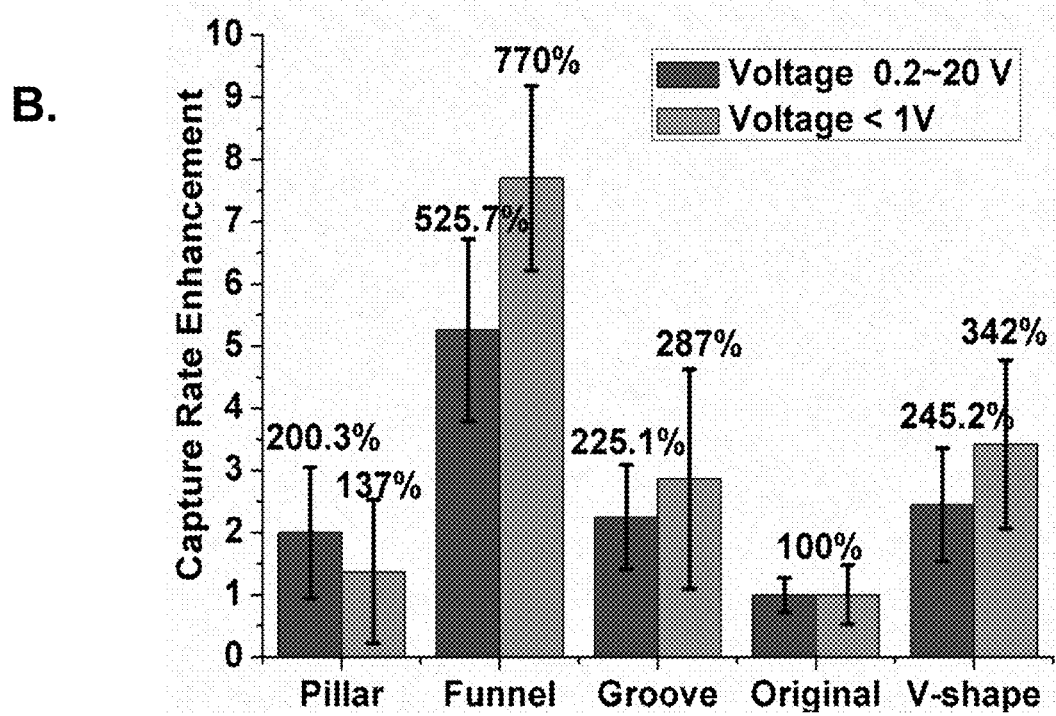

A sample containing one or more biopolymer molecules enters the biomolecular processor via a feeder channel inlet 28. The sample inlet may be modified structurally in various ways to facilitate capture and loading of a biopolymer molecule into the biomolecular processor from another module or component of the device. For example, the sample inlet may be a simple micro/sub-micron groove inlet, a V-shape micro/sub-micron groove inlet, a pillar inlet with an array of micro/nanopillars, or a funnel inlet as shown in FIGS. 3A and 4A. FIG. 4B is a graph showing that modified inlet structures significantly increase the rate of DNA capture and loading into a feeder channel at various driving voltages as compared to an abrupt microfluidic network to nanochannel interface (labeled as "original" in FIG. 4B).

In one embodiment of the present invention, the dimensions of the feeder channel are less than or equal to 100 nm wide and less than or equal to 100 nm deep. In another embodiment of the present invention, the dimensions of the feeder channel are less than or equal to 75 nm wide and less than or equal to 75 nm deep. In another embodiment of the present invention, the dimensions of the feeder channel are less than or equal to 50 nm wide and less than or equal to 50 nm deep. The length of the feeder channel is preferably in the range of about 1 m to about 100 m or longer, although longer and shorter feeder channel lengths are also suitable for the biomolecular processor of the present invention. The feeder channel may have any desired geometrical cross-section, i.e., circle, triangle, square, rectangle, pentagon, hexagon, heptagon, or octagon.

In reference to FIG. 2, the feeder channel of the biomolecular processor may further comprise one or more entropic traps 30 that are used for shaping, stretching, and positioning a biopolymer molecule, such as a nucleic acid molecule 15, within the feeder channel 20. Suitable entropic nucleic acid traps are known in the art, see e.g., Han and Craighead, "Separation of Long DNA Molecules in Microfabricated Entropic Trap Array," *Science* 288: 1026-1029 (2000), O'Donnell et al., "Pressure-driven DNA Transport Across an Artificial Nanotopography," *New Journal of Physics* 11: 075032 (2009), and Reisner et al., "Direct Self-Organization of Single DNA Molecules in a Nanoslit via Embedded Nanopt Arrays," *Proc. Natl. Acad. Sci. USA* 106: 79-84 (2009), which are hereby incorporated by reference in their entirety.

The feeder channel may further contain one or more pre-processing chambers or traps used to orient or process the biopolymer molecule prior to downstream enzymatic cleavage in the bioreactor chamber. For example, if the biopolymer is an mRNA molecule, the molecule may need to be decapped or deadenylated to create a suitable substrate for enzymatic cleavage. Suitable processing enzymes can be tethered or coupled to the walls of the feeder channel or walls of a pre-bioreactor processing chamber located in the feeder channel upstream of the bioreactor chamber.

The entropic trap, feeder channel, and any other pre-bioreactor processing chamber may also contain immobilized capture oligonucleotides. These capture oligonucleotides immobilized to the walls or support structures within the channel, traps, or chambers may comprise a homopolymer repeat sequence that is complementary to an end of the biopolymer molecule, e.g., a nucleic acid, that is fed through the channel. Hybridization between the immobilized capture oligonucleotides and complementary regions of the bipolymer molecule help orient the molecule as it traverses the feeder channel.

The feeder channel 20 may also comprise one or more sensors 26 that intersect the feeder channel. As shown in the embodiments depicted in FIGS. 1 and 2, the feeder channel 20 comprises a sensor 26, e.g., a pair of sensing electrodes, proximate to the input end of the feeder channel 20 that is capable of measuring electrical signals perpendicular to the feeder channel 20. Each of the sensing electrodes 26 is coupled to a micro-contact pad 40 that provides a connection to the external electrical components of the biomolecular processor. As a biopolymer molecule 15 passes the sensing electrodes 26, a perturbation in electrical signal is detected, and the duration of this perturbance can provide an approximation of the length of the molecule (Liang et al., "Nanogap Detector Inside Nanofluidic Channel for Fast Real-Time Label Free DNA Analysis," Nano Lett. 8(5):1472-1476 (2008), which is hereby incorporated by reference in its entirety).

The feeder channel 20 of the biomolecular processor 10 is fluidically coupled at its output end 18 to a bioreactor chamber 14. FIG. 3B is a scanning electron micrograph (SEM) showing a portion of the feeder channel 20 containing an entropic trap 30 coupled to the bioreactor chamber 14. The bioreactor chamber 14 is also defined by walls of the solid substrate of the biomolecular processor and is about 100 to about 1000 nm wide. As shown in SEM of FIG. 3C, the bioreactor chamber 14 contains a support structure 16, such as a pillar, having one or more cleaving enzymes 36, e.g., an exonuclease, exoribonuclease, or protease, covalently attached. The support structure of the bioreactor chamber may comprise the same or different material as the solid substrate of the biomolecular processor. In one embodiment, the support structure is a polymer support structure (e.g., PMMA, PC, or COC polymer). The support structure of the bioreactor chamber is about 50 nm to about 900 nm in width and about 10 nm to about 100 nm tall. The surface area of the support structure is about 1500 to about 285,000 nm$^2$. The cleaving enzyme immobilized on the support structure engages and cleaves a biopolymer molecule that enters the bioreactor chamber 14 from the output end 18 of the feeder channel 20. In some embodiments, the cleaving enzyme may require activation. Buffers containing activating agents, e.g., Mg$^{+2}$, or electrophoresis buffers are stored in a storage chamber 42 that is fluidically coupled to the bioreactor chamber 14 (FIG. 2).

Figure 2B:
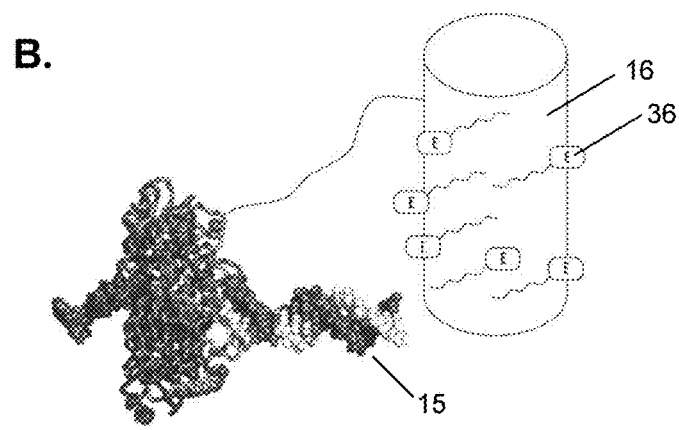
FIG. 2B shows the cleaving enzyme 36 immobilized to the bioreactor support structure 16 and operatively engaged with a nucleic acid molecule 15.
Figures 5A, 5B:
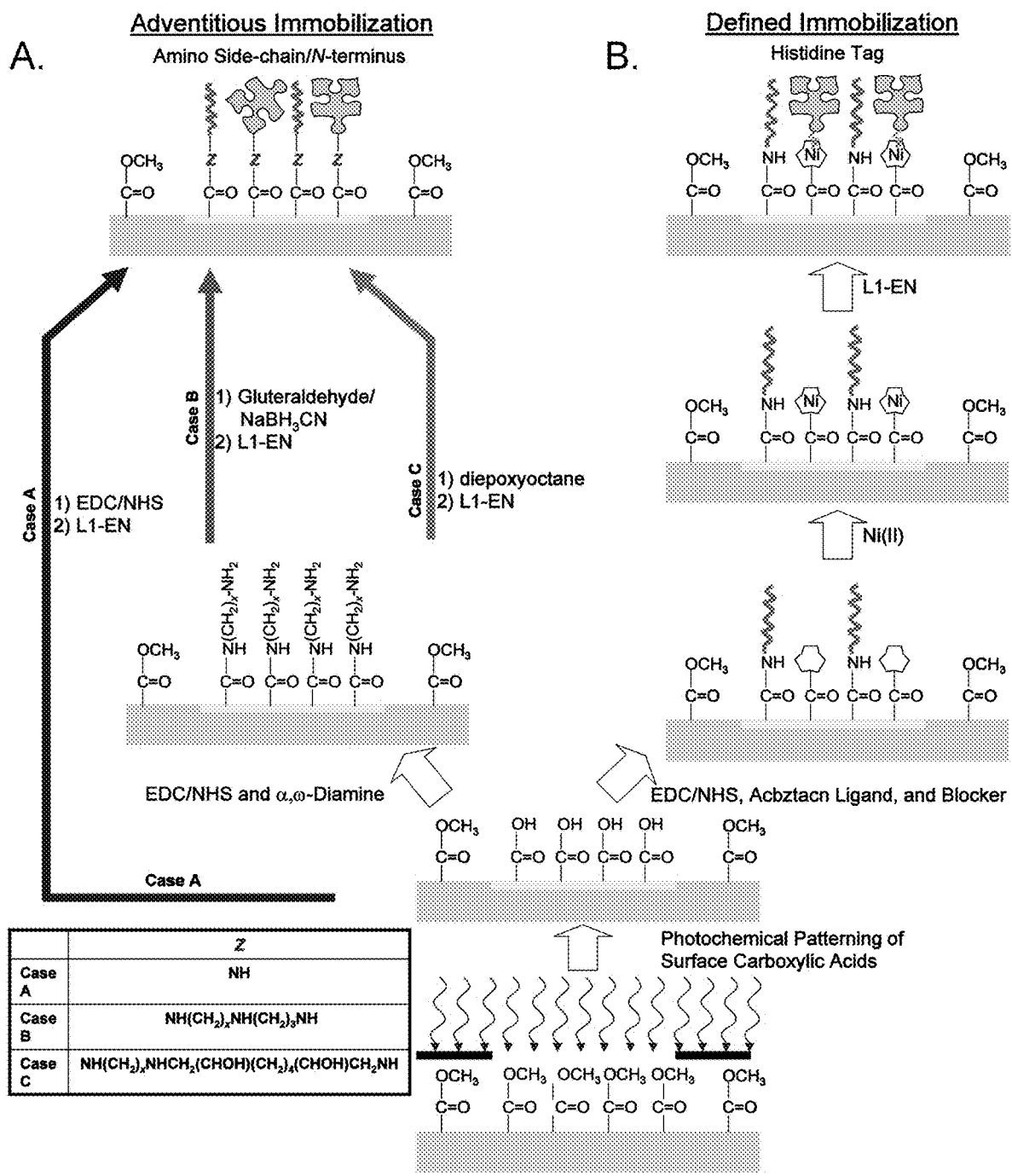
FIGS. 5A-5B are schematics showing alternative approaches for immobilizing a cleaving enzyme or enzymes to a solid support in the bioreactor chamber of the device of the present invention.

FIG. 2B shows the cleaving enzyme 36 immobilized on the bioreactor support structure 16 and engaged with a nucleic acid molecule 15. The cleaving enzyme may be tethered to the support structure of the bioreactor chamber using standard coupling chemistry known in the art. In one embodiment, the enzyme is tethered to the support structure via adventitious immobilization (FIG. 5A). Commercially-available cleavage enzymes such as exonucleases (New England Biolabs) or other enzymes can be immobilized using well-established carbodiimide (1-ethyl-3-(3-dimethylaminopropyl)carbodiimide, EDC) chemistries routinely utilized for a variety of antibodies (McCarley et al., "Resist-Free Patterning of Surface Architectures in Polymer-Based Microanalytical Devices," J. Am. Chem. Soc. 127:842-843 (2005); Chen et al., "Functional Template-Derived Poly(methyl methacrylate) Nanopillars for Solid-Phase Biological Reactions," Chem. Mater. 19:3855-3857 (2007); and Wang et al., "Microarrays Assembled in Microfluidic Chips Fabricated From Poly(methyl methacrylate) for the Detection of Low-Abundant DNA Mutations," Anal. Chem. 75:1130-1140 (2003), which are hereby incorporated by reference in their entirety).

In another embodiment of the present invention, the cleaving enzyme is tethered to the support structure via the immobilization of a suitable capture moiety, where the enzyme contains or is engineered to contain a capture moiety binding partner. For example, in one embodiment, the surface of the support structure contains a plurality of capture ligands bound to Ni(II) that allow for enzyme immobilization using a hexahistidine tag engineered enzyme (FIG. 5B) (Dapprich, J., "Single-Molecule DNA Digestion by Lambda-Exonuclease," Cytometry 36:163-168 (1999), which is hereby incorporated by reference in its entirety). The Ni(II) surfaces can be generated by coordinating Ni(II) to CT-PMMA that has been modified with 1-acetato-4-benzyl-triazacyclononane (Acbztacn) (Johnson & Martin, "Controlling Protein Orientation at Interfaces Using Histidine Tags: An Alternative to Ni/NTA," J. Am. Chem. Soc. 127:2018-2019 (2005); Warden et al., "Synthesis of Novel Derivatives of 1,4,7-Triazacyclononane," Organic Lett. 3:2855-2858 (2001), which are hereby incorporated by reference in their entirety) or nitrilotriacetic acid (NTA). Acbztacn-PMMA surfaces can be formed by exposure of CT-PMMA surfaces to EDC/Acbztacn to form amide linkages of the Acbztacn to the PMMA through the secondary amine of the triazacyclononane (see FIG. 5B) (Johnson & Martin, "Controlling Protein Orientation at Interfaces Using Histidine Tags: An Alternative to Ni/NTA," J. Am. Chem. Soc. 127:2018-2019 (2005), which is hereby incorporated by reference in its entirety).

Alternative capture and binding partners that can be used to tether the cleaving enzyme or enzymes to the support structure include, without limitation, biotin and streptavidin, maltose and maltose binding protein, chitin and chitin binding protein, amylase and MBP, glutathione transferase and glutathione-S-transferase, integrin and integrin binding peptides, nucleic acid oligonucleotides or nucleic acid analogue oligonucleotides and their complementary oligonucleotides.

In another embodiment, the enzyme is tethered to the support structure using immobilized antibodies. For example, the cleaving enzyme, which has been engineered to contain a hexahistidine tag, can be immobilized to the support structure via anti-His-Tag antibodies (Perkins et al., "Sequence-Dependent Pausing of Single Lambda Exonuclease Molecules," Science 301:1914-1918 (2003), which is hereby incorporated by reference in its entirety). Immobilization of commercially-available anti-histidine-Tag antibodies (Roche, Qiagen, or Novagen) or other antibodies can be achieved using well-established carbodiimide (1-ethyl-3-(3-dimethylaminopropyl)carbodiimide, EDC) chemistries routinely utilized for a variety of antibodies (McCarley et al., "Resist-Free Patterning of Surface Architectures in Polymer-Based Microanalytical Devices," J. Am. Chem. Soc. 127:842-843 (2005); Chen et al., "Functional Template-Derived Poly(methyl methacrylate) Nanopillars for Solid-Phase Biological Reactions," Chem. Mater. 19:3855-3857 (2007); and Wang et al., "Microarrays Assembled in Microfluidic Chips Fabricated From Poly(methyl methacrylate) for the Detection of Low-Abundant DNA Mutations," Anal. Chem. 75:1130-1140 (2003), which are hereby incorporated by reference in their entirety). Additional embodiments of antibody capture of enzyme containing an engineered peptide capture sequence include but are not limited to: FLAG epitope with Anti-FLAG antibody; and Myc tag epitope with Anti-Myc Tag antibody.

Surface coverage of the support structure by the cleaving enzyme can be assessed by evaluation of protein content in immobilization solutions before and after immobilization (solution difference method) (Smith et al., "Measurement of Protein Using Bicinchoninic Acid," *Anal. Biochem.* 150:76-85 (1985); Stoscheck, C. M., "Quantitation of Protein," *Methods in Enzymol.* 182:50-68 (1990), which are hereby incorporated by reference in their entirety), and its activity will be determined using standard kinetic methods (Chen et al., "Functional Template-Derived Poly(methyl methacrylate) Nanopillars for Solid-Phase Biological Reactions," *Chem. Mater.* 19:3855-3857 (2007), which is hereby incorporated by reference in its entirety).

In one embodiment of the present invention, the immobilized cleaving enzyme of the bioreactor chamber is an exonuclease. As used herein an "exonuclease" encompasses any enzyme capable of catalyzing the hydrolysis of a single nucleotide from the end of a DNA or RNA molecule. In one embodiment, the exonuclease is a processive enzyme, i.e., it catalyzes a series of successive cleavage events of a template without releasing the template. Such exonucleases can be monomeric enzymes, multimeric enzymes, or enzyme complexes comprised of multiple subunits. Suitable exonucleases include, without limitation, lambda exonuclease, which cleaves double-stranded and single-stranded DNA substrates in the 5'-3' direction; exonuclease I, which cleaves single-stranded DNA substrates in the 3'-5' direction; exonuclease III, which cleaves double-stranded DNA substrates in the 3'-5' direction; T7 exonuclease, which cleaves double-stranded DNA substrates, or RNA/DNA hybrid substrates in the 5'-3' direction; XRN-1, which cleaves single-stranded RNA substrates in the 5'-3' direction (Geisler and Coller, "XRN1: A Major 5' to 3' Exoribonuclease in Eukaryotic Cells," Enzymes 31:97-110 (2012), Jinek et al., "Coupled 5' Nucleotide Recognition and Processivity in Xrn1-Mediated mRNA Decay," *Mol. Cell* 41:600-608 (2011), and Jones et al., "The 5'→3' Exoribonuclease XRN1/Pacman and its Functions in Cellular Processes and Development," WIREs RNA 3:455-468 (2012), which are hereby incorporated by reference in their entirety); RNase II, which cleaves single-stranded RNA substrates in the 3'-5' direction (Zuo et al., "Structural Basis for Processivity and Single-Strand Specificity of RNaseII," *Mol. Cell* 24:149-156 (2006), which is hereby incorporated by reference in its entirety); and exosome complex, which cleaves single-stranded RNA substrates in the 3'-5' direction (Lee et al., "Elastic Coupling Between RNA Degradation and Unwinding by an Exoribonuclease, *Science* 336:1726-1729 (2012), which is hereby incorporated by reference in its entirety). The support structure of the bioreactor chamber may comprise any one or more of the aforementioned exonuclease enzymes. In some embodiments, a combination of enzymes, such as, e.g., an exosome complex in combination with XRN-1, ensures cleavage of an RNA molecule regardless of RNA orientation (i.e., 5'-3' or 3'-5') as it enters the bioreactor chamber. In some embodiments, a prior processing step may be needed, for example decapping messenger RNA to create a 5' phosphorylated substrate for XRN-1, or deadenylation of messenger RNA to create a suitable substrate for the Exosome complex. Such additional enzymes may be present in pre-reaction chambers, the feeder channel, or attached to the support structure of the bioreactor chamber.

In another embodiment of the present invention, the immobilized cleaving enzyme of the bioreactor chamber is a protease or peptidase. As used herein, "protease" and "peptidase" are used interchangeably to refer to any enzyme capable of proteolysis by hydrolysis of peptide bonds. Suitable proteases include, without limitation, serine proteases, threonine proteases, cysteine proteases, aspartate proteases (cleave at the amino side of aspartate residues), asparagine proteases, lysine proteases (cleaves at the carboxyl side of lysine residues), metalloproteases, and glutamic acid proteases (cleaves at the carboxyl side of glutamate or aspartate). Particular proteases that are suitable for use in the present invention include, without limitation, proteinase K, which cleaves at the carboxyl side of aliphatic, aromatic, and hydrophobic residues; *S. aureus* V-8 Protease which cleaves at the carboxyl side of aspartate and glutamate residues; trypsin, which cleaves at the carboxyl side of arginine and lysine residues; and chymotrypsin, which cleaves at the carboxyl side of tyrosine, phenylalanine, tryptophan and leucine.

As shown in FIG. 2, the bioreactor chamber 14 is fluidically coupled to output channel 44 that runs opposite the feeder channel 20. The output channel 44 may serve to collect non-cleaved biopolymer components, e.g., when the biopolymer molecule is a double stranded DNA molecule and only one strand of the DNA is cleaved by the cleaving enzyme, the output channel collects the non-digested strand of DNA. Alternatively, the output channel may serve as a second feeder channel, collecting non-digested biopolymer units and transporting them downstream to one or more other bioreactor chambers for cleavage.

The bioreactor chamber 14 is also fluidically coupled to a time-of-flight channel 24 that is defined by walls of the solid substrate 12 of the biomolecular processor 10. The dimensions of the time-of-flight channel are less than or equal to 50 nm wide and less than or equal to 50 nm deep. In another embodiment of the present invention, the dimensions of the time-of-flight channel are less than or equal to 25 nm wide and less than or equal to 25 nm deep. In another embodiment of the present invention, the dimensions of the time-of-flight channel are less than or equal to 15 nm wide and less than or equal to 15 nm deep. In another embodiment of the present invention, the dimensions of the time-of-flight channel are less than or equal to 10 nm wide and less than or equal to 10 nm deep. In another embodiment of the present invention, the dimensions of the time-of-flight channel are less than or equal to 5 nm wide and less than or equal to 5 nm deep. The time-of-flight channel can be 1 m to >250 rpm in length or 5 μm to 250 μm in length, and may have any desired geometrical cross-section, i.e., hemispherical, triangle, square, rectangle, pentagon, hexagon, heptagon, or octagon.

Figure 6A:
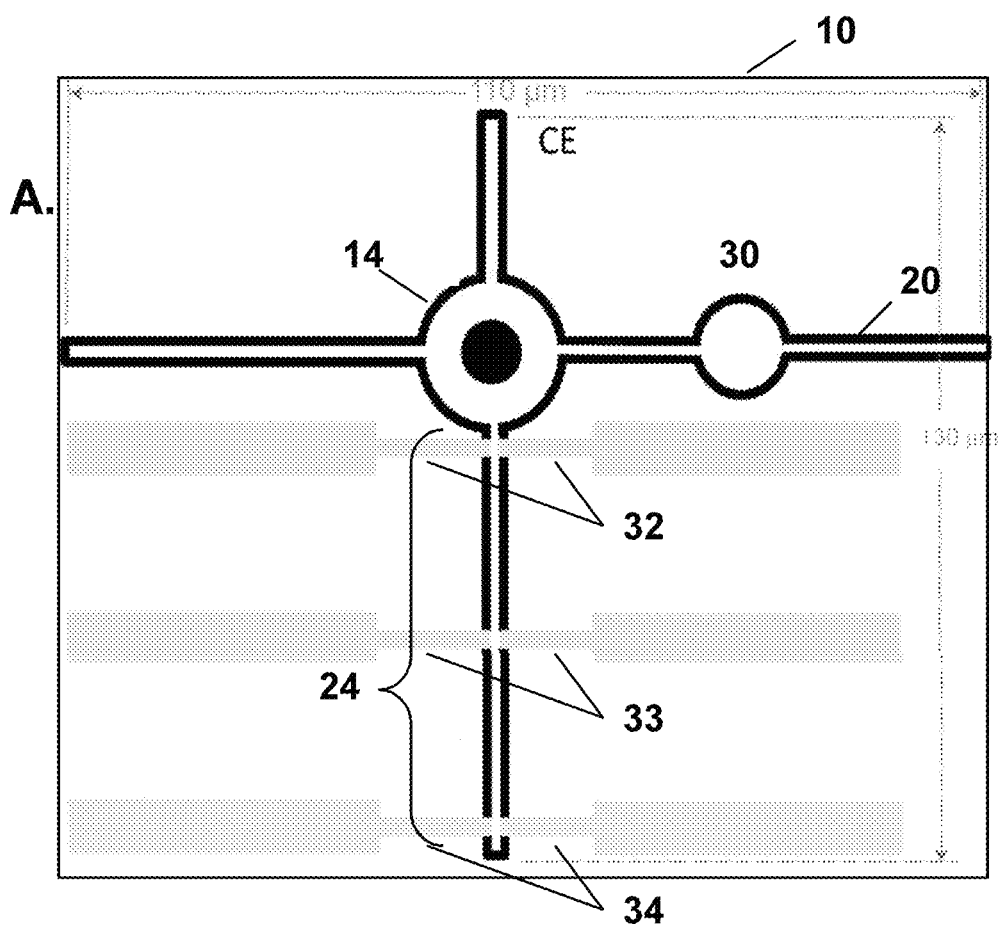
FIG. 6A-6B show a biomolecular processor of the present invention having a time-of-flight channel that contains three nanosensing electrodes.
Figure 7:
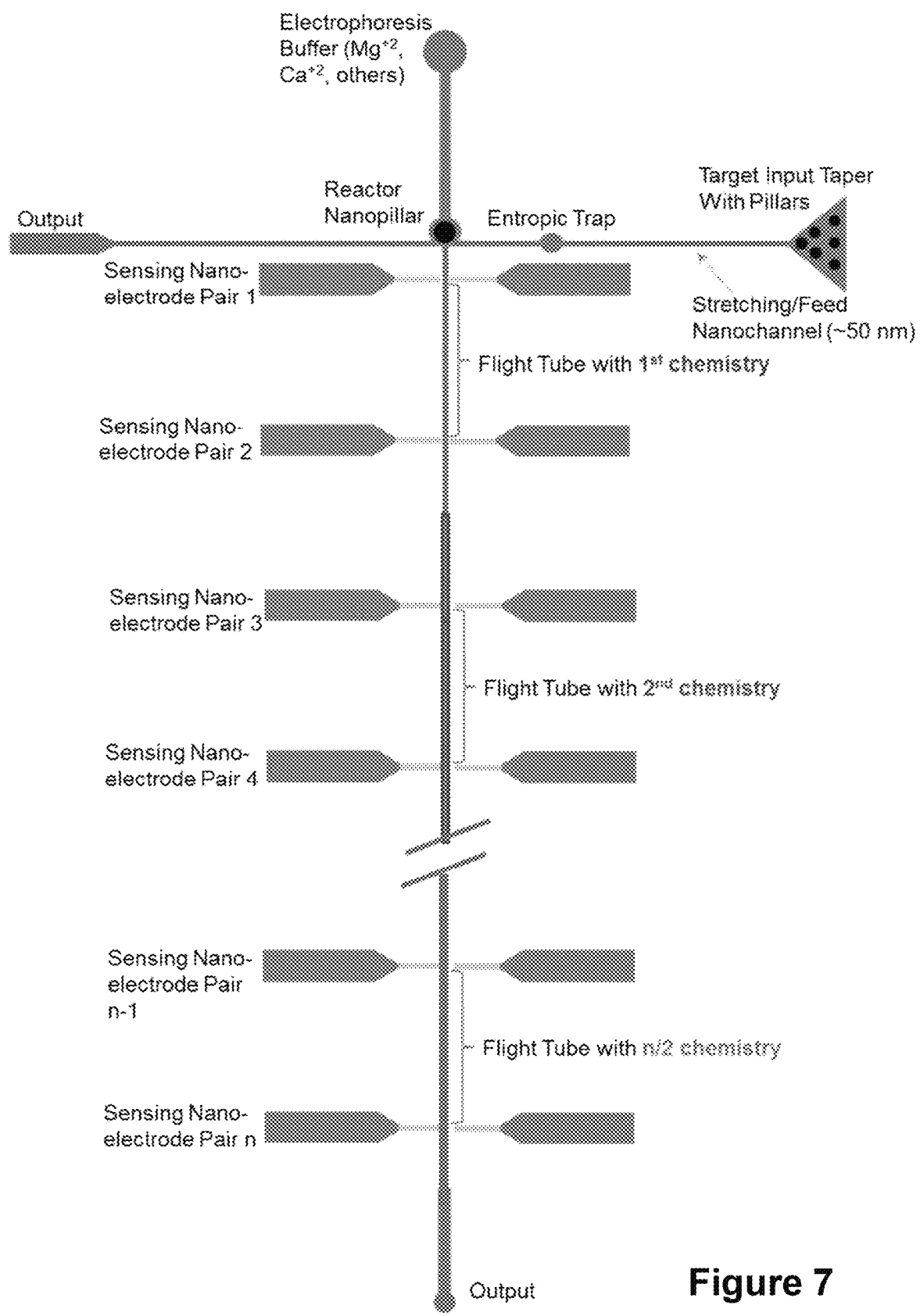
FIG. 7 is a top view of a biomolecular processor of the present invention where the time-of-flight channel contains multiple flight tubes, each flight tube having two pairs of nanosensing electrodes separated by a portion of the time-of-flight channel having a unique surface chemistry. The first and second sensors of each flight tube detect the flight time of a biopolymer unit as a function of the particular flight tube surface chemistry.

As shown in FIG. 2 and the SEM of FIG. 3D, the time-of-flight channel 24 has at least a first sensor 32, e.g., a pair of nanosensing electrodes that intersect the time-of-flight channel 24 proximate to the input end 22 of the time-of-flight channel 24, and a second sensor 34, e.g., a pair of nanosensing electrodes that intersect the time-of-flight 24 channel proximate to the output end 38 of the time-of-flight channel 24. Each of the nanosensing electrodes is coupled to a microcontact pad 40 that provides a connection to the external electrical and detector components of the biomolecular processor. The time-of-flight channel may contain more than two sensors. As shown in FIG. 6A, the time-of-flight channel 24 may comprise at least a first 32, second 34, and third 33 sensor, e.g. three pairs of nanosensing electrodes. As shown in FIG. 7, the time-of-flight channel may comprise more than three sensors.

The nanosensing electrodes of the time-of-flight channel are capable of measuring electrical signatures perpendicular to the channel. In one embodiment of the present invention, each pair of electrodes is capable of detecting a change in the current running between the electrodes when a molecular entity resides or passes between the electrodes due to change in solution conductance or impedance.

Figure 6B:
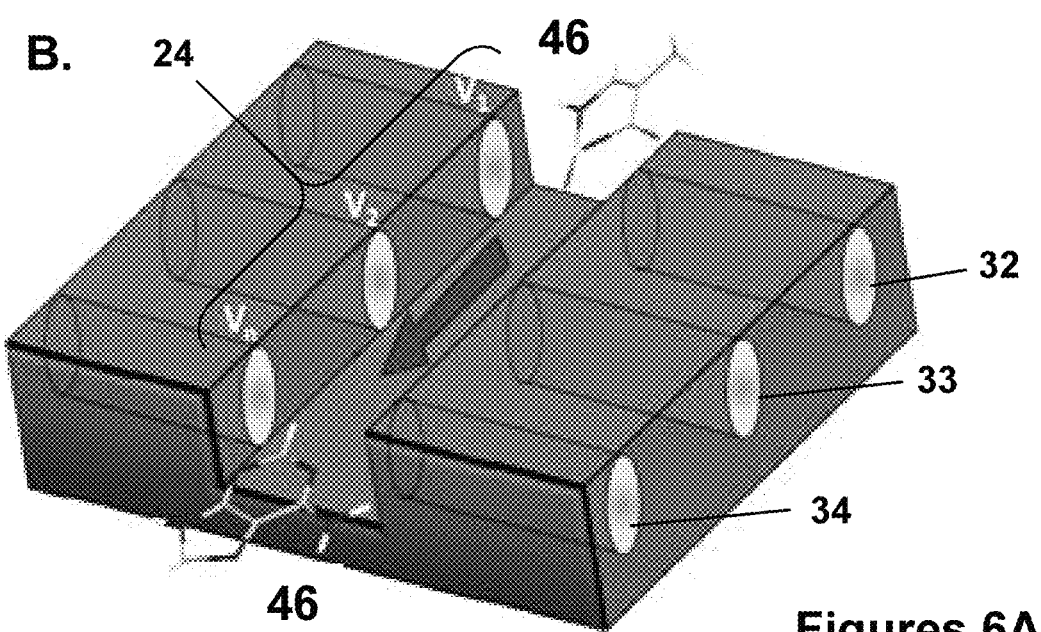

The device of the present invention also has an electric field generator operatively positioned to create an electric field in the one or more bioreactor chambers and along the length of the one or more time-of-flight channels. The electric field is applied to the bioreactor chamber 14 and time-of-flight channel 24, to electrokinetically transport cleaved units of a biopolymer molecule out of the bioreactor chamber 14 and through the time-of-flight channel 24. As the cleaved monomer or multimer units move through the time-of-flight channel 24 they are detected by at least the first 32 and second 34 sensors, and any additional sensors in the time-of-flight channel. A three-dimensional depiction of mononucleotides cleaved from a nucleic acid molecule traversing a time-of-flight channel containing three sensors is shown in FIG. 6B. As described herein, the flight time of each biopolymer unit between two or more sensors (e.g., between a first and second pair of nanoelectrode and/or between a second and third pair of nanoelectrodes) is used to identify and/or characterize the identity of the cleaved biopolymer unit. In addition, the electrical peak amplitude of a cleaved unit as detected by the first and/or second or more sensors is also used to help identify and/or characterize the cleaved biopolymer unit.

The travel time of a biopolymer unit through the time-of-flight channel is determined by the applied electric field, the length of the time-of-flight channel and the number of biopolymer unit-to-channel wall interactions or differences in the electrophoretic mobility of the individual biopolymer units. In cases where the wall interactions or electrophoretic mobilities are molecular dependent (e.g., mononucleotide bases), the flight-times will provide a direct indicator of the identity of the biopolymer unit.

Molecular specific interactions between a biopolymer unit and the wall or walls of the time-of-flight channel can be controlled by the composition and functionalization of the time-of-flight channel walls. In one embodiment, the walls of the time-of-flight channel comprise the same composition as the substrate, with or without modification. Alternatively, the wall or walls of the flight channel may comprise a different composition than the substrate, with or without modification. In another embodiment, the molecular-dependent flight time is determined by unique electrophoretic mobilities of each cleaved biopolymer unit and as such, no wall interactions are required.

In one embodiment of the present invention, the time-of-flight channel comprises a polymeric material, e.g., PMMA, PC, epoxy-based resins, copolymers, polysulfones, elastomers, and polymeric organosilicons, or any combination of these materials. The polymeric material may be in its native state, or, alternatively, surface modified to enhance biopolymer unit discrimination. For example, a polymeric time-of-flight channel wall may comprise a neutral, hydrophobic, hydrocarbon surface with different degrees of chain order. In another example, the time-of-flight channel wall surface may comprise a charge neutral, hydrophilic surface. In yet another example, the time-of-flight channel wall surface may comprise a charged, hydrophilic surface.

A time-of-flight channel wall surface comprising a neutral, hydrophobic, hydrocarbon surface with different degrees of chain order can be formed from monolayers of methyl-terminated alkane chains having various lengths that are built on the polymer nanochannel surfaces (Henry et al., "Surface Modification of Poly(methyl methacrylate) Used in the Fabrication of Microanalytical Devices," Anal. Chem. 72:5331-5337 (2000), which is hereby incorporated by reference in its entirety). The monolayers can be formed by attachment of amino-alkanes to carboxylic acid-terminated surfaces (McCarley et al., "Resist-Free Patterning of Surface Architectures in Polymer-Based Microanalytical Devices," J. Am. Chem. Soc. 127:842-843 (2005); Wei et al., "Photochemically Patterned Poly(methyl methacrylate) Surfaces Used in the Fabrication of Microanalytical Devices. J. Phys. Chem. B 109:16988-16996 (2005), which are hereby incorporated by reference in their entirety). Alternatively, the monolayers can be formed from urea-linked alkane layers on amine functionalities attached to the polymer via amide bonds (Henry, A. C., "Surface Modification and Characterization of PMMA Used in the Construction of Microelectromechanical Systems," In Chemistry, pp. 147, Louisiana State University, Baton Rouge (2001); Henry et al., "Surface Modification of Poly(methyl methacrylate) Used in the Fabrication of Microanalytical Devices," Anal. Chem. 72:5331-5337 (2000), which are hereby incorporated by reference in their entirety). For example, well-ordered octadecyl monolayers can be formed on PMMA surfaces by reaction of n-octadecylisocyanate with amine-terminated PMMA surfaces (Henry & McCarley, "Selective Deposition of Metals on Plastics Used in the Construction of Microanalytical Devices: Photo-Directed Formation of Metal Features on PMMA," J Phys. Chem. B 105:8755-8761 (2001), which is hereby incorporated by reference in its entirety), and these $C_{18}$-PMMA surfaces are excellent for chromatographic separations in embossed channels (Galloway et al., "Contact Conductivity Detection in Poly(methyl methacylate)-Based Microfluidic Devices for Analysis of Mono- and Polyanionic Molecules," Anal. Chem. 74:2407-2415 (2002), which is hereby incorporated by reference in its entirety). Thus, various chain length n-alkylisocyanates can be used to make hydrophobic polymer surfaces possessing different degrees of order, which will affect the flight-time of the monomers, such as dNMPs. Issues regarding non-zero electroosmotic flows (EOFs) can be addressed by capping unreacted foundation groups (Henry, A. C., "Surface Modification and Characterization of PMMA Used in the Construction of Microelectromechanical Systems," In Chemistry. Louisiana State University, Baton Rouge (2001); Wei et al., "Photochemically Patterned Poly(methyl methacrylate) Surfaces Used in the Fabrication of Microanalytical Devices. J. Phys. Chem. B 109:16988-16996 (2005), which are hereby incorporated by reference in their entirety).

The latter two objectives are accomplished by attaching materials possessing (a) glycol and (b) organic acid or amine termini to carboxyl- or amine-terminated polymer surfaces. One approach for creating hydrophilic, charge neutral surfaces, involves reacting properly activated carboxylic-acid terminated polymer surfaces with ethanolamine or amino-tri(ethyleneglycol) (Wei, S., "Multianalyte Detection of Breast Cancer by Fabrication of Hybridmicroarrays on Polymer-based Microanalytical Devices," In Chemistry. Louisiana State University, Baton Rouge (2005), which is hereby incorporated by reference in its entirety). As an alternative, amine-terminated PMMA and PC surfaces can be modified with glycols having surface generated carboxylic groups, such as glycolic acid or carboxyl-tri(ethyleneglycol). Cationic surfaces (at the pH conditions used for the exonucleases) can be formed using well-established methods for production of amine-terminated polymers (Henry & McCarley, "Selective Deposition of Metals on Plastics Used in the Construction of Microanalytical Devices: Photo-Directed Formation of Metal Features on PMMA," J. Phys. Chem. B 105:8755-8761 (2001); Henry et al., "Surface Modification of Poly(methyl methacrylate) Used in the Fabrication of Microanalytical Devices," *Anal. Chem.* 72:5331-5337 (2000); McCarley et al., "Resist-Free Patterning of Surface Architectures in Polymer-Based Microanalytical Devices," *J Am. Chem. Soc.* 127:842-843 (2005); Wei et al., "Photochemically Patterned Poly(methyl methacrylate) Surfaces Used in the Fabrication of Microanalytical Devices. *J. Phys. Chem. B* 109:16988-16996 (2005), which are hereby incorporated by reference in their entirety). Anionic surfaces will result from routes that lead to either carboxylic-acid terminated surfaces (McCarley et al., "Resist-Free Patterning of Surface Architectures in Polymer-Based Microanalytical Devices," *J. Am. Chem. Soc.* 127:842-843 (2005); Vaidya et al., "Surface Modification and Characterization of Microfabricated Poly(carbonate) Devices: Manipulation of Electroosmotic Flow," *Analyst* 127:1289-1292 (2002), which are hereby incorporated by reference in their entirety) or those bearing sulfonic acids, with the latter having an almost pH-independent surface charge (Henry, A. C., "Surface Modification and Characterization of PMMA Used in the Construction of Microelectromechanical Systems," In *Chemistry*, pp. 147, Louisiana State University, Baton Rouge (2001), which is hereby incorporated by reference in its entirety).

Most modification chemistries are based on creating a scaffold, for example carboxy groups, comprised of functional groups that can be regio-specifically patterned in that only certain locations are activated on the substrate by masking areas that are not intended to be activated and UV exposing this assembly (McCarley et al., "Resist-Free Patterning of Surface Architectures in Polymer-Based Microanalytical Devices," *J. Am. Chem. Soc.* 127:842-843 (2005); Wei et al., "Photochemically Patterned Poly(methyl methacrylate) Surfaces Used in the Fabrication of Microanalytical Devices. *J. Phys. Chem. B* 109:16988-16996 (2005), which are hereby incorporated by reference in their entirety). Monolayer elements can be selectively immobilized to only the nanochannel domains through masking, leaving the rest of the solid support substrate and structures therein in their native form. Even though the nanochannel dimensions are below the diffraction limit of the activating light (254 nm), the length of the channel is well above the diffraction limit and this is the critical dimension.

As shown in the FIG. 7, the biomolecular processor of the device of the present invention may comprise multiple flight tubes coupled together. Each flight tube has sensors that are separated by a portion of the time-of-flight channel. Each flight tube is characterized by a unique or different chemistry that differentially interacts with the cleaved biopolymer units. This design format allows for multidimensional biopolymer unit separations to enhance identification and characterization of individual biopolymer units. Further, such a device may be used for creating a fingerprint of peptide fragments generated from proteolysis of one or more proteins in an input sample. The utilization of time-of-flight channels with two or more sensors and/or two or more flight tubes having different wall surface chemistries to generate one or more flight time measurements per channel, creates a very sophisticated peptide fingerprint, for example a 2-dimensional (using 4 sensors), 3-dimensional (using 6 sensors), or 4-dimensional fingerprint (using 8 sensors) to distinguish essentially all possible proteins and their modifications from a given fraction (See FIG. 7).

As described supra, the sensors in the time-of-flight channel are capable of detecting cleaved biopolymer units as they transit through the channel. In one embodiment of the present invention, each sensor comprises a pair of sensing electrodes formed from a pair of noble metal nanowires, segmented nanowires, or nanoparticles separated by a nanogap across the channel. In another embodiment of the present invention, each pair of sensing electrodes have a narrow cross-section where they contact the time-of-flight channel. The nanowires have a diameter that is less than 50 nm, more preferably, less than about 30 nm, more preferably, less than about 10 nm. In another embodiment of the present invention, the nanowires have a diameter between about 5 nm and about 20 nm. The space between the sensing electrodes, i.e., the nanogap, is between 1 nm and 10 nm, and in some embodiments, between 1 nm and 5 nm. The sensing electrode and gap dimensions control the signal-to-noise ratio for multimer or monomer units, with smaller nanowire and gap dimensions giving a higher signal-to-noise ratio (Liang et al., "Nanogap Detector Inside Nanofluidic Channel for Fast Real-Time Label-free DNA Analysis," *Nano Letters* 8: 1472-1476 (2008), Tsutsui et al., "Identifying Single Nucleotides by Tunneling Current," *Nature Nanotechnology* 5: 286-290 (2010); Ohshiro et al., "Single-Molecule Electrical Random Resequencing of DNA and RNA," *Scientific Reports* 2: 1-7 (2012); which are hereby incorporated by reference in their entirety).

As described in more detail herein, the nanowires may be segmented nanowires formed from a combination of metallic component. Exemplary combinations include, without limitation, gold (Au) and cobalt (Co) (Au/Co) and Au and platinum (Pt).

The biomolecular processor is one module or component of the device of the present invention, and as noted above, the device may contain 100-100,000 biomolecular processors or more that 100,000 biomolecular processors. The biomolecular processor can interface with one or more front-end processing modules of the device to generate a highly integrated system for biopolymer analysis. The modular design approach allows the opportunity to mix-and-match different modules in a system to suit the application need. In addition, because the modules are autonomous, they can be optimized in terms of their performance metrics prior to system-level integration. Front end processing modules of the device include, for example and without limitation, a module for solid-phase extraction of nucleic acids from cell lysates, both DNA and RNA (Witek et al., "96-Well Polycarbonate-Based Microfluidic Titer Plate for High-Throughput Purification of DNA and RNA," Analytical Chemistry 80:3483-3491 (2008); Park et al., "A Titer Plate-Based Polymer Microfluidic Platform for High Throughput Nucleic Acid Purification," *Biomedical Microdevices* 10:21-33 (2008), which are hereby incorporated by reference in their entirety) or a module for protein/polypeptide isolation and enrichment, a module for shearing nucleic acids to the appropriate size for entry into the biomolecular processor, a thermal amplification module (Hashimoto et al., "Rapid PCR in a Continuous Flow Device," *Lab On A Chip* 4:638-645 (2004); Hashimoto et al., "Ligase Detection Reaction/Hybridization Assays Using Three-Dimensional Microfluidic Networks for the Detection of Low-Abundant DNA Point Mutations," *Analytical Chemistry* 77:3243-3255 (2005), which are hereby incorporated by reference in their entirety), rare cell selection modules (Adams et al., "Highly Efficient Circulating Tumor Cell Isolation From Whole Blood and Label-Free Enumeration Using Polymer-Based Microfluidics With an Integrated Conductivity Sensor," *J. Am. Chem. Soc.* 130:8633-8641 (2008); Dharmasiri et al., "Capture and Enumeration of LNCaP Prostate Cancer Cells Using Aptamers Immobilized to a PMMA Microsampling Unit," *Electrophoresis* 30:3289-3300 (2009), which are hereby incorporated by reference in their entirety) and DNA arrays (Xu et al., "Polymer Microfluidic Chips with Integrated Waveguides for Reading Microarrays," *Analytical Chemistry* 79:9007-9013 (2007), which is hereby incorporated by reference in its entirety).

Another aspect of the present invention is directed to a method for nucleic acid molecule sequencing using a device of the present invention that contains a biomolecular processor. The method involves feeding a sample containing one or more nucleic acid molecules into the biomolecular processor of the device under conditions effective for the immobilized cleaving enzyme to engage the one or more nucleic acid molecules in the sample and to cleave the one or more nucleic acid molecules into monomer nucleotides that individually enter the input end of the one or more time-of-flight channels. The method further involves applying an electric field across the one or more bioreactor chambers and along the length of the one or more time-of-flight channels to transport the cleaved monomer nucleotides through the one or more time-of-flight channels. The cleaved monomer nucleotides are detected, based on said applying, as they pass at least the first and second sensors in the one or more time-of-flight channels. How long it takes for each cleaved monomer nucleotide to pass at least the first and second sensors in the one or more time-of-flight channels is measured, and the cleaved monomer nucleotides are identified based on the measurements.

As described supra, the biomolecular processor of the device may further contain a feeder channel that is fluidically coupled to the bioreactor chamber. The feeder channel can contain one or more entropic traps and preprocessing chambers that orientate and elongate the nucleic acid molecule prior to cleavage in the bioreactor chamber. Accordingly, in some embodiments of the present invention, the sample comprising the one or more nucleic acid molecule is introduced into the channel sample inlet of a feeder channel. An electric field is applied along the length of the feeder channel to elongate the nucleic acid molecule through the feeder channel before it enters the bioreactor chamber.

Nucleic acid molecules that can be sequenced using the method and device of the present invention include, without limitation, deoxyribonucleic acid (DNA) molecules and ribonucleic acid (RNA) molecules. Specifically, double stranded DNA, single stranded DNA molecules, DNA and RNA molecules comprising one or more methylated nucleotide bases, DNA and RNA molecules comprising one or more modified or damaged nucleotide bases. In particular, the method of the present invention can readily identify DNA and RNA molecules comprising one or more nucleotide base insertions, deletions, translocations, and mutations, especially when present in a sample in low abundance. When the one or more nucleic acid molecules is a double-stranded DNA molecule, the method of the present invention affords the ability to identify at least a portion of monomer nucleotides from both strands of the double-stranded DNA molecule. RNA molecules that can be sequenced using the method of the present invention include, e.g., long non-coding RNA (lncRNA), ribosomal RNA (rRNA), small nuclear RNA (snoRNA), microRNA (miRNA), transfer RNA (tRNA), and small interfering RNA (siRNA)), and RNA/DNA hybrid molecules. The one or more nucleic acid molecules can be isolated from any biological source, including, without limitation, tissue, cells, serum, plasma, blood, or exosomes.

For nucleic acid molecule sequencing, the cleaving enzyme in the bioreactor chamber is an exonuclease or exoribonuclease. Suitable exonucleases and exoribonucleases are described supra. For nucleic acid molecule sequencing, the cleaving enzyme is preferably a processive exonuclease or exoribonuclease that engages the nucleic acid molecule as it enters the bioreactor chamber and sequentially cleaves the nucleic acid molecule into monomer units, i.e., individual nucleotide bases. The cleaved monomer units are electrokinetically transported out of the bioreactor chamber and into and through the time-of-flight channel where they are detected by the sensors and identified based on their flight time through the channel.

As described in more detail in the Examples herein, each nucleotide base, e.g., a deoxynucleotide 5'-monophosphate base, in solution moves through the time-of-flight channel, interacting with the walls of the channel, in a manner that is dependent upon its individual molecular identity, size, and the chemical identity of the surface of the channel (e.g., a neutral, hydrophobic, hydrocarbon surface with different degrees of chain order vs. a charge neutral, hydrophilic surface vs. a charged, hydrophilic surface as described supra). As a result, each mononucleotide base is distinguished based on its transit time through the time-of-flight channel, which is detected and measured by at least two spatially separated sensors of the channel. Since the electrical peak amplitude of each mononucleotide can differ (Tsutsui et al., "Identifying Single Nucleotides by Tunneling Current," *Nat. Nanotech.* 5:286-290 (2010), which is hereby incorporated by reference in its entirety), the electrical peak amplitude of each cleaved mononucleotide as it passes at least one of the sensors can also be measured. This measurement can be used in conjunction with the mononucleotide's flight time to identify the base as it traverses the flight channel.

In another rendition, the single mononucleotides may not interact with the flight tube, but still show molecular dependent time-of-flights. Because the mononucleotides are electrically driven through the flight tube, they can show differences in their electrophoretic mobility, thereby showing a unique time-of-flight that is dependent on the particular mononucleotide without requiring wall interactions. In ether format, the time-of-flight is deduced from the travel time between the pair of sensing electrodes.

In one embodiment of the present invention, the time-of-flight channel has two sensors, e.g., two pairs of nanosensing electrodes, which measure the flight time of the individual nucleotide monomers as they traverse the time-of-flight channel. By way of example only, when the spacing between the two electrodes is 10 μm (microns) and the voltage applied is 10,000 V/cm, the four mononucleotides would have the following average time-of-flight values (based on traditional capillary electrophoresis results):

GMP 242 μs (microseconds)
AMP 246 μs
CMP 254 μs
TMP 266 μs

For each run, a given mononucleotide will have a defined time-of-flight value. Thus, there will be a Gaussian distribution in the time-of-flight values for the individual monomer units of the biopolymer.

In another embodiment, the time-of-flight channel contains three or more sensors, e.g., three or more pairs of nanosensing electrodes, approximately equally spaced along the nanochannel (see FIGS. 6A-6B). When a cleaved biopolymer unit enters the time-of-flight channel, it passes by the first sensor which causes a first electrical signature that can be measured to give a first signal. The first signal occurs at a certain time, and also has a given shape and amplitude. As the biopolymer unit continues to pass through the timeof-flight channel, it passes by the second sensor, and this generates a second electrical signature, which can be measured to give a second signal. The second signal occurs at a certain time, and also has a given shape and amplitude. This process repeats to the third, and up to the nth sensor. In accordance with this embodiment, three signals are obtained and the time-of-flight between each sensors (1, 2 or 1, 3, or 2, 3) can be calculated. This provides three time-of-flight numbers, as well as three independent signal signatures.

The three time-of-flight numbers are dependent on each other, because the time-of-flight between sensors 1 and 3 represents the sum of the time-of-flight between sensors 1 and 2 and sensors 2 and 3. Nevertheless, if the time-of-flight is divided by distance traveled, two independent speeds are obtained, as well as an average speed for each biopolymer unit. For n electrodes, n−1 independent speeds are obtained, and by controlling the number of electrodes the statistical integrity of each average value is controlled. This allows for significantly improving the call accuracy for a given biopolymer unit that enters the time-of-flight nanochannel (reducing the error rate to 0.25%). Further, the additional characteristics of amplitude and shape (rise and fall of signal) provide an opportunity for potentially further verification of biopolymer unit call. For example, if the time-of-flight for AMP and CMP overlap 2% of the time, a three signal signature will aid in further discrimination.

If a biopolymer unit adsorbs to the wall or shows large differences in their electrophoretic mobility, and comes off while another biopolymer unit is in the time-of-flight channel, this may result in a misordering error. However, the use of more than two pairs of sensing electrodes would immediately flag this error. The use of multiple sensing stations will significantly improve the accuracy of base calling. It is not able to correct for errors that might occur prior to entering the time-of-flight channel, such as loss of base, or a misordering error. Such errors may be reduced by sequencing both strands of the double-stranded target DNA, as articulated herein.

The time-of-flight channel may further comprise more than one flight tube coupled together, each flight tube consists of at least two sensors separated by a portion of the time-of-flight channel having a unique wall surface chemistry. Various configurations of coupled time-of-flight tubes within a time-of-flight channel provides multidimensional separations (see FIG. 7). Obtaining flight time measurements of biopolymer units through channels comprising different surface chemistries will enhance discrimination between very similar mononucleotides, e.g., methylated or hydroxymethylated vs. non-methylated bases This process is repeated for each of the sequentially cleaved monomer nucleotide bases to obtain at least a portion of the nucleotide sequence of at least a portion of the one or more nucleic acid molecules in the sample. In some embodiments, the entire nucleotide sequence of at least a portion of the one or more nucleic acid molecules in the sample is obtained. Repeating the applying, detecting, measuring and identifying steps of the method is carried out to obtain at least partial nucleotide sequences of more than one nucleic acid molecule in the sample. In some embodiments, the method is capable of obtaining the entire, or substantially the entire nucleotide sequence of the more than one nucleic acid molecule in the sample.

A problem plaguing some of the currently available sequencing technologies is the inability to accurately detect rare mutational or methylation events, e.g., promoter hypermethylation or hypomethylation or a mutation present at 1% to 0.01% of total DNA. By way of example, consider the presence of circulating tumor DNA in the plasma harboring a mutation in the p53 gene—or anyone of a hundred genes that may be mutated, or a hundred promoter regions that may be methylated in that type of tumor. Such a sample will contain a majority of cell-free DNA arising from normal cells, where the tumor DNA may only comprise 0.01% of the total cell-free DNA. Thus, if one were to attempt to find the presence of such mutant DNA by total sequencing, one would need to sequence 100,000 genomes to identify 10 genomes harboring the mutations. This would require sequencing 300,000 GB of DNA, a task beyond the reach of current sequencing technology, not to mention the enormous data-management issues. To circumvent this problem, many groups have attempted to capture specific target regions or to PCR amplify the regions in question. Sequence capture has suffered from dropout, such that may be 90-95% of the desired sequences are captured, but desired fragments are missing. Alternatively, PCR amplification provides the risk of introducing a rare error that is indistinguishable from a true mutation. Further, PCR loses methylation and hydroxymethylation information. While bisulfite treatment has been traditionally used to determine the presence of promoter methylation, it is also destructive of the DNA sample and lacks the ability to identify multiple methylation changes in cell-free DNA.

While single-molecule sequencing can forgo some of the aforementioned sequencing limitations, a major limitation of traditional single-molecule sequencing is the high error rates associated with most of these techniques. When using exonuclease-based sequencing, one strand is destroyed which prevents sequencing of both strands of a double stranded DNA to verify mutation or methylation status. This is particularly a challenge with lambda exonuclease-based sequencing, which requires a 5' phosphate as well as a double-stranded DNA substrate in order to ensure that only mononucleotides are generated by the nuclease activity in a processive manner. The methods of the present invention described below offer several approaches that allow for direct capture, enrichment, and sequencing of target regions on both strands of a nucleic acid molecule, which provides exquisite proof-reading and confirmation of very low abundance mutations or sequence differences thereby overcoming the above-noted limitations of current sequencing technologies.

Accordingly, another aspect of the present invention is directed to a method for identifying one or more of a plurality of nucleic acid molecules in a sample. In particular, the method allows for identifying one or more sequence differences in the plurality of nucleic acid molecules in the sample. This method involves providing a sample containing one or more nucleic acid molecules each hybridized to its respective complementary nucleic acid molecule, wherein each of the one or more nucleic acid molecules and its hybridized complement thereof comprise a target specific portion and a singled stranded 3' adapter portion suitable for hairpin formation. The sample is subjected to conditions effective for the 3' adapter portions of the one or more nucleic acid molecules and complements thereof to form a hairpin. The method further involves providing a polymerase and blending the one or more 3' hairpinned nucleic acid molecules and complements thereof with the polymerase to form an extension mixture. The one or more nucleic acid molecules and complements thereof are extended from their respective 3' hairpinned regions to form one or more full-length hairpinned nucleic acid molecules. The method further involves sequencing at least a portion of the one or more full-length hairpinned nucleic acid molecules to identify one or more of the one or more nucleic acid molecules in the sample.

In accordance with this aspect of the present invention, the sample provided contains one or more nucleic acid molecules, and complements thereof, containing one or more potential sequence differences to be identified. The nucleic acid molecules in the sample may be randomly fragmented and treated so as to append the adapters (i.e., the 3' adapter portions suitable for hairpin formation) to each end of the fragmented nucleic acid molecules. For example, the ends of a DNA molecule, either blunt ended or made flush, can be phosphorylated using a variety of enzymes, such as T4 polymerase or E. coli polymerase and T4 Kinase. A polymerase without 3' to 5' proofreading activity (such as Klenow (exo)) is used to add an extra "A" to the 3' end, creating a single base 3' overhang. Appending adapter portions to a nucleic acid molecule and complement thereof is achieved using anyone of a variety of enzymatic reactions known in the art. Suitable enzymes include, without limitation, ligases (e.g., E. coli ligase or T4 DNA ligase), polymerases (e.g., Taq polymerase, T4 polymerase, or E. coli polymerase), recombinases, terminal transferases, endonucleases, DNA repair enzymes, and reverse transcriptases.

In accordance with this aspect of the present invention, the 3' adapter portions contain a sequence suitable for hairpin formation. Additionally, the adapter portions may contain one or more unique nucleotide sequence tags, for example, a patient identifying sequence tag and/or a strand identifying sequence tag. Another optional feature is to design the adapters with interspersed random sequences, such that once the adapters are extended and rendered single-stranded, they do not form panhandle structures due to the adapters on each end hybridizing to each other. This also reduces the chance of accidentally destroying an adapter identifier region on one side of the fragment during extension of the 3' hairpinned end if using a polymerase with 5'-3' exonuclease activity.

By way of example only, an adapter portion suitable for use in this aspect of the invention is depicted below. In this example the optional patient identifying sequence is 6 bases, i.e., CGTGAC (allowing for 4,096 different identifier tags) and is underlined. As shown, the patient identifying sequence contains interspersed random nucleotides (i.e., the "N" bases within the patient identification region (CGNTNGNANC; nucleotides 1-10 of SEQ ID NO: 1). The use of 4 "Ns" provides a 256-fold diversity, significantly reducing the chance of having the same adapter sequence on both ends of the fragment. The fragment identification sequence is 10 bases (allowing for 1,048,576 different combinations) and is indicated by the string of boxed Ns. The hairpin sequence is indicated in bold. The shorter oligonucleotide (i.e., SEQ ID NO: 2) contains an extra "T" on the 3' end, such that the adapter is suitable for ligation to A-tailed fragments

```
                                          N
(SEQ ID NO: 1) 5'p CGNTNGNANC NNNNNNNNNN CCGAGC N
(SEQ ID NO: 2) 3'  TGCNANCNTNG5'       3'GGCTCG N
                                          N
```

The oligonucleotide adapters are synthesized with the patient identifier sequence and hairpin sequence defined for each set, but the rest of the bases are added as a mix of all four bases to provide the diversity needed to give each fragment a unique identifier combination.

FIG. 8A is a schematic illustration of this aspect of the present invention. In this example, the adapter portions containing a patient identifier sequence and the hairpinned region are appended to the ends of each DNA fragment (i.e., each of the one or more nucleic acid molecules and complements thereof) in Step 2. The 3' hairpinned ends of the each fragment can be extended using a polymerase that has 5' to 3' exonuclease activity or strand displacement activity (Step 3), thereby dissociating the one or more nucleic acid molecules from their respective complement nucleic acid molecule. Alternatively, the 3' hairpinned nucleic acid molecules can be denatured from their hybridized complement prior to extension by a polymerase enzyme. In this embodiment, a polymerase lacking exonuclease activity or strand displacement activity can be utilized. Following extension of the 3' hairpinned end, the resultant double-stranded hairpinned DNA molecules are ideally suited for sequencing using the device of the present invention.

An alternative approach to appending unique sequence identifiers to both ends of a nucleic acid fragment has recently been developed for "Duplex Sequencing" (Schmitt et al., "Detection of Ultra-Rare Mutations by Next-Generation Sequencing," *Proc Natl Acad Sci USA* 109(36):14508-13 (2012), which is hereby incorporated by reference in its entirety). This method is based on using duplex linkers containing 12 base randomized tags. By amplifying both top and bottom strands of input target DNA, a given fragment obtains a unique identifier (comprised of 12 bases on each end) such that it may be tracked via sequencing. Sequence reads sharing a unique set of tags, are grouped into paired families with members having strand identifiers in either the top-strand or bottom-strand orientation. Each family pair reflects the amplification of one double-stranded DNA fragment. Mutations present in only one or a few family members represent sequencing mistakes or PCR-introduced errors occurring late in amplification. Mutations occurring in many or all members of one family in a pair arise from PCR errors during the first round of amplification such as might occur when copying across sites of mutagenic DNA damage. On the other hand, true mutations present on both strands of a DNA fragment appear in all members of a family pair. Whereas artifactual mutations may co-occur in a family pair with a true mutation, all except those arising during the first round of PCR amplification can be independently identified and discounted when producing an error-corrected single-strand consensus sequence. The sequences obtained from each of the two strands of an individual DNA duplex can then be compared to obtain the duplex consensus sequence, which eliminates remaining errors that occurred during the first round of PCR. The disadvantage of this approach is that many fragments need to be sequenced in order to get at least five members of each strand in a family pair (i.e., minimum of 10 sequence reads per original fragment, but often requiring far more due to fluctuations). Further, the method does not provide information on methylation status of CpG sites within the fragment.

Nevertheless, the above approach for appending unique sequence adapters to the end of targets may be modified for use in the present invention. By way of example only, an alternative adapter portion suitable for use in this aspect of the invention is depicted below. In this example the optional patient identifying sequence is 6 bases, i.e., CGTGAC (allowing for 4,096 different identifier tags) and is underlined. As shown, the patient identifying sequence contains interspersed random nucleotides (i.e., the "N" bases within the patient identification region (CGNTNGNANC; nucleotides 13-22 of SEQ ID NO: 3 below)). The use of 4 "Ns"

provides a 256-fold diversity, significantly reducing the chance of having the same adapter sequence on both ends of the fragment. The fragment identification sequence is 10 bases (allowing for 1,048,576 different combinations) and is indicated by the string of boxed Ns. The hairpin sequence is indicated in bold. The smaller oligonucleotide of the adapter (i.e., SEQ ID NO: 4) contains either a 5'OH or a 5' tail (i.e. TTT, bold) to prevent ligation to the hairpin on the longer adapter strand.

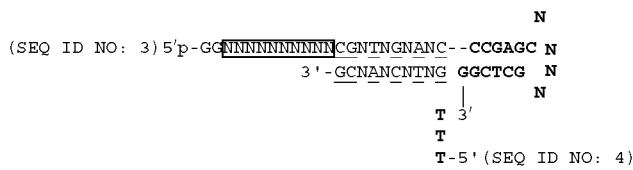

In the examples below, the 3' end of the smaller oligonucleotide of the adapter are extended with a polymerase (i.e. Klenow (exo-)), which lacks exonuclease or strand-displacing activity. Complete adapter A-tailing is ensured by extended incubation with polymerase and dATP.

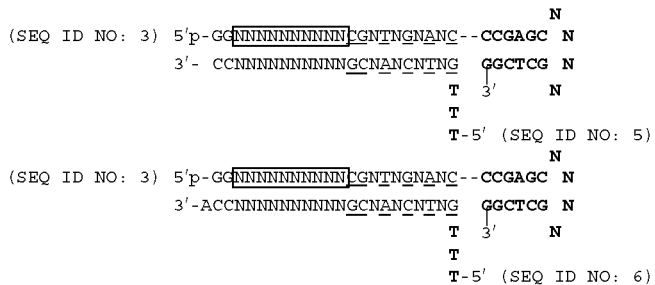

The oligonucleotide adapters are synthesized with the patient identifier sequence and hairpin sequence defined for each set, but the rest of the bases are added as a mix of all four bases to provide the diversity needed to give each fragment a unique identifier combination. Since the above procedure appends an A to the oliogonucleotides, the target DNA will be tailed by a single 3' "T" base on both sides.

FIG. 8B is a schematic illustration of this aspect of the present invention. In this example, the adapter portions containing a patient identifier sequence and the hairpinned region are appended to the ends of each DNA fragments (i.e., the one or more nucleic acid molecules and complements thereof) in Step 2. The 3' hairpinned ends of each fragment are extended using a polymerase that has strand displacement activity (Step 3). The resultant double-stranded hairpinned DNA molecules are ideally suited for sequencing using the device of the present invention. This approach has an advantage over the prior art because (i) it does not require PCR amplification, (ii) it requires sequencing only the original strands from each fragment, not 10 copies, and (iii) since the original strand is sequenced, it preserves CpG methylation information.

The full-length hairpinned double-stranded DNA containing a 5' phosphate is ideally suited for sequencing using the device of the present invention, particularly when a cleaving enzyme such as lambda exonuclease is tethered to the solid support of the bioreactor chamber. The hairpin region provides an opportunity to orient the DNA fragment such that the free (5' phosphorylated) end is the first to encounter the exonuclease. As the DNA is electrophoretically transported through the feeder channel and the entropic trap towards the bioreactor chamber, the end containing the hairpin is impeded in its movement, such that the opposite (free end) moves faster, and thus is first to reach the exonuclease in the bioreactor chamber. In addition, the hairpin sequence can be designed to contain a simple repeat sequence (e.g., $A_n$ or $CA_n$) suitable for transient hybridization to immobilized oligonucleotides containing the complementary sequence (i.e., $T_n$ or $TG_n$) located within the feeder channel, entropic trap, or other chamber upstream of the bioreactor chamber. Because the hairpin region will transiently hybridize to and denature from the immobilized complementary sequence, it will migrate more slowly in the electrophoretic field than the free end, thus aligning the free end to the front of the migration so that it is the first end to reach the bioreactor chamber.

In an alternative embodiment, the hairpin sequence is designed to contain a longer known sequence, suitable for hybridization to an oligonucleotide containing the known complementary sequence. The complementary oligonucleotide is coupled to a "mobility drag" or "mobility modifier". Examples of mobility modifiers that can impede mobility of DNA include, without limitation, peptides, proteins, PEG, other high molecular weight polymers. Under such conditions, after formation of the hairpinned molecule containing the target specific regions of DNA to be identified, the complementary oligonucleotide containing the mobility modifier is appended, e.g., via hybridization, to the hairpinned molecule. The hairpinned end burdened with the hybridized mobility modifier migrates more slowly in the electrophoretic field than the free end, providing an additional energy barrier (besides the entropic trap) for entering the bioreactor channel with the free end preferentially entering first.

In a related aspect of the present invention the method for identifying one or more sequence differences of a plurality of nucleic acid molecules in a sample described above further involves nucleic acid molecule immobilization on a solid support to achieve sequence specific enrichment of one or more desired nucleic acid molecules. This method involves providing a sample containing one or more nucleic acid molecules each hybridized to its respective complementary nucleic acid molecule, wherein each of the one or more nucleic acid molecules and its hybridized complement thereof comprise a target specific portion, a 5' adapter portion, and a 3' adapter portion, wherein each of the 5' and 3' adapter portions are suitable for hairpin formation. The method further involves denaturing the one or more nucleic acid molecules from their complements thereof to form a collection of one or more single-stranded nucleic acid molecules and complements thereof, wherein the hairpin sequences of the 5' and 3' adapter portions of each of the one or more single stranded nucleic acid molecules and complements thereof form hairpins. A solid support is provided that comprises a plurality of immobilized capture oligonucleotide probes, said capture oligonucleotide probes comprising a nucleotide sequence that is complementary to a region of the target specific portion of the one or more nucleic acid molecules or complements thereof. The one or more denatured single stranded nucleic acid molecules and complements thereof are hybridized to their complementary immobilized capture oligonucleotides on the solid support. This method further involves providing a polymerase and contacting the polymerase with the solid support containing the one or more hybridized nucleic acid molecules and complements thereof. The one or more nucleic acid molecules and complements thereof are extended from their respective 3' hairpinned regions to form one or more full-length hairpinned target nucleic acid molecules, thereby causing the one or more nucleic acid molecule to be released from the capture oligonucleotides and from the solid support. At least a portion of the one or more full-length hairpinned nucleic acid molecule is sequenced to identify the one or more nucleic acid molecules in the sample.

FIG. 9 is a schematic illustration of this embodiment of the present invention. In this example, adapter portions containing a patient identifier sequence tag, strand identifier sequence tag, and hairpin region are appended to the ends of a double stranded DNA of interest such that the hairpinned sequence is appended to the 5' end of each fragment (FIG. 9, Step 2). The 3' ends of the double stranded DNA contain a linker region. The 3' linker ends are extended through the hairpin using a polymerase lacking 5' to 3' activity to form double stranded DNA products that contain a target specific portion, a 5' adapter portion, and a 3' adapter portion, where each of the 5' and 3' adapter portions are suitable for hairpin formation as shown in FIG. 9, Step 3. As shown in Step 4 of FIG. 9 the double stranded DNA is denatured into single stranded DNA. Both the sense and antisense DNA strands are captured by hybridization to complementary capture oligonucleotides immobilized on a solid support. Hybridization time on a solid support in a microfabricated device is rapid, on the order of 30-60 seconds, compared to a conventional array (on the order of 3-5 hours) (Wang et al., "Microarrays Assembled in Microfluidic Chips Fabricated From Poly(methyl methacrylate) for the Detection of Low-Abundant DNA Mutations," *Anal. Chem.* 75:1130-1140 (2003), which is hereby incorporated by reference in its entirety). The complementary strands are spatially separated to avoid rehybridization between them.

The hairpin regions of the immobilized single stranded DNAs form hairpins, and the 3' hairpinned ends of the immobilized DNA strands are extended using a polymerase with 5'-3' exonuclease activity or strand displacement activity (Step 5, FIG. 9), which releases the double-stranded hairpinned DNA from the solid support. Alternatively, the immobilized nucleic acid molecules are denatured from their complementary capture oligonucleotides prior to extension. In this case, a polymerase lacking exonuclease or strand displacement activity can be utilized.

Another aspect of the present invention is directed to another approach for identifying one or more of a plurality of target nucleic acid molecules or sequence differences in the plurality of target nucleic acid molecules in a sample that does not involve hairpin formation, yet allows for direct capture and sequencing of target regions on both strands of a nucleic acid molecule. This method involves providing a sample containing one or more nucleic acid molecules each hybridized to its respective complementary nucleic acid molecule, wherein each of the one or more nucleic acid molecules and its hybridized complement thereof comprise a target specific portion, a 5' adapter portion, and a 3' adapter portion comprising a single stranded homopolymer repeat sequence. The method further involves denaturing the one or more nucleic acid molecules from its complement thereof to form a collection of single-stranded nucleic acid molecules and complements thereof. A plurality of oligonucleotide primers that are complementary to the 3' ends of the one or more nucleic acid molecules or complements thereof, and a polymerase are provided, and the one or more nucleic acid molecules and complements thereof are blended with the polymerase and primers to form an extension mixture. The method further involves hybridizing the oligonucleotide primers to their complementary 3' ends of the one or more nucleic acid molecule and complements thereof, and extending the hybridized primers to form full-length double stranded nucleic acid molecules. At least a portion of the one or more full-length double stranded nucleic acid molecules is sequenced to identify the one or more nucleic acid molecules in the sample.

FIG. 10 is a schematic illustration of this aspect of the present invention. As shown, double stranded genomic DNA is an exemplary nucleic acid molecule that can be identified using this method. The genomic DNA is randomly fragmented and treated so as to append the adapters to each end of the molecule (FIG. 10, Step 2). For example, the ends of the DNA, either blunt ended or made flush are phosphorylated as described above, and a polymerase is used to add an extra "A" to the 3' end, creating a single base 3' overhang. The adapter portions, containing, e.g., strand identifier sequences or tags, are appended to each end of the DNA fragment (FIG. 10, Step 2). The 3' adapter ends are extended using a polymerase and then tailed with a terminal transferase (FIG. 10, Step 3). Tailing is used to introduce a homopolymer repeat sequence, such as a polyA tail, to the end of the 3' adapter portion.

The double stranded DNA is denatured and primers are hybridized to the 3' ends of the tailed adapter strands (FIG. 10, Step 4). The hybridized primers are extended using a polymerase to generate a double-stranded DNA that is ideally suited for sequencing using the device of the present invention. The sequenced strand contains a strand identifier sequence on both ends, allowing unique verification of its origin. In addition, since the original genomic strand is sequenced, all base modifications are preserved.

To achieve target specific enrichment of a particular DNA fragment, a variation of the method described above can be employed that involves selective target-sequence specific capture on a solid support. A schematic illustration of this embodiment is shown in FIG. 11. Adapter portions are appended to each end of the DNA fragment as described above (FIG. 11, Step 2). In this example, the adapter portions also contain a patient identifier sequence tag. The 3' adapter ends are extended with a polymerase and tailed using a transferase as described above (FIG. 11, Step 3). The double stranded DNA is denatured into single stranded DNA. Both the upper and lower target strands are captured by hybridization to complementary oligonucleotide probes immobilized to a solid support (FIG. 11, Step 4). The complementary strands are spatially separated so that neither they nor the target strands will rehybridize to each other.

Oligonucleotide primers are hybridized to the 3' ends of the immobilized single stranded DNA, and extended using a polymerase to generate double-stranded DNA molecules that are ideally suited for sequencing (FIG. 11, step 5). In one embodiment of the present invention, the single stranded DNA immobilized to the solid support is denatured from its complementary capture probe prior to primer extension. Alternatively, the single stranded immobilized DNA is liberated during primer extension by using a strand-displacement polymerase (leaving the complementary capture strands intact), or using a polymerase with 5'->3' exonuclease activity (that digests away the complementary capture strands).

The oligonucleotide primers utilized in this aspect of the present invention overlap with the known sequence of the strand identifier portion as well as the homopolymer repeat sequence of the adapter segments. The primers do not have a 5' phosphate and are recessed relative to the 3' end of the homopolymer repeat sequence, thus this end is not a substrate for a cleaving enzyme like lambda exonuclease when the generated full-length double stranded DNA is sequenced using the device of the present invention.

In accordance with this aspect of the present invention, the 3' single-stranded homopolymer repeat (e.g., $A_n$) provides an opportunity to orient the fragment within the biomolecular processor of the present invention such that the blunt (5' phosphorylated) end will be first to encounter the cleaving enzyme, i.e., an exonuclease. As the DNA is electrophoretically transported through the feeder channel and the entropic trap towards the bioreactor chamber, the end containing the 3' single-stranded homopolymer repeat is impeded in its movement, such that the free end has a higher probability of entering the bioreactor chamber first and encountering the exonuclease. A complementary homopolymer sequence (i.e., $T_n$) can be immobilized within the feeder channel or entropic trap such that the 3' single-stranded homopolymer repeat will transiently hybridize to and denature from it causing the 3' single stranded end to migrate more slowly in the electrophoretic field than the free end. Alternatively, a longer oligonucleotide that is complementary to the 3' single-stranded homopolymer repeat and also contains an attachment that serves as a mobility drag in an electrical field may be used as described above to slow the migration of the 3'end.

Appending adapters containing the sequence design described above provides an excess capacity to uniquely identify each nucleic acid fragment based on: (i) the random fragment ID sequence on the 5' side; (ii) the patient ID sequence on the 5' side; (iii) the junction site on the 5' side of the target sequence; (iv) the sequence of the captured target; (v) the junction site on the 3' side of the target sequence; (vi) the patient ID sequence on the 3' side; and (vii) the random fragment ID sequence on the 3' side. The two random sequences (assuming 10 bases each) alone provide in excess of $1\times10^{12}$ degree of diversity, sufficient to uniquely distinguish target DNA from 100,000 genome equivalents. Thus, a true mutation will be verified by identifying the same mutant base on both the top and bottom strand of the same sequence. Likewise a true 5-methyl-dC or 5-hydroxymethyl-dC at a given CpG dinucleotide will be manifest as presence of 5-methyl-dCMP or 5-hydroxymethyl-dCMP base call on both the top and bottom strand of a given CpG dinucleotide.

A high consensus accuracy can be achieved in the presence of high error rates by sequencing the same region of DNA over and over again. However, a high error rate makes it extremely difficult to identify a sequence variant in low abundance, for example when trying to identify a cancer mutation in the presence of normal DNA. Therefore, a low error rate is required to detect a mutation in relatively low abundance.

The device and methods of the present invention afford a number of approaches to achieve the low error rate required to accurately detect low abundance mutations, i.e., the method of the present invention is capable of distinguishing low abundance nucleic acid molecules, e.g., RNA and DNA, containing one or more nucleotide base insertions, deletions, translocations, mutations, or damaged bases from a 100-fold to 10,000-fold or greater excess of nucleic acid molecules in the sample having a similar nucleotide sequence as the low abundance nucleic acid molecule but without the corresponding one or more nucleotide base insertions, deletions, translocations, mutations and/or damaged bases. For example, in one approach Lambda exonuclease is utilized as the cleavage enzyme to digest the 5' end of dsDNA, where both strands contain unique sequence identifiers (adapters as described above) so they may be identified as arising from the same original target DNA. In this approach, the error rate for sequencing both strands is substantially lower than for just one strand, since the probability of a mis-call on one strand matching the complementary mis-call at the same position on the other strand is 4-fold lower, than just any mis-call. The error and accuracy rates are shown in Table 1 below. Note that this approach holds independent of which enzyme is used to generate the mononucleotides. For example, after appending appropriate adapter to add a unique sequence identifier to both ends of a double-strand DNA from the sample, the DNA may be denatured and rendered single stranded, suitable for digestion from the 3' ends with Exonuclease I, and the appropriate mate strands identified by their unique sequence identifiers.

TABLE 1

Lambda Exonuclease Digestion of dsDNA containing Strand Identifiers and Analysis of Both Strands

| Error Rate SS seq | Accuracy | Error Rate DS seq | Accuracy |
| --- | --- | --- | --- |
| 10.0% | 90.0% | 0.2500% | 99.7500% |
| 4.0% | 96.0% | 0.0400% | 99.9600% |
| 1.0% | 99.0% | 0.0025% | 99.9975% |
| 0.5% | 99.5% | 0.0006% | 99.9994% |
| 0.2% | 99.8% | 0.0001% | 99.9999% |

Another approach involves the use of Lambda exonuclease to digest the 5' end of dsDNA, followed by Exonuclease I to digest the resultant single-stranded DNA from the 3' end. In accordance with this embodiment, the resultant single-stranded DNA would be introduced into a second feeder channel leading to a second bioreactor chamber containing Exonuclease I. The digested mononucleotides would be shuttled through a second time-of-flight channel to separate and identify nucleotides released by the second digestion. The calculations below assume that error rates in distinguishing the nucleotides in the time-of-flight channel do not different, even though generated by different exonucleases.

TABLE 2

Coupled Lambda Exonuclease/Exonuclease I Digestion of First and Second Strands of a dsDNA Target Molecule

| Error Rate SS seq | Accuracy | Error Rate DS seq | Accuracy |
| --- | --- | --- | --- |
| 10.0% | 90.0% | 0.2500% | 99.7500% |
| 4.0% | 96.0% | 0.0400% | 99.9600% |
| 1.0% | 99.0% | 0.0025% | 99.9975% |
| 0.5% | 99.5% | 0.0006% | 99.9994% |
| 0.2% | 99.8% | 0.0001% | 99.9999% |

Another approach involves Lambda exonuclease digestion of dsDNA, with use of single sensing (two nanoelectrode pairs to obtain a single time-of-flight measurement) compared with double sensing (three nanoelectrode pairs to obtain three time-of-flight measurements). In this case, the comparison is between the same potential error rates for the same nucleotide being cleaved off only one strand. Thus the error rate is slightly higher than the approaches above where both strands of the same original target molecule are interrogated.

TABLE 3

Lambda Exonuclease Digestion of dsDNA, Comparing Single and Double Flight Time Measurements

| Error Rate Single Sensing | Accuracy | Error Rate Double Sensing | Accuracy |
| --- | --- | --- | --- |
| 10.0% | 90.0% | 1.0000% | 99.0000% |
| 4.0% | 96.0% | 0.1600% | 99.8400% |
| 1.0% | 99.0% | 0.0100% | 99.9900% |
| 0.5% | 99.5% | 0.0025% | 99.9975% |
| 0.2% | 99.8% | 0.0004% | 99.9996% |

Distinguishing methylated or hydroxymethylated bases from their unmethylated counterparts (i.e., d5meCMP vs. dCMP) may be more difficult than simply distinguishing two natural bases from each other. Consequently the classification error rate for distinguishing d5meCMP from dCMP may be higher. Shown in Table 4 below are the calculated error rates for distinguishing methylated and unmethylated C bases.

TABLE 4

Methylation, Single Sensing Compared with Double Sensing

| Error Rate Single Sensing | Accuracy | Error Rate Double Sensing | Accuracy |
| --- | --- | --- | --- |
| 20.0% | 80.0% | 4.0000% | 96.0000% |
| 10.0% | 90.0% | 1.0000% | 99.0000% |
| 5.0% | 95.0% | 0.2500% | 99.7500% |
| 2.0% | 98.0% | 0.0400% | 99.9600% |
| 1.0% | 99.0% | 0.0100% | 99.9900% |

Biologically relevant methylation often occurs in regions known as CpG Islands, which are high in G+C content, as well as adjacent regions, known as CpG shores. Thus, using cues such as a CpG sequence, and scoring for methylation status of adjacent CpG sequences dramatically improves the accuracy in scoring 5 meC, even with high error rates for distinguishing d5meCMP from dCMP in a single time-of-flight measurement. This is illustrated in Table 5 below:

TABLE 5

Methylation, Single Sensing Compared with Double Sensing, and Scoring for Consecutively Methylated CpG Sequencing

| Error Rate Single Sensing | Accuracy | Error Rate Dble-Consec. | Accuracy |
| --- | --- | --- | --- |
| 20.0% | 80.0% | 0.1600% | 99.8400% |
| 10.0% | 90.0% | 0.0100% | 99.9900% |
| 5.0% | 95.0% | 0.0006% | 99.9994% |

Likewise, combining double sensing with determining the sequence of both strands, as outline above will also significantly lower error rate and improve the accuracy of calling methylation status in various promoter regions. Accordingly, the method of the present invention is capable of distinguishing low abundance nucleic acid molecules with one or more unmethylated or unmodified nucleotide bases from a 100 to 10,000-fold or greater excess of nucleic acid molecules in the sample having a similar nucleotide sequence as the low abundance nucleic acid molecule with methylated or modified nucleotide bases. Likewise, the method of the present invention is capable of distinguishing low abundance nucleic acid molecules with one or more methylated or modified nucleotide bases from a 100-fold to 10,000-fold or greater excess of nucleic acid molecules in the sample having a similar nucleotide sequence as the low abundance nucleic acid molecule with unmethylated or unmodified nucleotide bases.

The device and methods described herein will overcome the above noted problems plaguing currently available sequencing technologies. The device and methods of the present invention can identify the presence of one or more mutations in 100 genes or one or more methylation changes in 100 promoters arising from tumor DNA in cell-free DNA in the plasma, where the tumor DNA containing mutational or methylation changes represents 10 genomes in 100,000 genomes of normal DNA. Consider that the average gene represents 2,000 bases of sequence, and the average promoter region 500 bases, then capture probes (average length of 50 bases) will be synthesized to capture 250,000 bases of unique sequence. That represents 5,000 probes to capture "top" strand sequence and 5,000 probes to capture "bottom" strand sequence. Each set of 5,000 probes may be synthesized in bulk (or on an Agilent chip and cleaved from the chip), and then attached to spatially separated regions of the microfabricated device, for example on pillars or other high-aspect ratio features in that region of the chip used for oligonucleotide attachment.

As a patient becomes older, some genes are sporadically turned off as a result of age-related promoter methylation. When a tumor expands, it often exhibits a global hypomethylation and specific hypermethylation at specific promoter regions. Both of these changes in methylation status provide an opportunity for early detection of cancer-specific DNA in the plasma. It is important to identify multiple loci with cancer-specific methylation changes to avoid a spurious false positive due to age-related changes. The device and methods described herein provide a rapid way to identify methylation changes in tumor tissue, as well as a highly accurate method for identifying low-abundance changes in plasma or other biological samples.

The methods and device of the present invention provide a number of advantages over previous methods and devices for nucleic acid molecule sequencing. In particular, the methods of the present invention achieve long read lengths (200 to 50,000 bases) with a high level of accuracy from first to last base, uniform coverage and fast throughput at a low cost per run. The device can sequence 250,000 bases on both strands (=500,000 bases) in the 100,000 genome equivalents. That is equal to $5\times10^{10}$=50 GB of DNA sequence. At the maximum capacity of 500 GB of DNA in a single 1.4 hour run, the device of the present invention can evaluate 10 serum samples simultaneously, to provide a comprehensive evaluation of the mutational status of 100 cancer genes and 100 promoter regions whose methylation status correlates with cancer or outcome status. If there were a screening test, of only 20 genes and 20 promoter regions, then 50 serum samples would easily be evaluated in a single run.

Sequencing reads obtained using the device and methods of the present invention do not have the context-specific errors that plague other sequencing technologies (e.g., high GC; homopolymer stretches). The ability to achieve single molecule resolution facilitates characterization of heterogeneous samples and enables identification of variation that can be invisible to other sequencing technologies. Direct capture and sequencing of target regions on both strands provides exquisite proof-reading, and confirmation of very low abundance mutations. The ability to sequence long stretches of nucleotide sequences can resolve SNPs, haplotype, and large scale structural rearrangements with high sensitivity and specificity. Long reads also simplify and improve genomic assembly by reducing the number of contigs and producing better consensus accuracy compared to shorter read sequencing technologies at the same depth of coverage. Finally, direct sequencing of input DNA without amplification enables identification of original base modification (e.g., 5-methyl-C, 5-hydroxy-methyl-C, or damaged DNA bases) without bisulfite conversion. As opposed to existing single-molecule DNA sequencing strategies, the present device has the capability to generate highly accurate calls on the natural and unnatural bases in a single sequencing run due to flight-time identification protocol as well as unique electrical signatures generated by each monomer unit.

The device and methods of the present invention provide a low cost sequencing platform that will enable clinical research and diagnostic tests that are impractical or impossible with other available sequencing instruments. For example, sequencing nucleic acid molecules isolated from blood (e.g., from plasma, exosome, or circulating tumor cells) will provide (i) accurate identification of various genetically-related diseases (e.g., cancer) by high sensitivity detection of promoter hypermethylation and hypomethylation (when present at 1% to 0.01% of cell-free DNA), (ii) accurate identification of genetically-related diseases by high sensitivity detection of single base mutations, small insertions, and small deletions in known genes (when present at 1% to 0.01% of cell-free DNA), (iii) accurate identification of early disease onset by quantification of specific mRNA and miRNA isolated from blood, (iv) accurate identification of specific copy changes in DNA, and (v) accurate identification of early disease by quantification of mutations, promoter hypermethylation and hypomethylation in DNA isolated from particular circulating disease related cells.

The biomolecular processing device and methods of the present invention are particularly well suited for carrying out a variety of diagnostic assays. In particular, the biomolecular processing device and methods of the present invention are well suited for carrying out prenatal diagnostic assays using a maternal serum sample. Recent work has shown that fetal DNA as a percentage of maternal DNA in the serum is at approximately 6%, 20%, and 26% in the $1^{st}$, $2^{nd}$, and $3^{rd}$ trimester, respectively. Due to how DNA is degraded, maternal DNA is usually about 160 bases and still associated with the H1 histone, while fetal DNA is about 140 bases and not associated with histone. Depending on the clinical need, and where the knowledge will provide the best care, tests may be developed with sufficient sensitivity to detect fetal DNA in the appropriate trimester.

There are approximately 3,500 recessive genetic disorders where the gene is known. The most common disorders result from DNA copy anomalies, either an extra chromosome such as in Trisomy 21, or deletion of a portion of a gene, such as in the Duchenne muscular dystrophy (DMD) gene. In considering prenatal screening, one needs to balance the probability of a genetic disorder vs. the risk of the procedure. Currently, the standard of care recommends amniocentesis during week 17 for expectant mothers at age 35, since the risk of Trisomy 21 or other chromosomal aneuploidy at 1 in 200 now matches the risk of spontaneous abortion after the procedure.

In considering the use of the methods of nucleic acid sequencing described herein for prenatal screening, two levels of testing are recommended. For low-cost screening of all pregnancies for Trisomy 21, 13, and 18, the sequencing methods of the present invention may be used to rapidly identify differentially expressed genes on chromosomes 21, 13, and 18, e.g., identify those genes that are turned off in the fetus as a consequence of methylation silencing, but are on in the adult. Similar regions are identified on three control chromosomes, i.e., chromosomes 2, 5, 7. Even when isolating DNA from the serum of a mother in the first trimester, one can rapidly calculate the percentage of DNA arising from the fetus by comparing methylated to unmethylated DNA among control chromosomal regions—in the example herein, that would be 6%. If there is trisomy at any of the other chromosomes, i.e. Trisomy 21, then the promoters from that chromosome will show methylation at about 9%, in other words, some 50% higher than for the normal disomy case. Scoring 1,000 genome equivalents is recommended, such that a count of 90 methylated copies for the trisomy case is easily distinguished from 60 methylated copies for the normal sample. Consider that 10 promoter regions are interrogated×6 chromosomes×500 bases×2 strands×1,000 copies=60 MB of DNA sequence per sample. At the maximum capacity of 500 GB of DNA in a single 1.4 hour run, the device of the present invention is able to evaluate approximately 8,300 serum samples simultaneously.

To determine if the fetus contains an inherited or sporadic mutation associated with the roughly 3,500 other disorders, including deletions, point mutations, or abnormal methylation, a more sophisticated analysis would be recommended. Sequence analysis readily determines presence of the recessive allele in both parents. If the mutation is different in the parents, it is possible to determine if the child is a compound heterozygote for the disease by evaluating cell-free DNA from the maternal serum. Obtaining the full answer from analysis of fetal DNA in the maternal serum may require a two part assay. The first is to establish phase for the maternal SNPs or polymorphisms in repeat regions that surround the disease gene. This may be accomplished by isolating high molecular weight DNA from white blood cells of the mother, or from saliva of the father. Since the nucleic acid sequencing methods of the present invention are capable of sequencing long stretches of DNA, this may be used to establish neighboring SNPs or polymorphisms in repeat regions associated with the disease gene as well as chromosomal phase (haplotype). It will also establish if there are deletions, e.g., the mother is a carrier for a deletion in the DMD gene.

At 17 weeks, the time that an amniocentesis would be considered, the mother is already in the second trimester, i.e., fetal DNA is present in the 15%-20% range. In a first approach, at the maximum capacity of 1,000 GB of DNA in a single 2.8 hour run, the device of the present invention would evaluate 330 genome equivalents, and if 15% of that originates from the fetus, that is about 50 genomes, or coverage of about 25 of each haplotype. This approach is the most comprehensive and will be able to detect genetic diseases arising from both inherited changes as well as those that are de novo changes in the fetus. This approach will detect not only DMD deletions, but also other small copy number anomalies, such as those responsible for autism. About 1 in every 200 pregnancies results in a balanced translocation, and this approach can accurately determine the junction position, to determine potential clinical manifestations. Further, this approach will be able to accurately quantify methylation changes, which may result in diseases associated with imprinting, such as Angelman's syndrome or Prader-Willi syndrome. The ability of the present invention to determine methylation status and at the same time to determine if the deletion is on the paternal or maternal chromosome by SNP detection (i.e., detection of upstream or downstream cis-located maternal or paternal identifying SNPs) will enhance its diagnostic discrimination of imprinting diseases. Finally, because the method described herein does not require either cloning or PCR amplification, triplet repeat changes, responsible for diseases such as Huntington's disease and Fragile X syndrome may be properly scored. The ability of the present invention to also perform protein and polypeptide identification and quantitative proteomics as described below will allow it to be used in the measurement of fetal proteins in maternal serum is a part of prenatal screening for fetal aneuploidy and neural tube defects.

Alternatively, in a second approach, the disease genes may be divided into the 20 most common inherited diseases, and then divided into 17 groups of less commonly mutated sequences covering an average of 200 genes each. Each group of genes would be covered by sets of capture probes for both strands, and then depending on the results from the parental sequencing analysis, the maternal blood would be given proper patient identifiers and evaluated on one or more of the 17 specialty chips. If on average a given gene is about 2,500 bases in length, then for 200 genes, for both strands is 1 MB of capturing probes on the chip. If 1,000 genome equivalents are to be sequenced, then one serum sample will require 1 GB of sequence. At the maximum capacity of 500 GB of DNA in a single 1.4 hour run, the device would evaluate 500 serum samples in a single run.

The first of the above approaches will identify both inherited and sporadic mutations, as well as determine if the fetus inherited a mutation-bearing region from the mother. This approach should also be able to determine the presence of deletions for x-linked inherited diseases, other chromosomal deletions, aberrant methylation in the fetus, diseases arising from triplet repeats, and diseases arising from chromosomal translocations or other rearrangements.

The second approach will identify disease conditions for the genes interrogated. The key issue will be how important is it for the family to get the right answer. It is straightforward to determine if both parents are carriers, and if the mutations are different, relatively straightforward to determine if the father's disease allele is present in the fetus. If it is absent, then the fetus will be either disease free or a carrier. If it is present, then the chances of inheriting the maternal allele and getting the disease are 50%. If haplotype for the maternal allele has been determined, then haplotype markers may be used to verify presence or absence of the inherited maternal allele. It may also be prudent to do an amniocentesis and directly test for the presence of the maternal allele. The current recommendation is to sequence the gene as outlined above, and score for the paternal disease allele. If present, or if the paternal and maternal disease-specific mutations are identical, then the physician recommends amniocentesis.

The methods and device of the present invention can achieve long read lengths making it ideal for non-invasive prenatal diagnosis and preimplantation genetic diagnosis (PGD) of chromosomal translocations. Individuals that carry chromosomal translocations are at increased risk for infertility, miscarriage, stillbirth, and/or having a child with birth defects. Preimplantation genetic diagnosis is able to distinguish between embryos that have the correct amount of genetic material (balanced/normal) and embryos that are missing genetic material as a result of the translocation (unbalanced). Many couples in which one member is a translocation carrier have experienced miscarriages or have had to face difficult decisions when learning about a pregnancy with an unbalanced set of chromosomes. The methods and device of the present invention based PGD would reduce the likelihood of having to deal with these particular circumstances by knowing prior to conception that the embryo(s) transferred have balanced chromosomal translocations.

Sequencing both strands of input double-stranded DNA allows for the highest level of accuracy in base calling. RNA substrates, by nature of their single-strandedness, do not provide the opportunity to interrogate both strands. However, in most cases, the fully correct RNA sequence can be inferred from the genomic sequence—which in turn may be determined by sequencing both strands of the same input fragment, providing the highest accuracy. Thus, RNA sequencing can provide critically important information such as literally counting each and every messenger RNA, including all splice-site variants, all long non-coding RNA (lncRNA) molecules, all microRNA (miRNA) molecules present in a sample—be it from circulating tumor cells or cancer-specific exosomes isolated from serum. Thus, sequencing single-stranded RNA substrates does not demand the same high fidelity as double-stranded DNA substrates, but because the readout is still based on the time-of-flight channel detection, the ability to quantify unusual or modified bases in the RNA is retained.

The device of the present invention presents advantages over other technology in sequencing all mRNA. Current microarray technology can identify expression of different exons in a transcript, but lacks the ability to accurately determine or quantify all the splice-site variants. The current next-generation quantification of mRNA generates representations on the 3' end and sequences short fragments of cDNA, which are then used to count the number of copies of each mRNA species. In contrast, the current embodiment described herein allows for sequencing the entire original mRNA strand, independent if it is 14,000 bases or 400 bases. This method allows the device to determine both normal splicing and aberrant splicing in cancer cells, with the potential to identify tumor-specific targets of therapy.

The ability to distinguish RNA modifications using the methods and device of the present invention, which is not readily done by existing technologies, will help revolutionize our understanding of gene expression and disease causation. Recent studies have shown that up to 20 percent of human mRNA is routinely methylated. Moreover, it has recently been shown that defects in RNA methylation can lead to disease. For example, the fat mass and obesity-associated (FTO) gene encodes an enzyme capable of reversing RNA methylation. FTO mutations can cause abnormalities in food intake and metabolism that lead to obesity. FTO mutations are a leading cause of obesity and type 2 diabetes. There is recent evidence that RNA modifications may also play a role in cancer and in neurological disorders such as autism, Alzheimer's disease, and schizophrenia.

Another aspect of the present invention relates to a method for identifying one or more proteins or polypeptides in a sample using the device of the present invention. This method involves feeding a sample comprising one or more proteins or polypeptides into the biomolecular processor of the device under conditions effective for the immobilized cleaving enzyme within the bioreactor chamber to engage the one or more proteins or polypeptides in the sample and to cleave the one or more proteins or polypeptides into smaller peptide fragments that enter the input end of the one or more time-of-flight channels. An electric field is applied across the one or more bioreactor chambers and along the length of the one or more time-of-flight channels to transport the cleaved peptide fragments through the one or more time-of-flight channels, and, based on the applied electric field, the peptide fragments are detected as they pass at least the first and second sensors in the one or more time-of-flight channels. The method further involves measuring, based on the detecting, (i) how long it takes for each peptide fragment to pass at least the first and second sensors of the one or more time-of-flight channels, and/or (ii) electrical peak amplitude of each peptide fragment as it passes at least one of the first or second sensors in the one or more time-of-flight channels. At least a portion of the one or more proteins or polypeptides in the sample is identified based on the measured peptide fragments.

In accordance with this aspect of the present invention, the measurements obtained for the cleaved peptide fragments (i.e., the flight time and electrical peak amplitude of each peptide fragment) are compared to a database containing the corresponding measurements of peptide fragments generated by cleavage of known proteins or polypeptides to identify or characterize the one or more unknown proteins or polypeptides in a sample.

The human genome has identified about 21,000 protein coding genes, and with alternative splicing these yield about 100,000 different cellular proteins. The vast majority of these proteins undergo post-translational modifications such as phosphorylation, acetylation, and methylation, and such modifications often play a critical role in the function and active state of the protein.

In one embodiment of this aspect of the invention, the complexity of the analysis can be reduced by adding an initial step to fractionate or enrich the desired proteins from a sample containing a plurality of proteins. This fractionation step is easily added by integrating discrete modules into the device of the present invention that using a modular integration approach. This fractionation step may be dependent on a physical property, such as separation by size, charge, or hydrophobicity, using for example chromatography. The fractionation may also depend on affinity to an antibody, a small molecule, or a macromolecule. For example an antibody enrichment step, or isolating the proteins associated with a given transcription factor (also pulled down by specific antibodies). Alternatively, proteins may be enriched for by binding to one or more of a family of phosphorylated, methylated, or acetylated peptides, or other protein domains, or methylated DNA, or specific DNA sequences, or a family of DNA sequences, or common substrates such as ATP or GTP or their analogues, and may be fractionated by affinity purification on a solid support containing covalently attached substrates or their analogues. Other approaches to fractionate the input proteins include separation by subcellular compartment such as nucleus, cytoplasm, mitochondria, endoplasmic reticulum, golgi, cell membrane, nuclear membrane, lysozome, or association with DNA, RNA, chromatin, other protein scaffolds. Fractionation may be designed to enrich for a group of proteins including, but not limited to: G-protein coupled receptors, nuclear receptors, voltage gated ion channels, ligand gated ion channels, receptor tyrosine kinases, growth factors, proteases, sequence specific proteases, phosphatases, protein kinases, bioactive lipids, cytokines, chemokines, ubiquitin ligases, viral regulators, cell division proteins, scaffold proteins, DNA repair proteins, bacterial ribosomes, histone deacetylases, apoptosis regulators, chaperone proteins, serine/threonine protein kinases, cyclin dependent kinases, growth factor receptors, proteasome, signaling protein complexes, protein/nucleic acid transporters, and viral capsids As individual proteins are fed into the bioreactor chamber, the immobilized cleaving enzyme, i.e., a protease, digests the protein to completion, and the fragments are separated and detected in one or more time-of-flight nanochannels using either capillary electrophoresis or capillary electrochromatography. This separation and detection creates a fingerprint for that given protein. If a certain residue is modified, e.g., a lysine is acetylated, the mobility of that fragment will be modified compared to the same fragment containing a non-acetylated lysine. Alternatively, the acetylation may prevent enzyme cleavage at that position that would normally occur (e.g., trypsin will not cleave at an acetylated residue), changing the peptide fingerprint. Using a database containing measurements or fingerprints of peptide fragments cleaved from known proteins with known modifications, one can compare the pattern acquired for the unknown proteins/polypeptides in a sample to the database to identify and characterize the proteins/polypeptides in the sample. The unique aspect of this embodiment is that it is performed at the single molecule level, therefore, rare modifications can be observed that are not manifested using conventional protein processing protocols that utilize many different forms of mass spectrometry.

The utilization of one or more time-of-flight nanochannels with two or more sensing electrode pairs and/or two or more flight tubes having different wall surface chemistries to generate one or more flight time measurements per channel, creates a very sophisticated fingerprint, for example a 2-dimensional, 3-dimensional, or 4-dimensional fingerprint to distinguish essentially all possible proteins and their modifications. An example of device architecture for generating n-dimensional fingerprints with two or more flight tubes having different wall surface chemistries is provided in FIG. 7. Modifications include, but are not limited to, methylation, acetylation, phosphorylation, glycosylation and any other post translational modification of one or more amino acid residues of threonine or tyrosine.

For the protein fingerprinting to be effective in distinguishing individual proteins, the protease needs to generate the same fragments the vast majority of the time—i.e. it needs to demonstrate specific cleavage. The easiest way to achieve this is to use proteases that require a specific type of residue in the recognition pocket. Particular proteases that are suitable for use in the present invention are described supra.

Protein/polypeptide analysis using the methods and device of the present invention can be used to accurately identify, i.e., diagnose and prognose, diseases arising from changes in protein levels or covalent modifications of a protein in a sample enriched from a subcellular component, for proteins associated with cellular DNA, RNA, chromatin, or other protein scaffolds, for proteins that bind a substrate or its analogue, or for proteins that bind to macromolecules such proteins, carbohydrates, lipids, methylated DNA, specific DNA sequences, or a family of DNA sequences.

The use of the device of the present invention for protein analysis will play a crucial role in advancing knowledge and understanding in a wide variety of health related research arenas, including studies of reproduction and longevity mechanisms, pathogenic bacteria, infertility, cancer transformation, diabetes, age-related diseases, Crohn's disease, Alzheimer's disease, insulin resistance, pathogenic fungal progression, and prostate cancer prognosis. The present invention will also be central to the success of shotgun quantitative proteomics to maximize protein sequence coverage, accurate quantitation and high confidence identification for low abundance proteins in complex samples. The methods of the present invention will provide accurate quantitation of protein complexes and sensitive measurement of the dynamic modulation of protein modifications within different tissues, cells and organelles where often proteins and complexes of interest are of very low abundance and within a low dynamic range.

The methods and device of the present invention can be used to detect serum markers to distinguish benign from malignant prostatic disease. Prostate cancer (CaP) is the most common noncutaneous malignancy in men. The introduction of prostate-specific antigen (PSA) screening has decreased mortality significantly but the use of PSA as a diagnostic serum marker is far from perfect. The present invention can be used for the detection of additional serum markers that predict the presence and progression of CaP and differentiate benign from malignant disease with high sensitivity and specificity. In particular, the present invention can be used for the detection of prostate specific biomarkers that are detectable in an easily accessible biological fluid and distinguish between normal, benign prostatic hyperplasia (BPH), prostatic intraepithelial neoplasia and cancerous prostate tissues. Serum biomarkers that display altered expression between benign and malignant disease and have the potential to supplement or fulfill the role of PSA include thrombospondin-1 (TSP-1), engrailed-2 (EN2), BCL-2, Ki-67, ERK5, chromogranin-A (CgA), human glandular kallikrein 2 (hK2), urokinase-type plasminogen activator (u-PA), transforming growth factor-31 (TGF-β1), interleukin-6 (IL-6), prostate membrane-specific antigen, prostate-specific cell antigen, α-methylacyl-CoA racemase (AMACR) autoantibodies, early prostate cancer antigen (EPCA), GSTP1 hypermethylation, sex hormones and sex hormone-binding globulin (SHBG). For instance, EPCA and hK2 are possible diagnostic factors and CgA, IL-6 and TGF-3 are possible prognostic predictors. No single marker is likely to achieve the desired level of sensitivity and specificity. A combination of markers or serum profile will improve the diagnostic accuracy of CaP screening as well as the prognostic accuracy for improving treatment. The high sensitivity and high sampling rate of the method and device of the present invention make it ideal for this multi-factor diagnostic and prognostic approach. Use of the present invention for the detection and identification of blood protein markers that provide accurate or early diagnosis of prostate cancer has the potential to reduce the number of unnecessary prostatic biopsies and to significantly improve prostate cancer treatment and management.

The methods and device of the present invention can be used to identify N-glycosylated protein sites in different tissues of patients with Alzheimer's disease. N-linked glycosylation is the attachment of oligosaccharides to a nitrogen atom, usually the N4 of asparagine residues, and occurs on secreted or membrane bound proteins. A direct link between site-specific glycosylation and Alzheimer's disease has been made, through Preselinin-1, a protein that is part of the gamma secretase protein complex, which is one of the proteases involved in processing amyloid precursor protein (APP) to the short Alzheimer's disease-associated peptide amyloid beta. The methods of the present invention can be used to build on discoveries that N-glycosylated sites on proteins may play an important role in Alzheimer's disease and thus further understanding and improve diagnosis and prognosis of the disease.

Currently, diagnosis of chronic liver disorder requires a liver biopsy to assess fibrosis stage and necroinflammatory activity and to detect cirrhosis. In a large subgroup of these patients, cirrhosis is a major risk factor for the development of hepatocellular carcinoma. There is therefore a demand for serum markers that can routinely assess progression of liver fibrosis and reliably detect the stage of liver cirrhosis. The total serum protein N-glycome is an excellent biomarker for the detection of liver cirrhosis. The methods and device of the present invention can be used to detect serum markers for liver cirrhosis with high specificity and good sensitivity, such as N-glycome, and thus provide an alternative to biopsy in cirrhosis patients.

The methods and device of the present invention can also be used in the evaluation of therapeutic protein products. Monoclonal antibodies are important therapeutics, targeting a variety of diseases ranging from cancers to neurodegenerative disorders. The methods of the present invention can be used in developmental stages and prior to clinical use, for characterization of these molecules, an aim that presents serious challenges for current analytical techniques. Moreover, therapeutic proteins produced using recombinant DNA technologies are generally complex, heterogeneous, and subject to a variety of enzymatic or chemical modifications during expression, purification, and long-term storage. The use of the present invention for the evaluation of recombinant protein sequences could provide information regarding amino acid modifications and sequence alterations that have the potential to affect the safety and activity of therapeutic protein products. The device could be used for evaluation of recombinant protein heterogeneity resulting from post-translational modifications, sequence variations generated from proteolysis or transcriptional/translational errors, and degradation products which are formed during processing or final product storage. The methods and device of the present invention can be used for the analysis of monoclonal antibody glycosylation, deamidation, and disulfide mapping for a wide variety of heterogeneous therapeutic protein products.

The methods and device of the present invention can also be used to detect foodborne illness. The bacterium *Listeria monocytogenes* causes about 1,600 human listeriosis cases and 250 deaths annually in the US, representing about 10% of all US deaths from foodborne illnesses. The present invention can be used to identify *L. monocytogenes* proteins that co-regulate genes contributing to transmission and virulence. The methods of the present invention allow sensitive detection with accurate quantitation in complex samples of low abundance proteins which could be important parts of the regulatory network and help define regulons controlled by the *L. monocytogenes* regulatory proteins.

The present invention can aid in determining *Clostridium difficile* virulence. *C. difficile* is a gram positive spore forming anaerobic bacterium which is responsible for a wide spectrum of diseases in human and a variety of animal species. Clinical manifestations range from asymptomatic colonization and mild diarrhea to life-threatening pseudomembranous colitis and death. Although *C. difficile* toxins have been well-studied, *C. difficile* virulence is not well understood. The present invention can be used to determine *C. difficile* time-dependent protein expression changes under in vitro conditions that mimic in vivo infection, with the aim of identifying potential candidates for diagnostic or therapeutic measures.

Crohn's disease (CD) is a chronic, pathological, T cell-mediated autoimmune inflammatory condition involving IL-12 and IL-23, which are cytokines produced by antigen-presenting cells in response to intracellular microbial invasion. However, given their roles in immunology, directly targeting IL-12/IL-23 in therapy may have undesirable consequences, so other targets may be more efficacious. The methods and device of the present invention can be used to help identify extracellular, soluble factors from CD patient plasma that stimulate IL-12/IL-23 production.

Another aspect of the present invention relates to methods of fabricating a biomolecular processor as described herein. The fabrication process generally consists of the following steps (1) fabrication of nanofluidic structures including microfluidic networks and nanochannels in a substrate, (2) positioning of nanowires on the substrate, (3) formation of nanogaps in nanowires at the nanochannel/nanowire junctions, (4) formation of micro-contacts to nanowire sensors, and (5) bonding with a cover plate to complete the nanofluidic sensor device. The fabrication process sequence for steps (1)-(3) can be arbitrarily chosen and/or two of them can be arbitrarily combined. Each of the steps are described in more detail infra.

Figure 12:
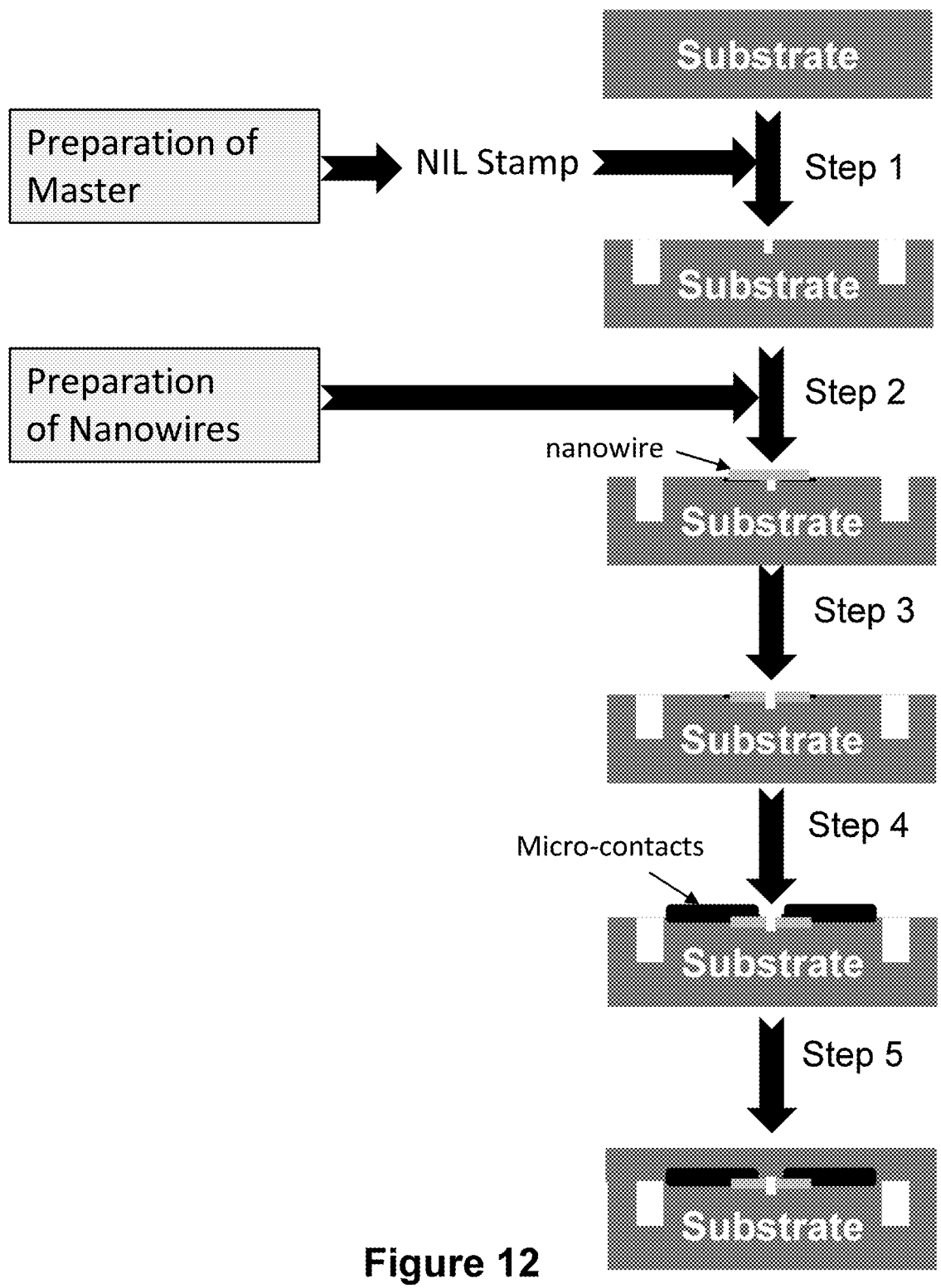
FIG. 12 is a schematic overview of a first suitable process for fabricating the biomolecular processor of the present invention.

One exemplary fabrication process sequence is shown in FIG. 12. In this embodiment, Step 1 involves building micro- and nanochannel structures in a substrate (e.g., a polymer substrate) using a single step nanoimprint lithography (NIL) process with a pre-structured stamp. In Step 2, nanowires or nanoparticles are positioned perpendicular to the formed channels of the substrate, these channels becoming the feeder and time-of-flight channels. In Step 3, nanogaps are formed in the positioned nanowires positioned over the channels to form a pair of sensing electrodes that intersect a respective time-of-flight channel. In Step 4, the sensing electrodes are connected to micro-contacts for external lead connections. In Step 5, the fabricated structure is bonded with a cover plate to complete the enclosed fluidic device.

Figure 13:
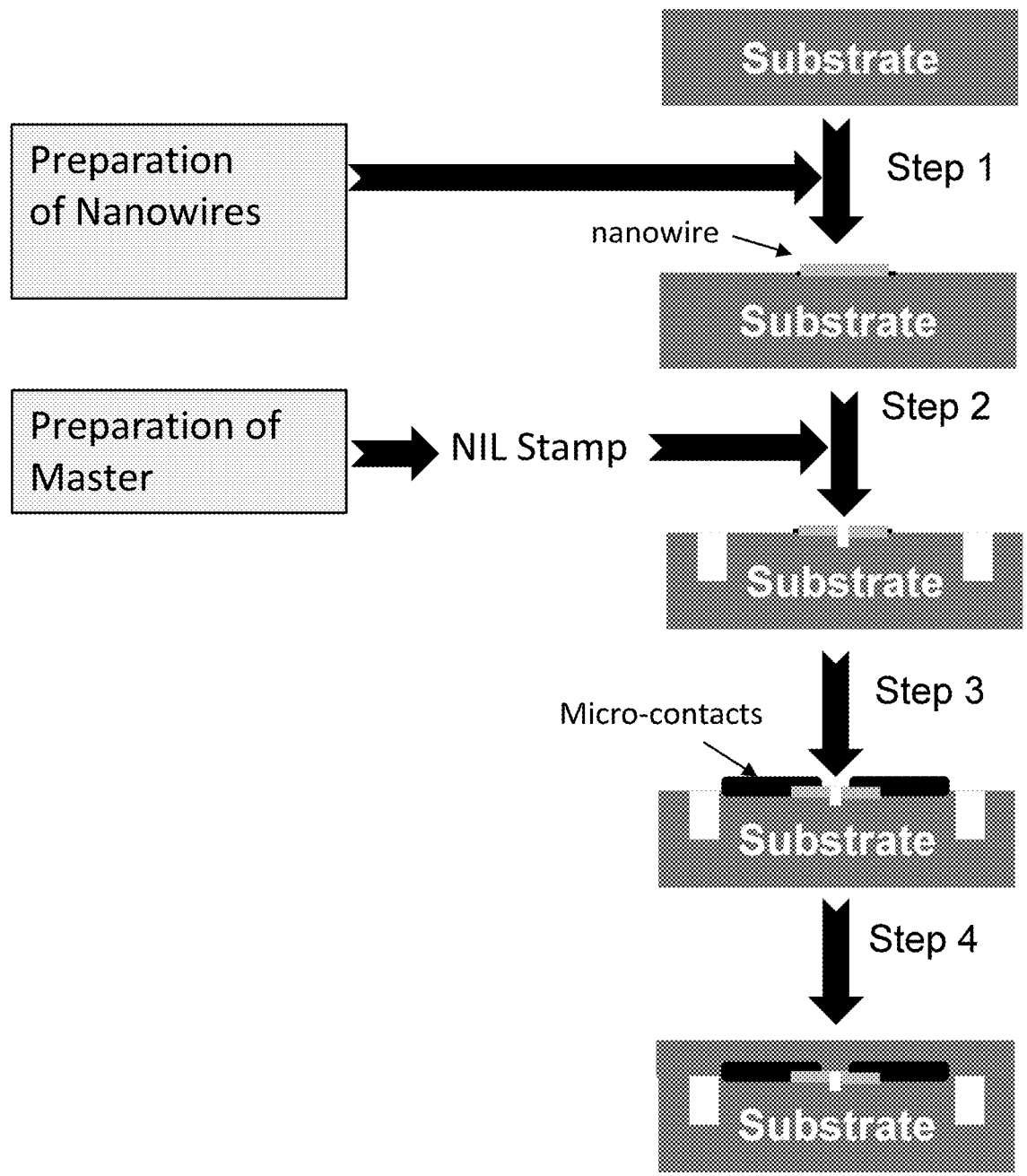
FIG. 13 is a schematic overview of a second suitable process for fabricating the biomolecular processor of the present invention.

An alternative fabrication process sequence is shown in FIG. 13. In this embodiment, Step 1 involves positioning nanowires or nanoparticles at the sensor locations prior to nanochannel formation. In Step 2, the micro- and nanofluidic structures, channels are formed using NIL. Nanogaps can be formed during or after the NIL process, or are partially formed during the NIL process and completed in follow-up processes. Following the formation of nanogaps, the sensor electrodes are connected to micro-contact pads for external lead connections (Step 3), and the fabricated structure is bonded with a cover plate to enclose the fluidic device (Step 4).

Figure 14:
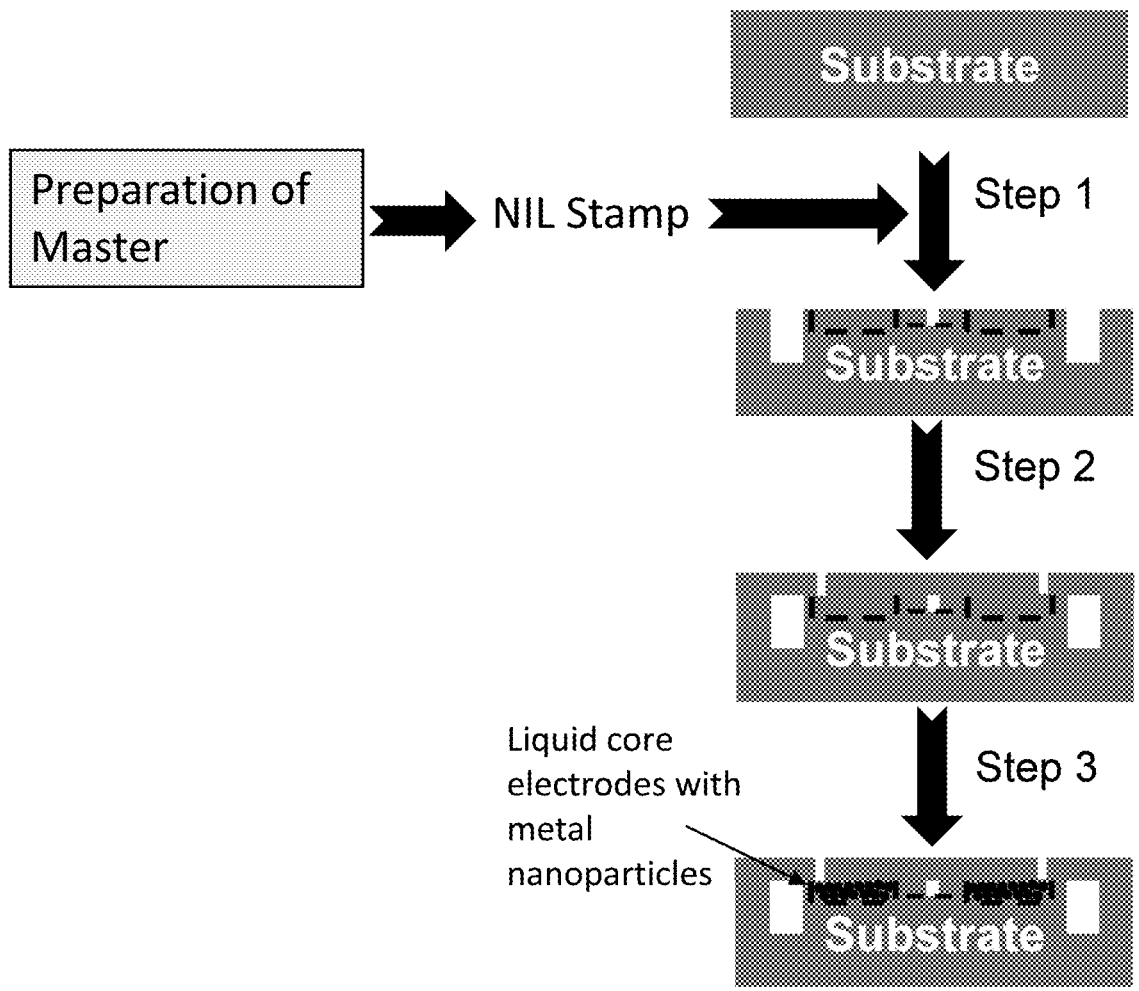
FIG. 14 is a schematic overview of a third suitable process for fabricating the biomolecular processor of the present invention.

Another alternative fabrication process sequence is depicted in FIG. 14. This process involves building the nanofluidic device using transverse liquid ion core electrodes that can be subsequently filled with conductive metal nanoparticles to improve their conductivity. NIL is employed to fabricate the micro/nanofluidic network, structures and channels and the liquid core nanoelectrode structures (Step 1). The fabricated structure is then bonded with a cover plate to enclose the fluidic device (Step 2), and metallic nanoparticles are added to the liquid core electrodes (Step 3).

Regardless of the fabrication process sequence that is employed, a size reduction process step can be included following the fabrication of nanofluidic structures by NIL to reduce the size of the fluidic network, in particular the time-of-flight channel(s). For example, this process step may include applying pressure with a blank platen at an elevated temperature below the glass transition temperature ($T_g$) of the substrate polymer, which will both reduce the size of nanofluidic structures and reduce the sidewall roughness of the nanofluidic structures.

Common to all fabrication processes is the use of a "master stamp" for the nanoimprint lithography based formation of the micro/nanofluidic network and structures.

Figure 15:
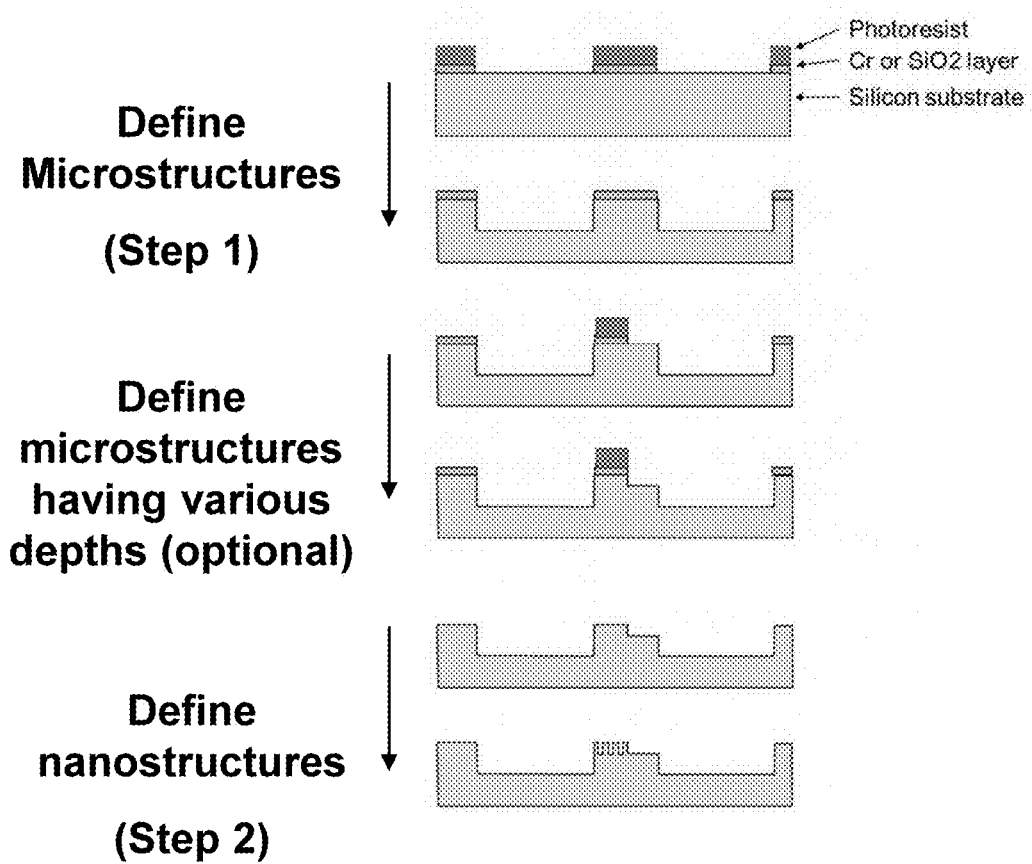
FIG. 15 is a schematic overview of the formation of a silicon master stamp used to fabricate the biomolecular processor of the present invention.

FIG. 15 depicts an exemplary fabrication process for master stamp structures in a silicon substrate. In Step 1, photolithography and chromium etching in combination with a Si etching step, either using reactive ion etching or wet chemical etching, are carried out to define and form microstructures of the fluidic networks in the silicon substrate. If microstructures with different depths are needed, the photolithography and Si etching steps are repeated. In Step 2 focused ion beam milling or electron beam lithography can be employed to form the nanostructures of the sensor device including the nanochannels (e.g., time-of-flight channels), nanochannel inlet structures, and the support structure of the bioreactor chamber.

The fabricated master stamps are used directly as NIL stamps to produce the fluidic structures in a polymer substrate, or they are used as master molds to produce resin NIL stamps with negative tone structures with respect to the structures in the master stamp. With regard to the latter, fabricated master stamps can be replicated into various materials via thermal or UV NIL process which will subsequently be used as NIL stamps to produce the fluidic structures in polymer substrates as described by Wu et al., "Complete Plastic Nanofluidic Devices for DNA Analysis via Direct Imprinting with Polymer Stamps," *Lab Chip* 11(17):2984-9 (2011), which is hereby incorporated by reference in its entirety). The materials for NIL resin stamps include, for example, thermoplastic polymer sheets, thermoplastic polymer layers coated on a substrate, UV curable resins coated on a substrate, and sol-gel materials coated on a substrate. The substrates that can be used include polymer sheets, metal, silicon, glass, quartz, and composite materials. Use of UV curable resins coated on a polymer substrate is one preferable material because it results in low adhesion to the molded polymer substrate by lowering Young's moduli of the materials in contact during molding. Thermal stress is also reduced due to the similar thermal expansion coefficients of the UV resin/polymer stamp and polymer substrate.

Figure 16A:
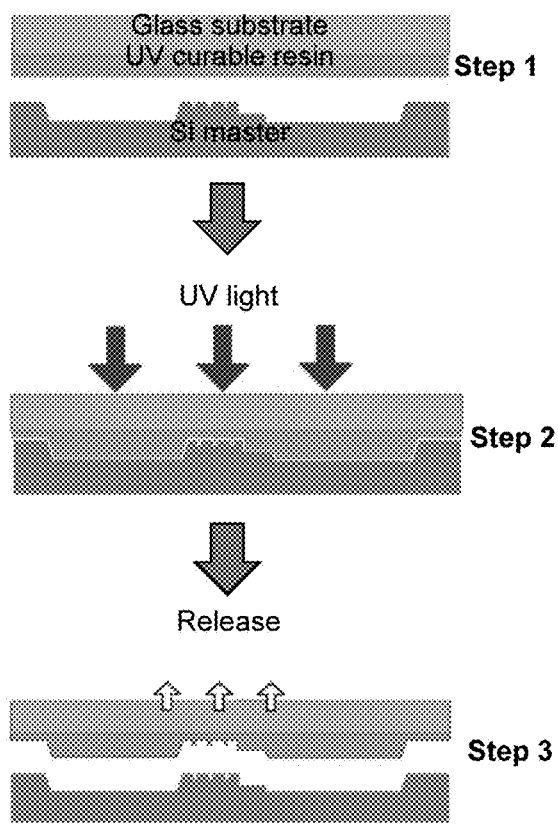
FIGS. 16A-16B depict the nanoimprint lithography processes used to form a resin stamp from the silicon master stamp (FIG. 16A) that is subsequently used to fabricate the micro- and nanofluidic network and other structures associated with the biomolecular processor of the present invention (FIG. 16B).

FIG. 16A shows a process to produce a resin stamp from a silicon master stamp via UV nanoimprint lithography. In this process an appropriate amount of low viscous curable UV resin is first dispensed or spin-coated on a glass substrate (Step 1). The UV curable resin/substrate is then gently pressed on a silicon master (Step 2). After the resin fully fills into the structures of the silicon master, UV light is used to cure or polymerize the UV resin. The cured UV resin/ substrate is demolded from the silicon master to complete fabrication of a UV resin stamp from the silicon master stamp (Step 3).

Figure 16B:
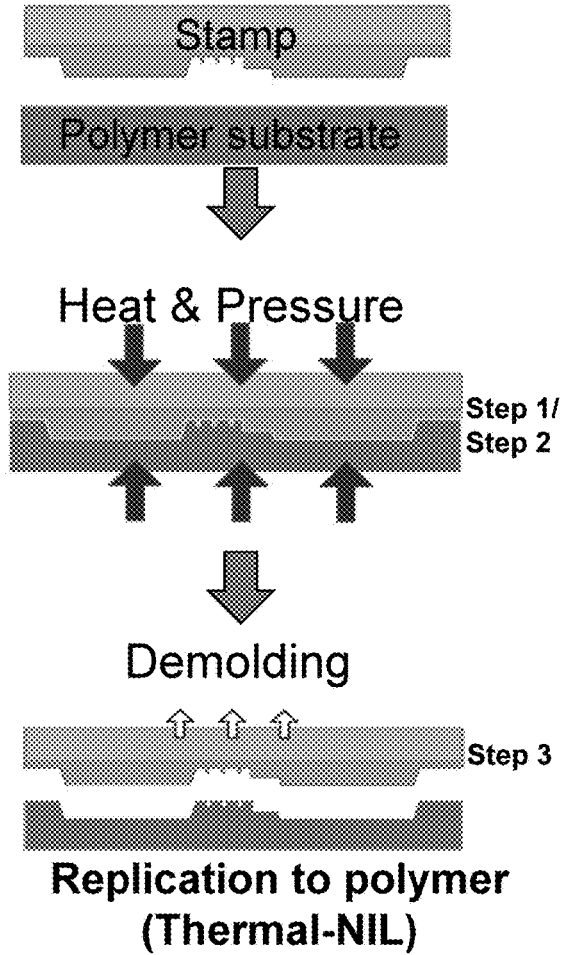

FIG. 16B shows the process of producing the micro/nanofluidic network structures of the biomolecular processor in a thermoplastic polymer substrate via thermal NIL using the fabricated resin stamp. The stamp/substrate assembly is heated above the glass transition temperature ($T_g$) of the substrate polymer, usually 10-100° C. above the $T_g$ (Step 1). This is followed by applying pressure on top of the stamp surface (Step 2). Pressure can be applied by either force application using two parallel platens, or by compressed air. Compressed air is desirable to achieve homogeneous pressure application and conformal contacts between the NIL stamp and polymer substrate. After the substrate polymer is entirely filled into the stamp structures, the stamp/substrate assembly is cooled down below the $T_g$ and the stamp is demolded from the molded substrate (Step 3). Suitable polymer substrates for thermal NIL include, without limitation, PMMA, PC, and COC.

Figures 17A, 17B:
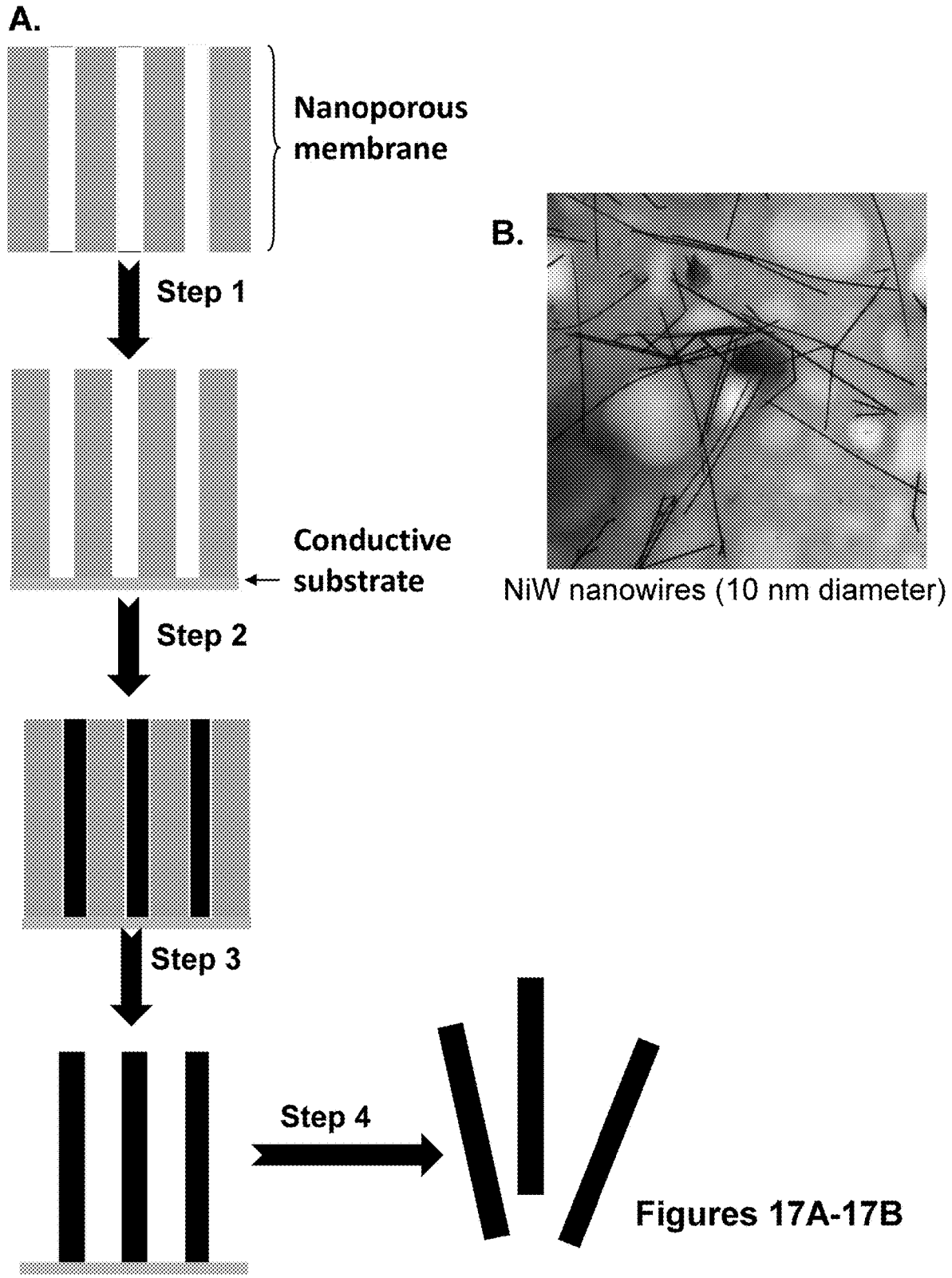
FIGS. 17A-17B show the process of forming single phase nanowires suitable for use in the biomolecular processor of the present invention (FIG. 17A) and a scanning electron microscopy (SEM) image of the nanowires produced in this process (FIG. 17B).

Another feature common to all biomolecular processor fabrication processes is the fabrication and positioning of nanowires or nanoparticles within the substrate to serve as sensors. Suitable nanowires can be formed using processes known to those of skill in the art. A schematic overview of the general fabrication process is shown in FIG. 17A. Briefly, a nanoporous template or membrane is formed from a plastic or aluminum oxide substrate using electron beam lithography, and a conductive substrate, e.g., silver, gold, or indiumtin oxide, is deposited on the base of the membrane by sputtering (Step 1). The nanowires are formed by electrodeposition of a metal or alloy into the nanoporous membrane having a conductive substrate (Step 2). The nanoporous membrane is dissolved away (Step 3) and conductive substrate is removed (Step 4) to release the nanowires. FIG. 17B is an SEM of NiW nanowires having a 10 nm diameter formed via this process.

The electrodeposition of one or more dissimilar metals or alloys into the nanoporous template to form segmented nanowires is typically carried out using two different techniques, e.g., a dual bath approach where different electrolytic solutions and different plating conditions are used, or a single bath approach, using one solution and pulsing either the current or potential to create the dissimilar layer (see e.g., Liu et al., "Perpendicular Giant Magnetoresistance of Multilayered Co/Cu Nanowires," *Physical Review B* 51: 7381-7384 (1995); Blondel et al., "Wire-Shaped Magnetic Multilayers for 'Current Perpendicular to Plane' Magnetoresistance Measurements," *Journal of Magnetism and Magnetic Materials* 148:317-318 (1995); Blondel et al., "Comparative Study of the Magnetoresistance of Electrodeposited Co/Cu Multilayered Nanowires Made by Single and Dual Bath Techniques," *Journal of Magnetism and Magnetic Materials* 165:34 (1997); Piraux et al., "Arrays of Nanowires of Magnetic Metals and Multilayers: Perpendicular GMR and Magnetic Properties," *Journal of Magnetism and Magnetic Materials* 175: 127-136 (1997); Evans et al., "Current Perpendicular t Plane Giant Magnetoresistance of Multilayered Nanowires Electrodeposited in Anodic GMR in Electrodeposited CoNiFe/Cu Multilayered Nanowires and Nanotube Aluminum Oxide Membranes," *Applied Physics Letters* 76:481 (2000); Davis et al., "GMR in Electrodeposited CoNiFe/Cu Multilayered Nanowires and Nanotube," *ECS Transactions* 1:71-77 (2005); and Pratt et al., "Perpendicular Giant Magnetoresistances of Ag/Co Multilayers," *Physical Review Letters* 66: 3060-3063 (1991), which are hereby incorporated by reference in their entirety).

A commonality of these techniques is that the interfacial regions are subject to breaking, which can be used to form the prerequisite nanogap required for the biomolecular processor.

An annealing step can help to create large grains and thus reduce the nanowire resistance increasing the ability to make electrode measurements of single monomer units. However, a challenge is to match the coefficient of thermal expansion of the adjacent segments. Accordingly, applicants have developed conditions to electrodeposit FeNiCo as a nanowire using pulsed electrodeposition with a controlled composition. By changing the applied current density or adding an additive, such as 2-butyne-1,4-diol (BD), the deposit composition can be altered, thus tailoring the coefficient of thermal expansion. Gold (or silver) segments are electrodeposited from a separate electrolyte, in a dual bath configuration, and a sulfuric acid treatment is included to create robust, segmented nanowires between the Au and the FeNiCo step.

Figure 18:
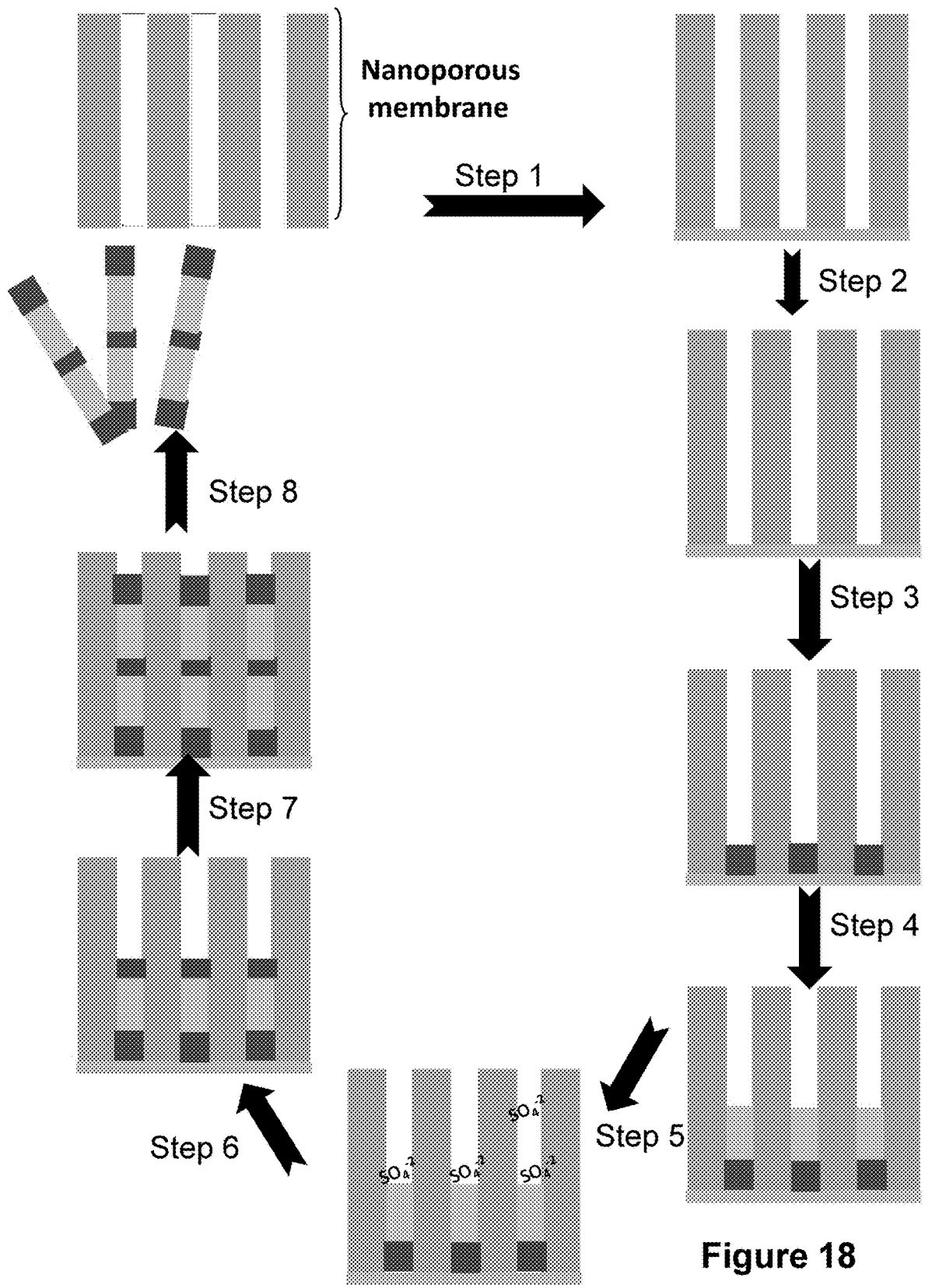
FIG. 18 shows the process of forming segmented nanowires suitable for use in the biomolecular processor of the present invention.

FIG. 18 is a schematic overview of the above described process and conditions used to generate robust segmented nanowires suitable for use in the biomolecular processor of the present invention. In Step 1, a conductive substrate, e.g., silver, is deposited on the base of a nanoporous membrane by sputtering. The surface is exposed to air (Step 2) prior to electrochemical pulsed deposition of FeNiCo (Step 3). The pulsed deposition can be carried out with a 50% duty cycle (2 sec. on/2 sec. off) and an applied current density equal to or less than 25 mA/cm². A higher current density can be used to decrease the amount of Fe but the pulse deposition off time should be increased. Addition of 0.1 g/L of 2-butyne-1,4-diol (BD) will result in an alloy with more Ni at these conditions. BD is also used to tailor the coefficient of thermal expansion, and prevent corrosion during the pulse off time. In Step 4, Au is electrochemically deposited from a separate electrolyte using DC plating. The surface is treated with a sulfuric acid solution (5 vol %) (Step 5) prior to the subsequent electrochemical deposition of FeNiCo (Step 6). Steps 4-6 are repeated to form fully segmented wires (Step 7). The membrane is dissolved and nanowires released (Step 8).

The nanowires of the biomolecular processor preferably have diameters ranging from 5-20 nm. While methodologies involving electrodepositing in nanoporous membranes for the production of 20-200 nm wires are known in the art, the fabrication of thinner wires requires refinement of the nanoporous membrane or an alternative technique.

Figure 19:
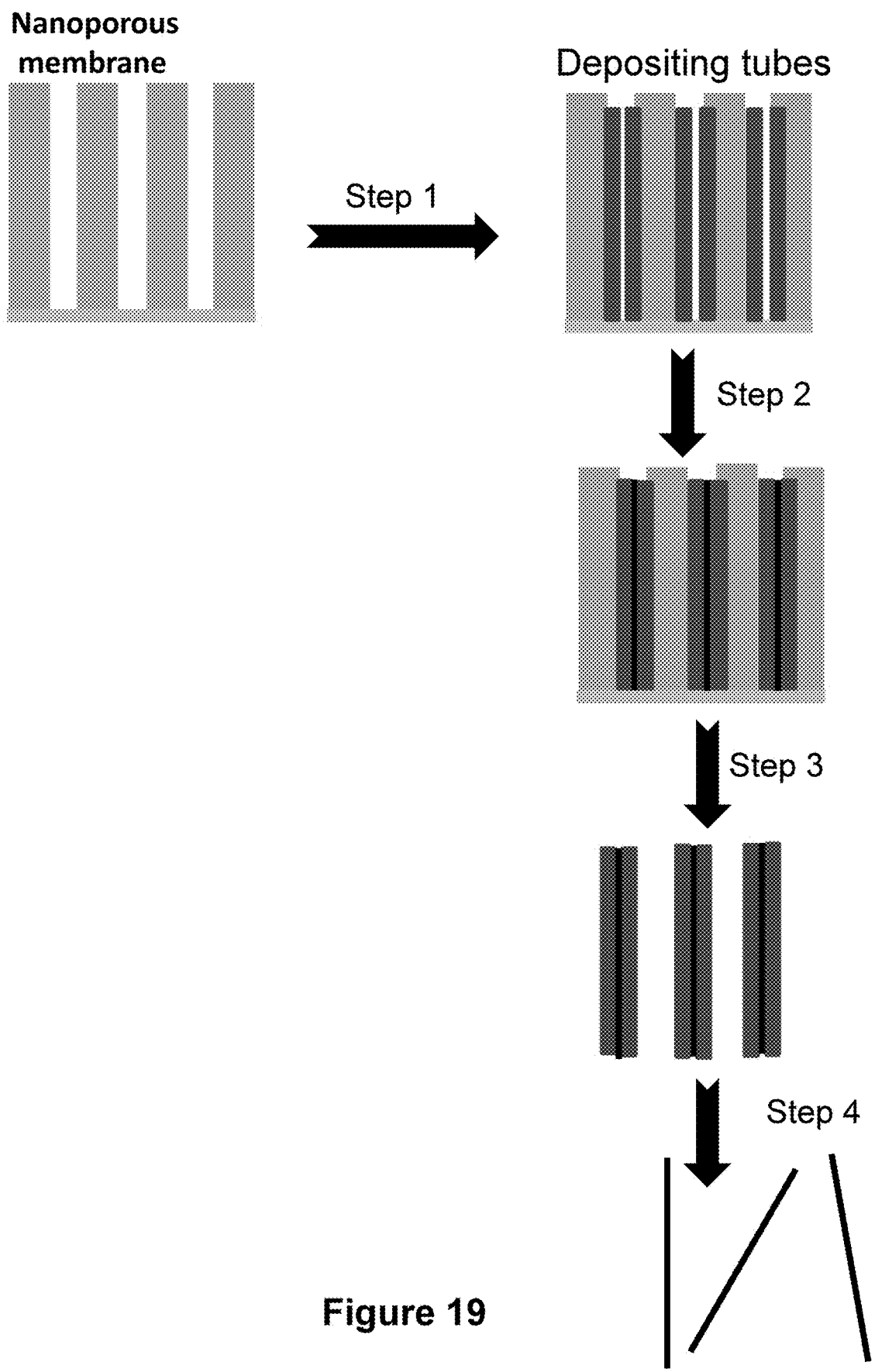
FIG. 19 is a schematic showing a process for forming ultrathin nanowires suitable for use in the biomolecular processor of the present invention.

With regard to the latter, FIG. 19 is a schematic showing a process for the fabrication of ultrathin nanowires using sacrificial nanotubes (i.e., a modified nanoporous membrane). The nanotubes consisting of a dissimilar metal or polymer, such as copper or polypyrrole, are deposited into the nanoporous template (Step 1) by control of the plating conditions to be under mass transport control. The wires and their segments are then electrochemically deposited into the nanotubes (Step 2). To avoid deposition at the pore mouth Superfilling additives are used that promote bottom-up filling. The tube-wire composite is released by dissolving the membrane (Step 3) and the wires are released by preferentially etching the tube (Step 4).

Figure 20:
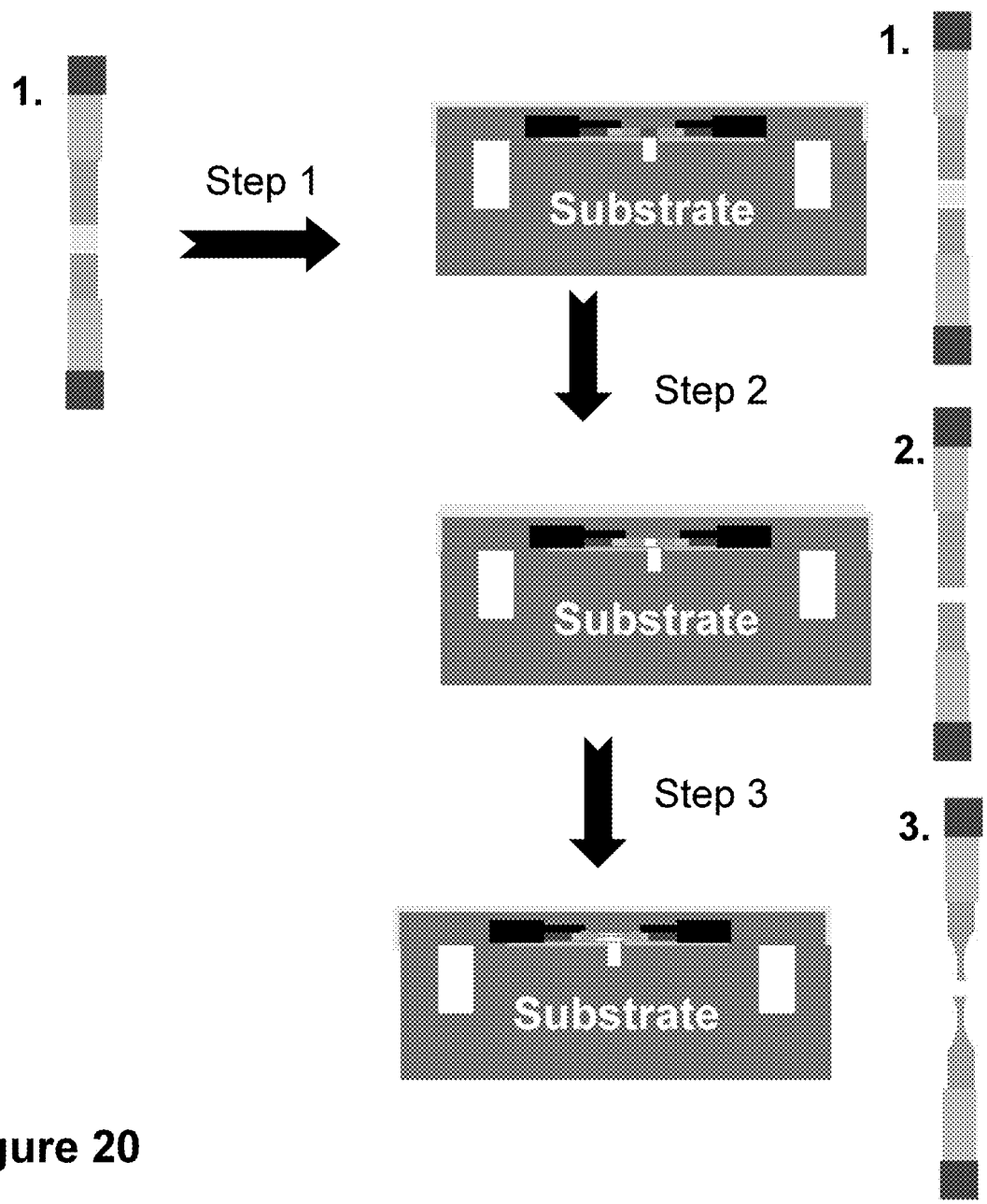
FIG. 20 shows a process of nanowire thinning using selective etching.

In an alternative embodiment, ultrathin electrodes are formed using an electrochemical etching approach that is depicted in FIG. 20. The segmented nanowires, fabricated as described supra, are positioned at the sensor locations on the device (Step 1). The sacrificial gap region is first chemically etched within the channel (Step 2). The sharp edge on the remaining electrode provides a preferential region for electrochemical etching provided the current distribution is largely primary (e.g., low Wagner number) and/or the etching is driven by diffusion. Each side is etched using the electrical contacts built into the device (Step 3) to create the ultrathin electrodes suitable for use in the biomolecular processor.

Figure 21:
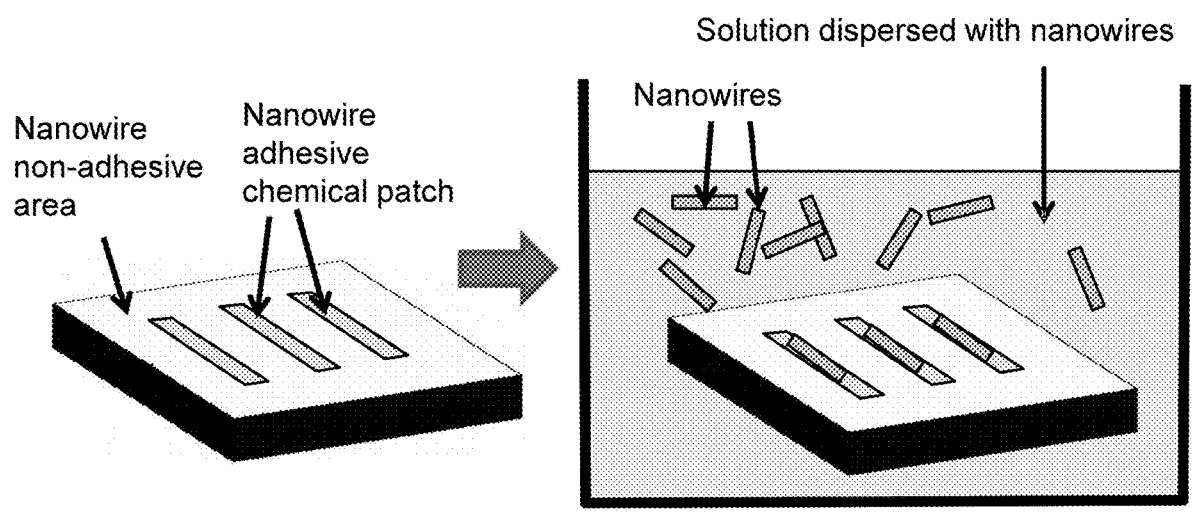
FIG. 21 is a schematic illustrating the positioning of nanowires using chemical patches at sensing electrode locations on the biomolecular processor of the present invention.

Another integral component of the fabrication process involves methods of positioning the nanowires or nanoparticles at the sensor locations of the biomolecular processor. This is particularly challenging with sub-20 nm nanowires. In one embodiment, surface-programmed assembly is used. In surface-programmed assembly, chemical patches to which the nanowires will specifically "adhere" to are formed on the surface of the substrate as shown in FIG. 21. The substrate containing the chemical patches is exposed to a solution of dispersed nanowires or nanoparticles which position themselves on the surface of the substrate at the locations of the chemical patches.

Figure 22:
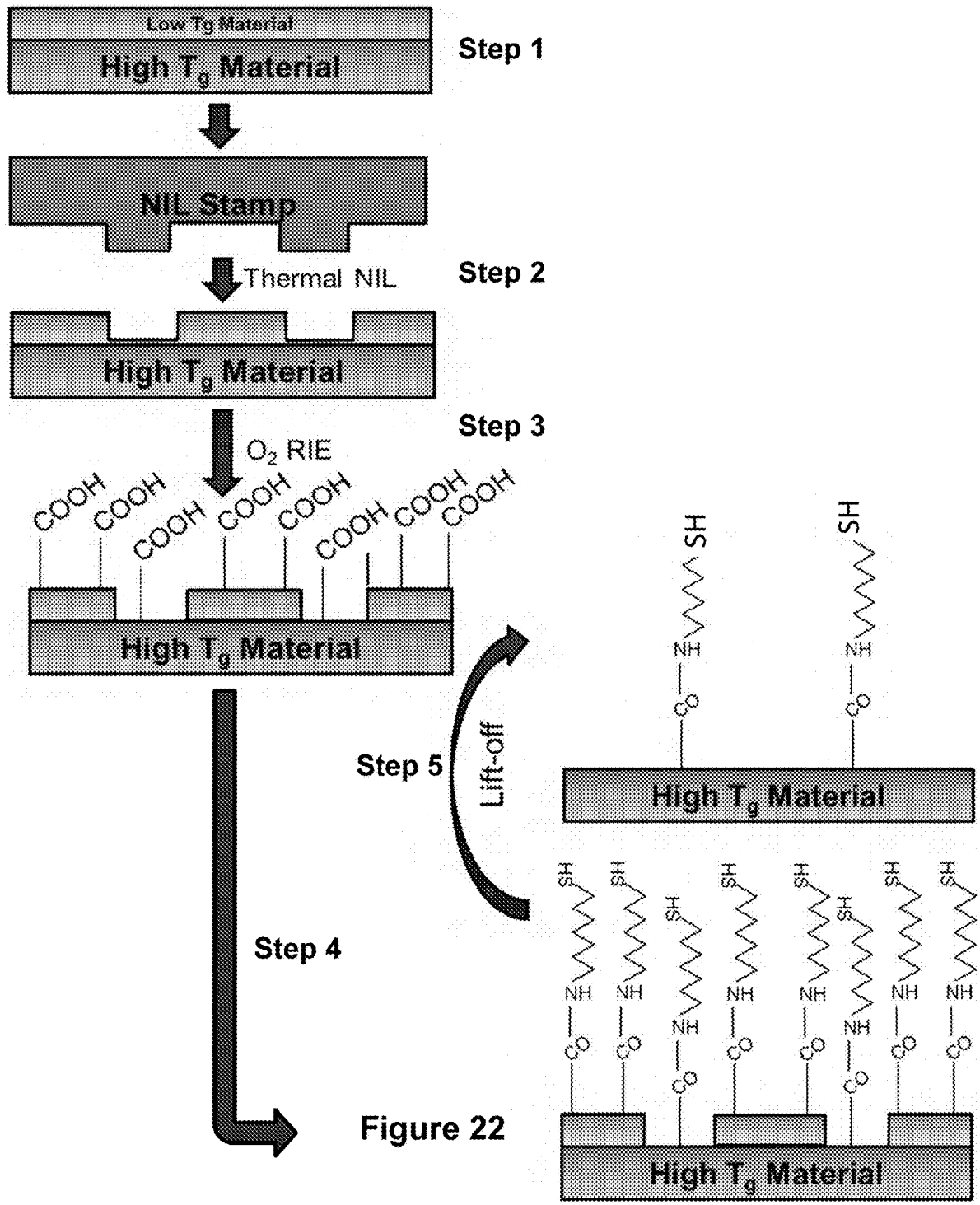
FIG. 22 is a schematic overview showing the formation of chemical patches on the substrate of the biomolecular processor using molecular assembly patterning by lift-off (MAPL) technique.

Chemical patches can be formed on the surface of the substrate using molecular-assembly patterning by lift-off (MAPL) technique (see e.g., Falconnet et al., "A Novel Approach to Produce Protein Nanopatterns by Combining Nanoimprint Lithography and Molecular Self-Assembly," *Nano Lett.* 4(10):1909-1914 (2004); Park et al., "Nanostructuring of Anti-Adhesive Layers by Hot Embossing Lithography," *Micorelectron Eng.* 67-68: 252-258 (2003); Park et al., "Chemical Patterning of Sub-50-nm Half Pitches Via Nanoimprint Lithography," *Microelectron. Eng.* 78-79:682-688 (2005); and Park et al., "Chemical Nanopatterns Via Nanoimprint Lithography for Simultaneous Control Over Azimuthal and Polar Alignment of Liquid Crystals," *Adv. Mater* 17(11): 1398-1402 (2005), which are hereby incorporated by reference in their entirety). A general schematic outlining this process is shown in FIG. 22, which shows as an example, the generation of chemical patches consisting of alkanes terminated with thiol groups that have a high affinity for gold-based materials. For this process as depicted in FIG. 22, a resist with a lower glass transition temperature (Tg) compared to the substrate (High Tg material) is spin coated on this substrate (Step 1). In Step 2, thermal NIL is utilized to transfer patterns into this low Tg resist. This is followed by an reactiv-ion etching step to break through the remaining resist, which also creates functional groups on the polymer substrate (Step 3). Following chemical reaction of the pendant—COOH surface functional groups with alkane thiols (Step 4), the remaining resist is lift off from the surface (Step 5). These thiols serve as anchoring points for gold or silver nanowires through self assembly.

Figure 23:
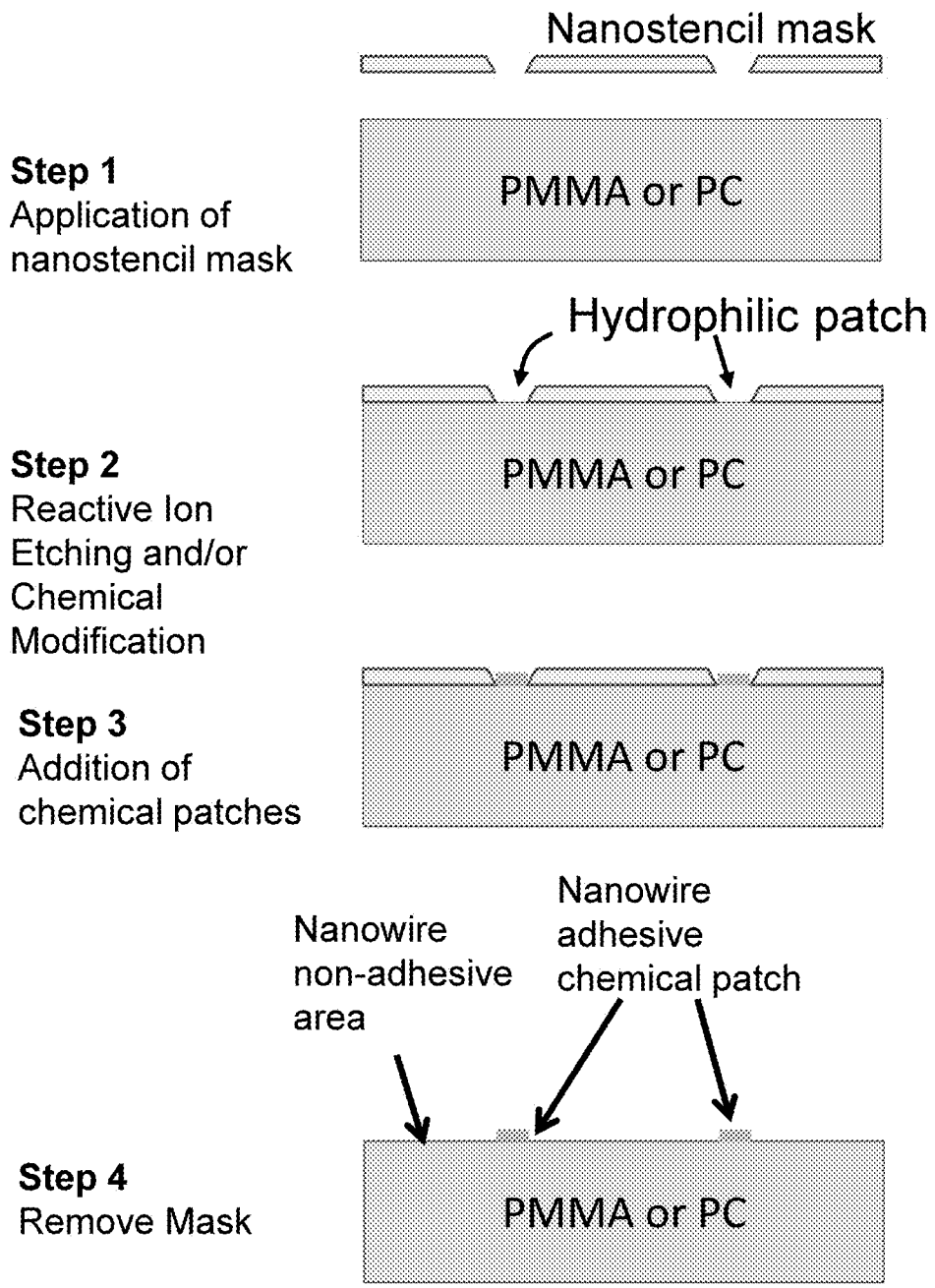
FIG. 23 is schematic overview showing the formation of chemical patches on the substrate of the biomolecular processor using a nanostencil mask.
Figure 24:
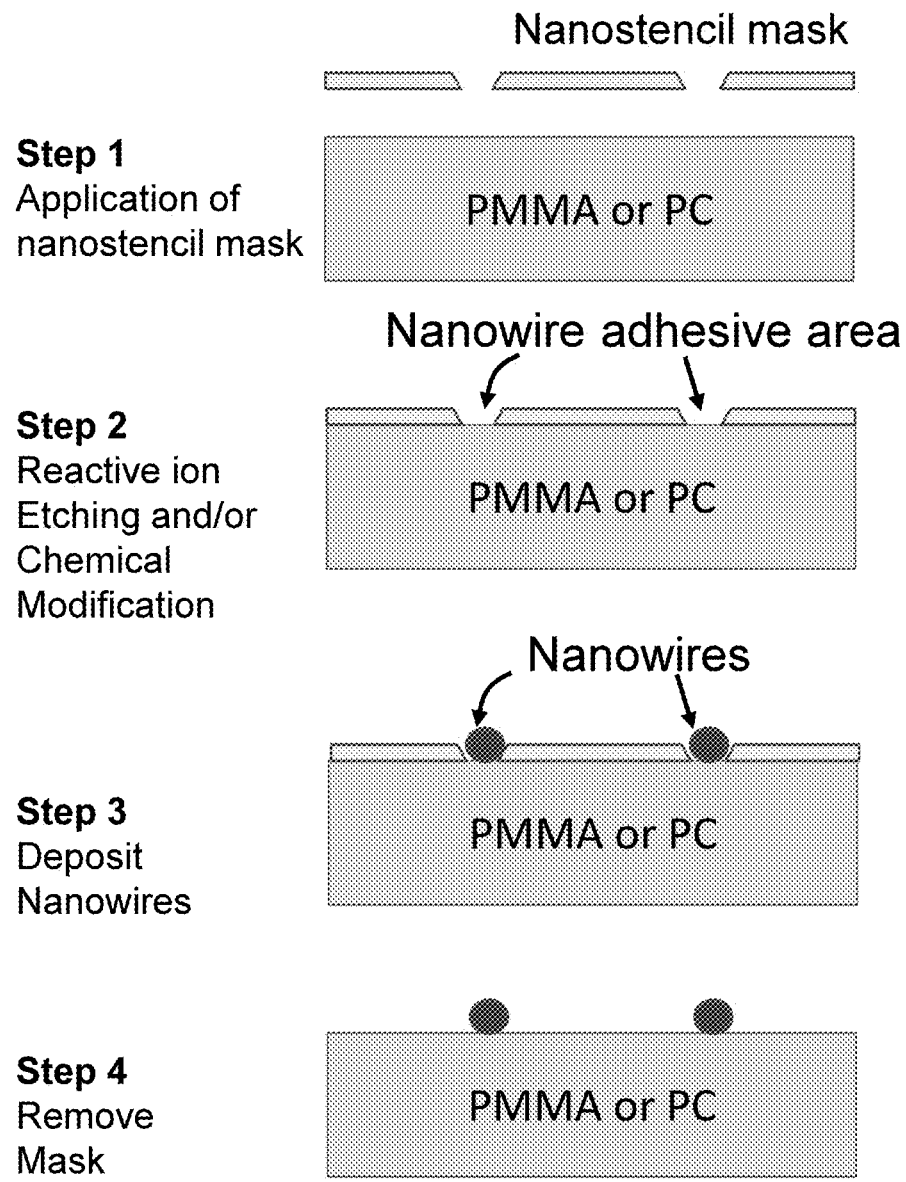
FIG. 24 is a schematic overview showing the use of the nanostencil mask to position nanowires at electrode sensor locations on the biomolecular processor.

In an alternative embodiment, chemical patches are formed on the surface of the substrate via a stencil mask as shown in FIG. 23. Thermoplastics, such as PMMA and PC, are exemplary substrates. Generally this process involves applying a nanostencil mask to the surface of the substrate to mask the areas of the surface where a chemical patch is not desired (FIG. 23, Step 1). The exposed surface is subject to reactive ion etching (RIE) and/or other chemical modification for the addition of chemical patches (Steps 2 and 3). Upon removal of the mask (Step 4), the chemical patches are located at the desired positions. An alternative embodiment is depicted in FIG. 24. In this embodiment, following application of the nanostencil mask (Step 1) and addition of chemical patches via RIE and/or other chemical modification (Step 2) nanowires are deposited (Step 3) with the mask still intact. The mask is then removed following nanowire positioning on the substrate surface (Step 4).

Figure 25:
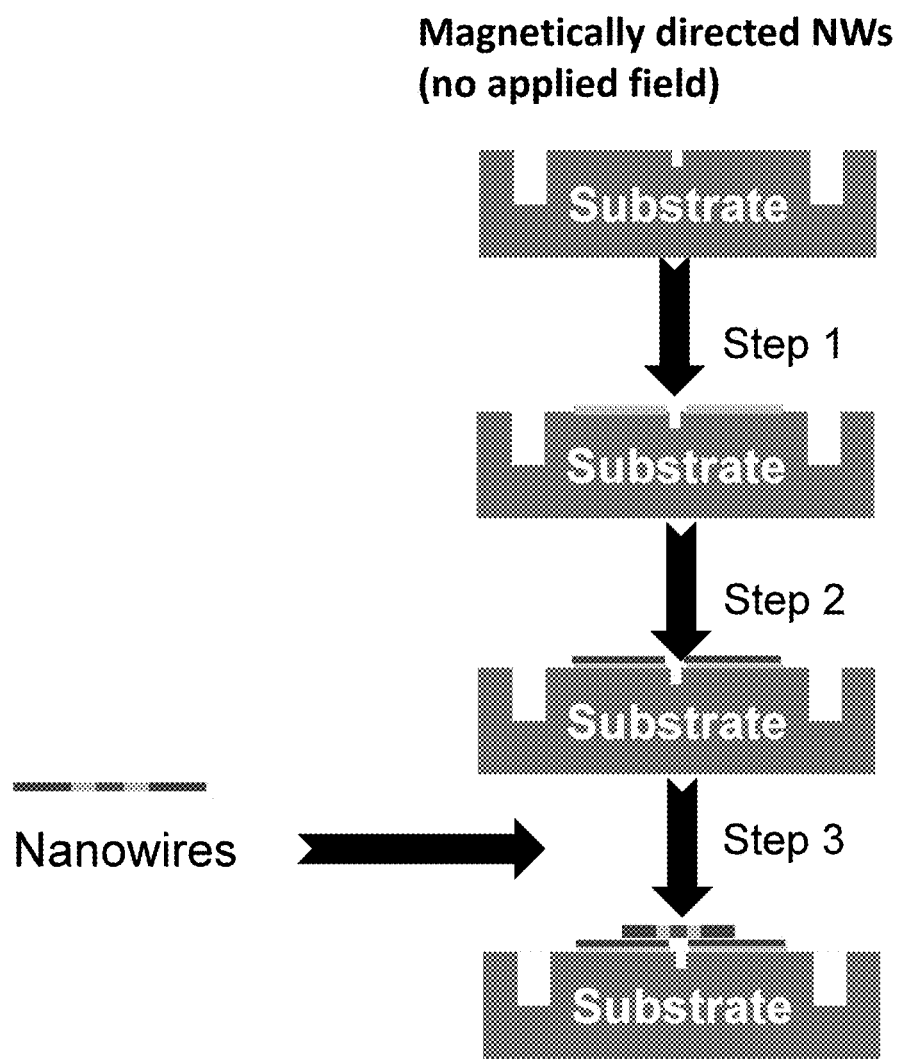
FIG. 25 is a schematic overview showing the process of magnetically directing nanowires to their electrode sensor locations without using an applied magnetic field.
Figure 26:
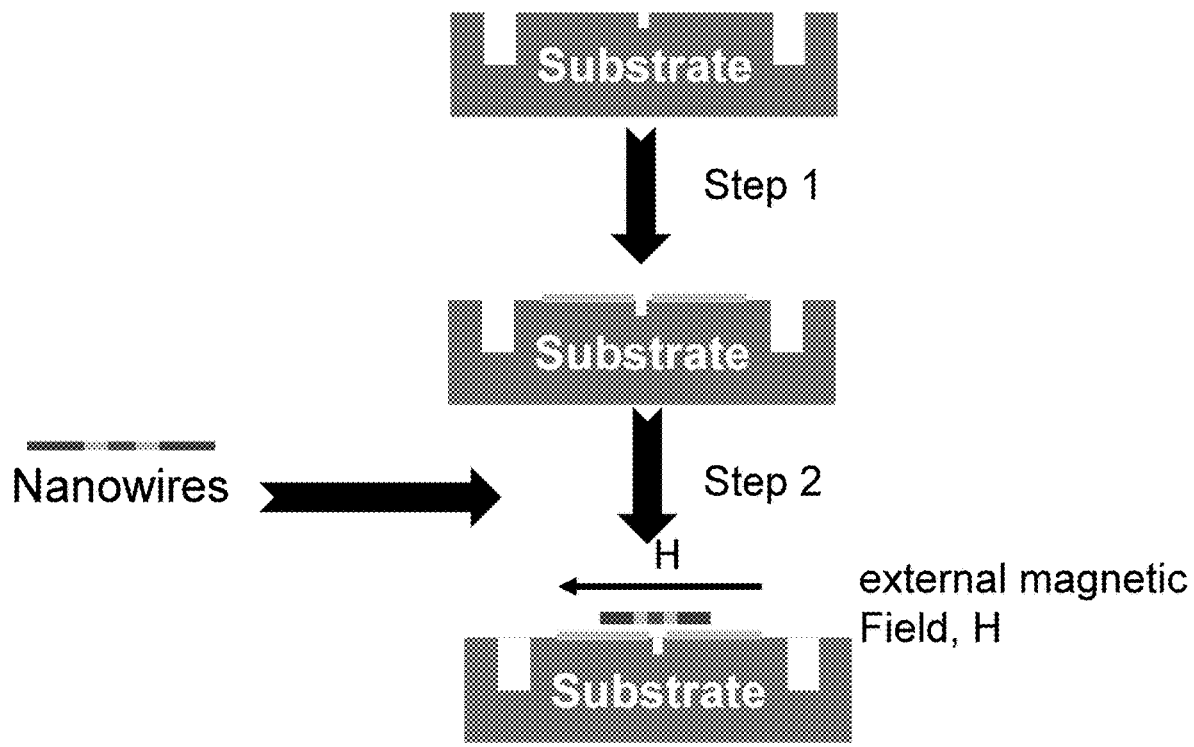
FIG. 26 is schematic overview showing the process of magnetically directing nanowires to their electrode sensor locations using an externally applied magnetic field.

The nanowires can also be magnetically directed to the nanosensing locations on the substrate in the absence or presence of an applied field as depicted in FIGS. 25 and 26, respectfully. In the embodiment shown in FIG. 25, nanoimprint lithography is used to form micro/nanofluidic channels and structures within the substrate. Subsequently gold contacts (electrodes) are deposited onto the substrate surface at sensor locations on either side of the nanochannels (Step 1). Iron is deposited over the gold contacts to create the magnetic field (Step 2), and the nanowires align perpendicularly to the channels (Step 3). In the embodiment of FIG. 26, gold contacts (electrodes) are deposited onto the substrate surface at sensor locations on either side of the nanochannels (Step 1). The nanowires are aligned parallel to an external magnetic field that is applied after gold contact deposition (Step 2).

Figure 27:
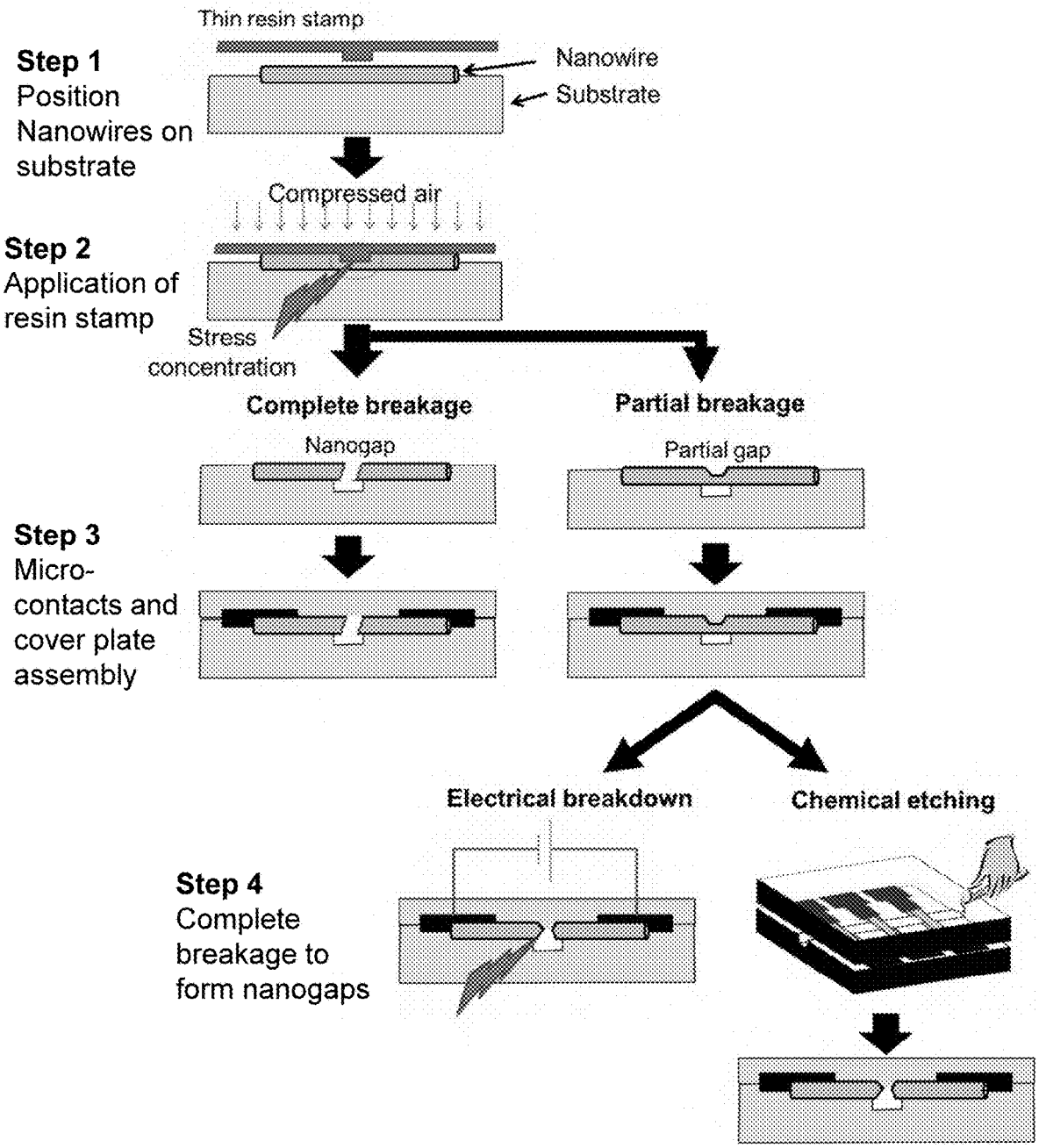
FIG. 27 depicts a process of simultaneous nanogap and nanochannel formation using nanoimprint lithography.
Figure 28:
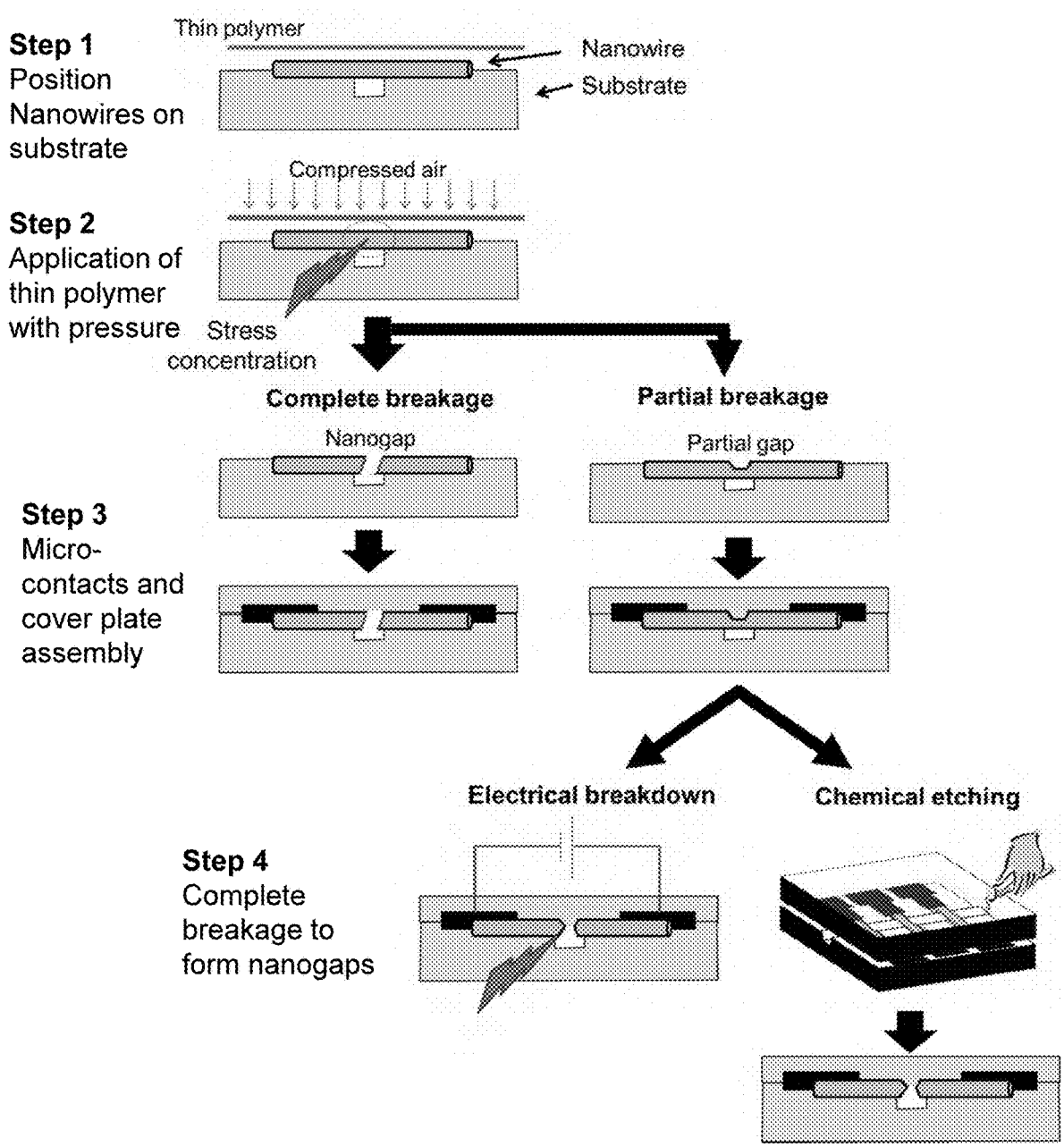
FIG. 28 shows a process of nanogap formation using nanoimprint lithography when the nanochannels and other fluidic networks are preformed in the substrate.

Nanogap formation in the positioned wires can be achieved in various ways as depicted in FIGS. 27 and 28. FIG. 27 shows simultaneous formation of the micro/nanofluidic network (i.e., channels and structures) and nanogap formation using nanoimprint lithography. In this embodiment, the nanowires are positioned on the substrate using any of the suitable methods described above (Step 1). In Step 2, a thin resin stamp suitable for forming the nanogap and nanochannel is applied to the substrate containing the positioned wires with pressure (e.g., compressed air). Depending on the stress concentration, either complete or partial breakage is achieved. The micro-contacts are deposited on the substrate surface and the coverplate is bonded to enclose the nanofluidic device (Step 3). If only partial breakage is achieved, complete breakage is formed by subsequent electrical breakdown (i.e., applying high electrical field through the nanowire), chemical etching, or other suitable means (Step 4).

FIG. 28 depicts the process of nanogap formation by nanoimprint lithography when the micro/nanofluidic networks (i.e., channels and structures) are preformed in the substrate. In this embodiment, the nanowires are positioned over the channel using the methods described supra (Step 1). The positioned nanowire is sandwiched between a thin polymer and the substrate and pressure is applied to achieve either complete or partial breakage of the nanowire across the channel (Step 2). The micro-contacts are deposited on the substrate surface and the coverplate is bonded to enclose the nanofluidic device (Step 3). If only partial nanogap formation is achieved, complete breakage is formed by subsequent electrical breakdown, chemical etching, or other suitable means (Step 4).

Nanogaps can also be fabricated by methods known in the art, including, e.g., scanning probes, wire crossings, template-synthesized materials, shadow mask evaporation, mechanical break junction techniques, electroplating, and local oxidative cutting of carbon nanotubes (Chen et al., "On-Wire Lithography-Generated Molecule-Based Transport Junctions: A New Testbed for Molecular Electronics," *J. Am. Chem. Soc.* 130(26):8166-8168 (2008); Hu et al., "A Self-Assembled Nano Optical Switch and Transistor Based on a Rigid Conjugated Polymer, Thioacetyl-End-Functionalized Poly(para-phenylene ethynylene)," *J Am. Chem. Soc.* 127:2804-2805 (2005); Kushmerick et al., "Effect of Bond-Length Alternation in Molecular Wires," *J. Am. Chem. Soc.* 124:10654-10655 (2002); Mbindyo et al., "Synthesis and Assembly of Nanowires for Molecular Electronics," *Abstracts of Papers of the Am. Chem. Soc.* 223: 155-PHYS (2002); Mbindyo et al., "Template Synthesis of Metal Nanowires Containing Monolayer Molecular Junctions," *J. Am. Chem. Soc.* 124:4020-4026 (2002); Reed et al., "Conductance of a Molecular Junction," *Science* 278:252-254 (1997); Tang et al., "Encoding Molecular-Wire Formation Within Nanoscale Sockets," *Angew. Chem. Int. Ed.* 46:3892-3895 (2007); Xu & Tao, "Measurement of Single-Molecule Resistance by Repeated Formation of Molecular Junctions," *Science* 301:1221-1223 (2003), which are hereby incorporated by reference in their entirety).

Micro-contact pads are formed on substrate surfaces as a means for coupling the nanowires or sensing electrodes to external electronic components that will transduce the signals detected by the electrodes. The micro-contact pads can be formed using an electroless deposition process with noble metal nanoparticles patterned onto the substrate to serve as a "seed" layer to allow for the electroless deposition of thin films of Au (gold), as an example, only where the nanoparticles have been positioned.

Figures 29A, 29B:
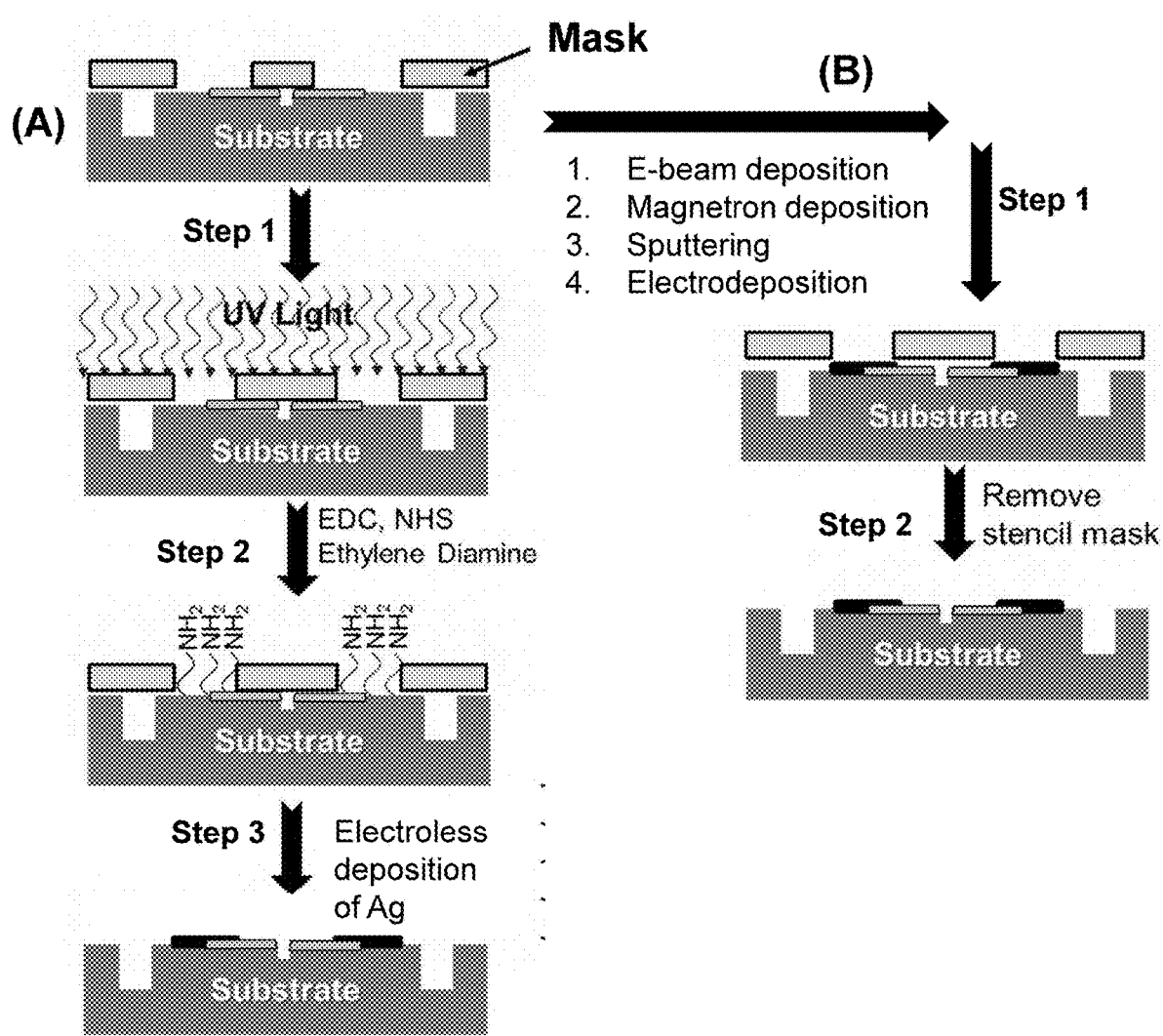
FIGS. 29A-29B schematically illustrate alternative processes for forming the microcontact pads that couple the nanosensing electrodes of the flight time sensor to external electronic components.

The process of micro-contact pad formation is depicted in FIGS. 29A and 29B using two different possible process strategies. For the strategy depicted in FIG. 29A, the polymer substrate, following NIL to form the fluidic network and positioning of the nanowires and gap formation, is UV exposed (254 nm) through a conventional photomask (Step 1). This generates carboxylic acids at only sites where the polymer was irradiated with the UV light. In Step 2, the entire wafer is reacted with ethylenediamine in the presence of EDC/NHS—this forms amine terminated groups by generating an amide bond between the surface carboxylic acids and one amine terminus of ethylene diamine. Amine terminated groups are formed only at sites that were exposed to the UV radiation. Next, the wafer is soaked in a solution containing Ag nanoparticles (Step 3), which form strong complexes with amine groups as well established in the literature. The Ag nanoparticles do not adhere to the polymer substrate not exposed to the UV radiation due to the hydrophobicity of these surfaces and the lack of anchoring points, in this case amine groups. The final step involves placing the wafer in a Au electroless plating bath and forming the desired Au-based microcontact pads.

As depicted in FIG. 29B, following placement of the photomask over the polymer substrate, various direct deposition techniques can be used to form the metal micro-contacts that are well noted for those trained in the art (Step 1). These techniques include, but are not limited to, electron beam deposition, sputtering of metal targets, or magnetron deposition. Following deposition, the stencil mask is removed (Step 2).

Figure 30A:
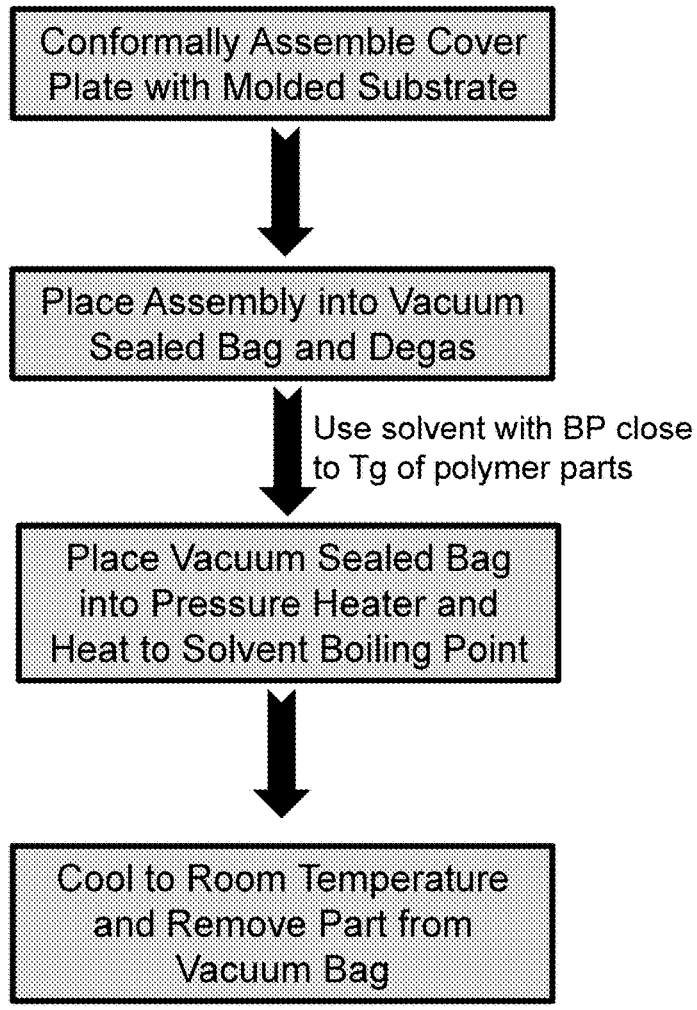
FIGS. 30A-30C show a process for thermally assembling a cover plate to the biomolecular processor while minimizing structural deformation.
Figure 30B:
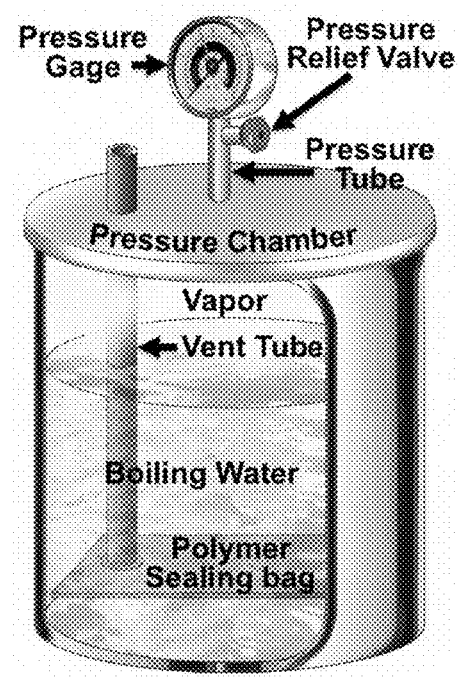
Figure 30C:
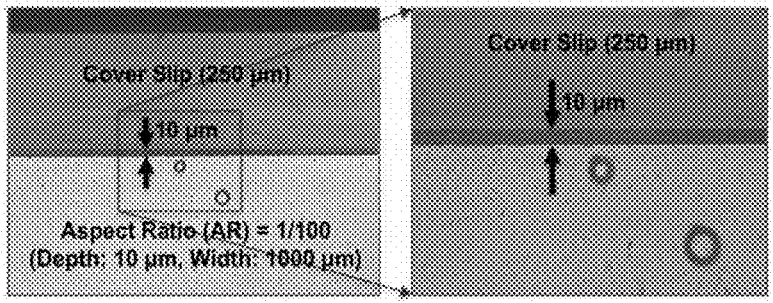

The final step in the fabrication process of the biomolecular processor of the present invention involves bonding of a coverplate to enclose the micro/nanofluidic device. The coverplate bonding procedure is depicted in FIG. 30A. The process involves assembling the coverplate with the molded substrate and placing the assembled product into vacuum sealed bags. Vacuum sealing minimizes structure deformation through the entire thermal process. The degassed vacuum sealed bag is placed in a pressure heater (FIG. 30B), heated to the solvent boiling point, which is near the glass transition temperature of the substrate and cover plate and following bonding, the assembly is then cooled. Boiling solvent provides uniform temperature and vapor pressure, which ensures pressure evenly distributed over the entire device. Results using this process show no structural deformation for bonding cover plate to low-aspect ratio microstructures, even at the nanometer scale (FIG. 30C).

Figure 31:
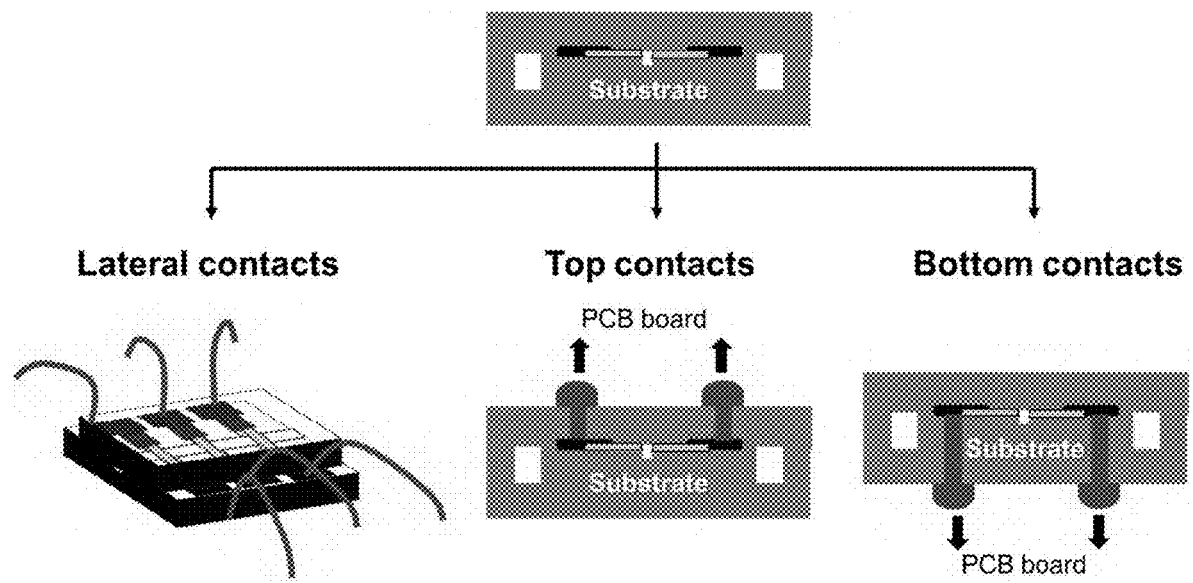
FIG. 31 depicts the process of making various electrical connections between the micro-contact pads and a printed circuit board (PCB) with on-board signal processing electronics.
Figure 32:
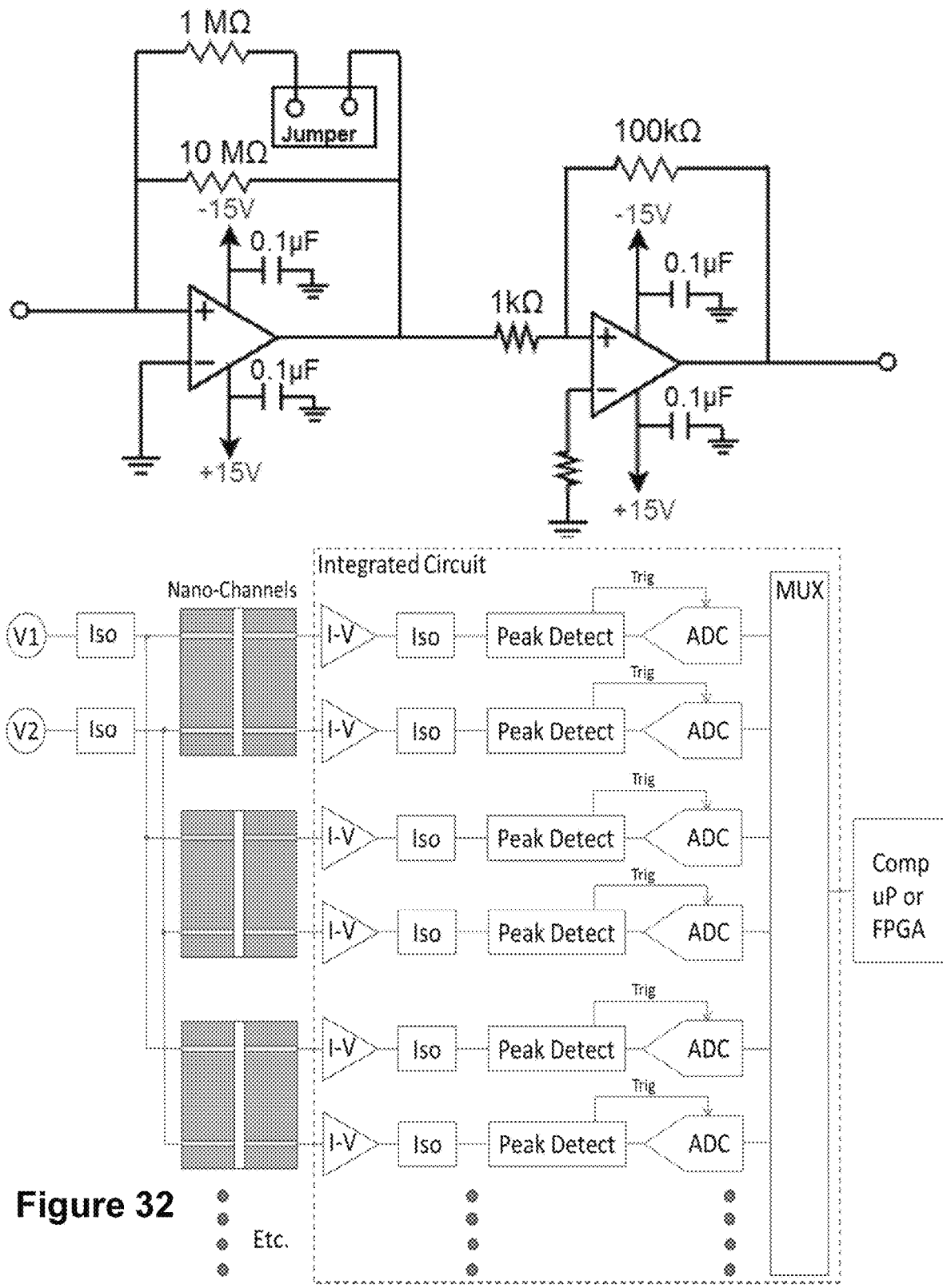
FIG. 32 shows the electronics of the biomolecular processor of the present invention.

The micro-contacts in the assembled device can be interconnected to the appropriate signal-processing electronics shown in FIG. 32 using either lateral, top or bottom electronic connections (FIG. 31). Lateral connections are made by sealing wires to the micro-contacts directly on the nanosensing device. Top or bottom connections have metal contacts that are made vertical to the micro-contacts and contained on additional electronic chips described in FIG. 32. The electronic components necessary for signal processing are poised on printed circuit boards (PCBs) using techniques common to those well trained in the art.

The equivalent circuit for the integrated dual electrode nanogap device is shown in FIG. 32. The major contributors to the electrical readout are the nanogap resistance ($R_N$), capacitance ($C_{ne}$) of the nanoelectrode surface in contact with the buffer and the electrical resistance of the nanoelectrode ($R_{ne}$).

Because the nanogaps are connected by $R_2$, the result is perturbations across the entrance nanogap will be simultaneously observed across the exit nanogap through $R_2$. Also, the current produced across each nanogap becomes divided between each one in a ratio that is indeterminate and varying at different times. Therefore, it is necessary to design an electronic circuit that prevents cross talk between both nanogaps through $R_2$ by isolating (floating) the common across one nanogap from the other (see FIG. 32). To achieve this, two Current-to-Voltage (I-E) converters with two independent floating (±15V DC) power supplies are used. Furthermore, to ensure effective isolation of the amplification end of the system from the digitization end, integrated linear opto-isolators (optocouplers) before and after the A/D and D/A converters are used. Opto-isolators are electronic devices designed to transfer electrical signals from their input to the output ends by utilizing light. They provide coupling with electrical isolation and prevent changes at one end of the circuitry from affecting the other. Each opto-isolator circuitry comprises an opto-chip and four operational amplifiers. Plastic shielded BNC cables and connectors are used in all connections between the digitizer and the I-E converter.

A core component of an I-E converter is the preamplifier. Although any current meter should have low input impedance, all electronic components in the I-E converter must possess high input impedances because the currents to be measured are very small (typically pico-amps; pA). Two-stage amplifiers can be used to achieve a gain of 1,000 and maintain a high bandwidth (~80 kHz). A digitally selectable feedback capacitor, $C_F$ (1 pF) can also be connected in parallel to $R_f$ to prevent any oscillation. The non-inverting input of the amplifier is connected to the nanogap electrodes through a shielded triaxial cable, which provides the command voltage, received the output current and shielding the signal line from any capacitive coupling from external noise. Shielding from external noise is achieved using a dual Faraday cage connected to the common of one amplifier and isolated from the other.

The above circuit design can be multiplexed in a single chip using practices common to those well versed in the art (see FIG. 32). To minimize data storage space, a peak detection circuit is used in a single chip with the peak amplitude also recorded. The multiplexing chip can be interfaced to a field programmable gate arra (FPGA) to process the output from this multiplexing chip.

EXAMPLES

The following examples are provided to illustrate embodiments of the present invention but they are by no means intended to limit its scope Materials and Methods for Examples 1-5

The following example and simulation results represent a process for flight time identification of a single mononucleotides using electrochromatography. The CHARMM27 force field (Foloppe & MacKerell, "All-Atom Empirical Force Field for Nucleic Acids: I. Parameter Optimization Based on Small Molecule and Condensed Phase Macromolecular Target Data," *J. Comput. Chem.* 21:86-104 (2000), which is hereby incorporated by reference in its entirety) was used for the dNMP and ion interactions with the rigid CHARMM TIP3P model for water. The short range cutoff for the electrostatics was 1.0 nm. The Lennard-Jones interactions were switched to zero in the interval between 0.8 to 1.0 nm. The 3-dimensional particle-particle particle-mesh method corrected for slab geometry (Yeh & Berkowitz, "Ewald Summation for Systems with Slab Geometry," *J Chem. Phys.* 111:3155-3162 (1999), which is hereby incorporated by reference in its entirety) with the length in the non-periodic direction three times the simulation box length in that direction was used for long range electrostatic interactions.

The deoxynucleotide monophosphates or dNMPs (dAMP, dCMP, dGMP, dTMP) with a phosphate group on their 5' end can be produced from the cutting of an intact double-stranded or single-stranded DNA using, for example, X-exonuclease for double-stranded DNA. Based on the optimal pH for enzyme activity of 7.5, the dNMPs were simulated as non-protonated because their pKa's are approximately 6.8 (Nucleic Acids in Chemistry and Biology; Blackburn, Eds.; IRL Press:Oxford, (1990), which is hereby incorporated by reference in its entirety), giving them a net charge of −2e, where e is the electron charge. The CHARMM27 topology file does not contain a terminal segment for DNA with a non-protonated phosphate on the 5' end. Patches are used to modify an existing topology by adding or subtracting atoms and modifying partial charges. The topology file does contain terminal patches for DNA with a protonated phosphate on the 5' end, a protonated phosphate on the 3' end, and a non-protonated phosphate on the 3' end. Therefore, the difference in partial charges on the affected atoms between the non-protonated and protonated 3' versions was added to the partial charges for the non-protonated 5' versions. The affected atoms included only the phosphate group and the carbon atom directly attached to it.

To enable molecular dynamic (MD) simulations using deoxynucleotide monophosphates with a non-protonated phosphate group on the 5' end the following "patch" was added to the existing CHARMM forcefield:

```
PRES 5PO3   -2.00 ! 5'terminal PHOSPHATE patch
                  ! same shifts in charge as between 3PHO and 3PO3
GROUP
ATOM C5' CN8B  -0.18
ATOM H5' HN8    0.09
ATOM H5" HN8    0.09
ATOM P   P      1.10
ATOM O1P ON3   -0.90
ATOM O2P ON3   -0.90
ATOM O5' ON2   -0.40
ATOM O3P ON3   -0.90
BOND O3P P
ACCE O3P P
! Built in B-DNA-like conformation (NF)
BILD C4' C5' O5' P    0.0000 000.00 -146.00 000.00 0.0000
BILD C5' O5' P O3P    0.0000 000.00  -46.90 000.00 0.0000
BILD O3P O5' *P O1P   0.0000 000.00 -115.82 000.00 0.0000
BILD O3P O5' *P O2P   0.0000 000.00  115.90 000.00 0.0000
```

Figures 33A, 33B, 33C, 33D:
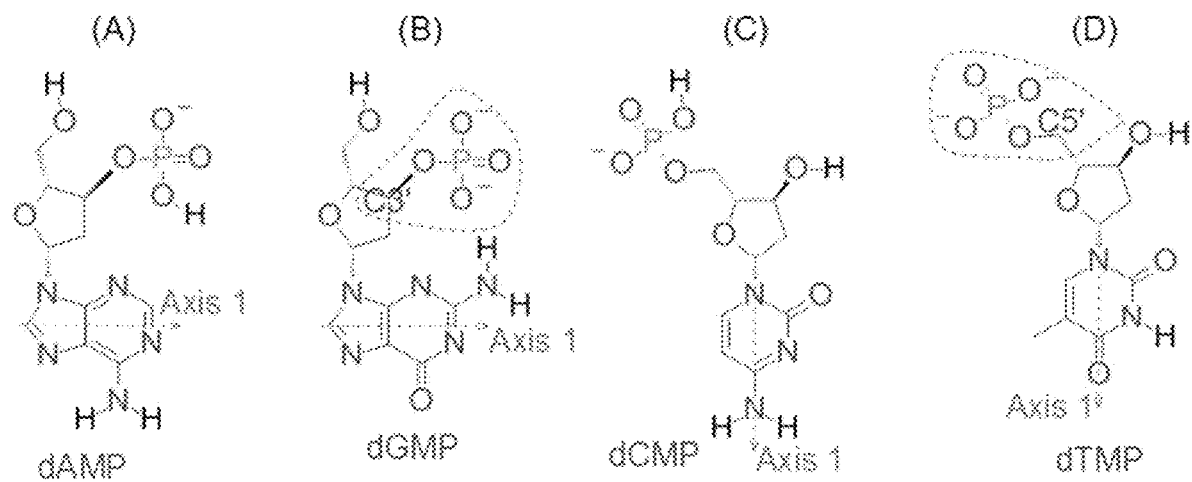
FIGS. 33A-33D show dNMP structures containing the four nucleobases.

FIG. 33 shows dNMPs with all four of the termini and the affected atoms labeled.

The slit walls were defined by two planes, parallel to the xy plane and located at z=±1.5 nm; the centers of the wall atoms are located at z≤−1.5 nm (bottom) and z≥1.5 nm (top). The slit walls were constructed by performing a simulation of a bulk fluid composed of atoms with Lennard-Jones 12-6 parameters for a carbon atom ($\varepsilon$carbon-carbon=0.11 kcal/mol, $\sigma$carbon-carbon=0.4/21/6 nm). The mass of the atoms was increased from 12.011 to 14.30226 amu so that it was equal to the mass of the average mass of the atoms in a united atom (no hydrogen atoms, but increased mass of atoms that would have hydrogen atoms attached to them) representation of PMMA. This simulation was run at 5000 K, to ensure that it was a fluid, and at a density near that of amorphous PMMA. The size of the simulation box in the x and y directions was chosen to be 5.0 nm in order to match the desired size of the slit walls. The slit wall initial configurations were taken from 5.0×5.0×1.2 nm3 rectangular regions of this fluid. If the atom centers were inside the rectangular region, they were included in the wall. This resulted in surfaces that were atomically smooth (roughness less than the size of an atom), but heterogeneous. Each set of slit walls was taken from different times during the fluid simulation spaced 10 ps apart. A slit width of 3 nm was chosen to avoid wasting simulation time allowing the dNMPs to diffuse around in the center of the slit for long periods, although real channels with dimensions smaller than 5 nm have been fabricated (Menard et al., *Nano Lett.* 11: 512-517 (2011), which is hereby incorporated by reference in its entirety). It should also be noted that using small, completely hydrophobic nanoscale geometries is not practical due to the difficulty for water to enter them. The slit walls were not chosen to be physically realistic, but as a simple system for this initial study.

Figures 34A, 34B:
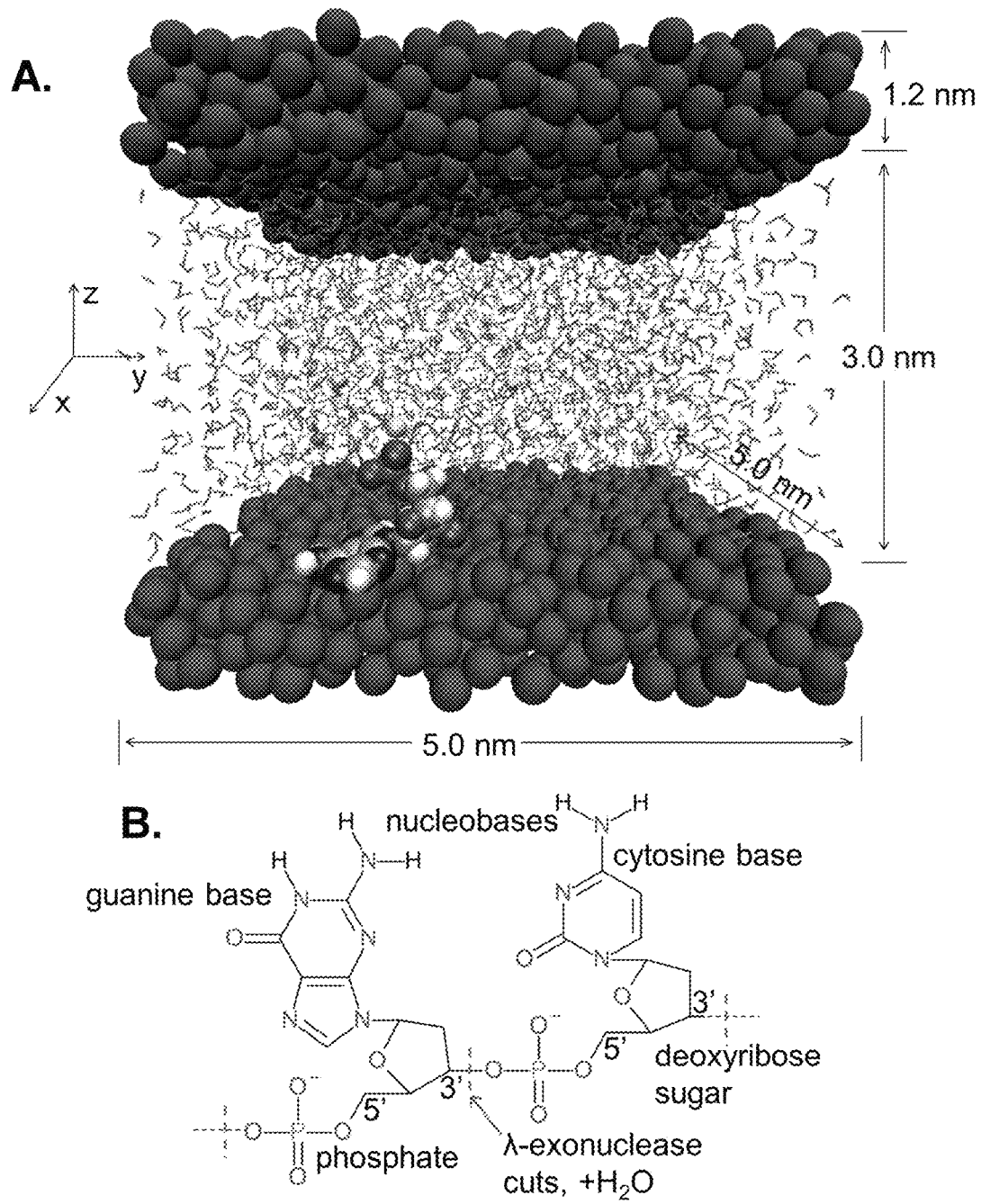
FIG. 34A-34B shows the system used for both the equilibrium and non-equilibrium simulations and the chemical structure of DNA.

Once the walls were constructed, the dNMPs were moved between the slit walls and water and ions were added using VMD. 38 NPT simulations could not be performed in LAMMPS for the geometry that was used, so the amount of water was determined by trial and error. The Solvate function in VMD was used to add water with the settings: boundary=2.4, x and y bounds=±25.65 Å, z bounds=±15 Å. These settings were determined by trial and error to get a reasonable bulk density of water (center of slit) in equilibrium simulations containing only water and the slit walls. The equilibrium bulk water density was about 1.015 g/cm3. After the dNMP was solvated, four water molecules were removed and replaced with three sodium ions and one chloride ion using the Autoionize function in VMD. The simulation system used for both the equilibrium and non-equilibrium simulations and the chemical structure of DNA is shown in FIGS. 34A and 34B.

The following describes the methods and general parameters used in carrying out the simulations. The wall atoms were attached to their initial positions by springs with spring constants of 83 860 kcal/mol·nm2. For the flow simulations, only the wall atoms were thermostatted at 300 K using a Berendsen thermostat with a time constant of 0.1 ps. The fluid temperatures during flow at steady state were about 3 K higher than the temperature of the thermostatted walls due to heating of the fluid by viscous flow. For the equilibrium simulations, an additional thermostat was used for the fluid with the same time constant. For each dNMP, three or four simulations were run with different wall configurations to reduce any bias due to particular wall configurations. Flow was induced by applying a constant body force in the x direction (see FIG. 34A), $f_i$, to each atom. The magnitude off was chosen such that $f_i = m_i a$, where $m_i$ is the mass of atom i and a is the acceleration, chosen the same for all atoms. This approach is an approximation to pressure-driven flow (Zhu et al., "Pressure-induced Water Transport in Membrane Channels Studied by Molecular Dynamics," *Biophysical*

Journal 83:154-160 (2002), Carr et al., *IEEE Trans. Nanotechnol.* 10:75-82 (2011), which are hereby incorporated by reference in their entirety) or flow generated by capillary forces (Han et al., *J. Colloid Interface Sci.* 293: 151-157 (2006), which is hereby incorporated by reference in its entirety). The pressure gradient along the direction of flow due to the applied forces $f_i$ on all n atoms of the fluid is given by $$\frac{dP}{dx} = \frac{\sum_{i=1}^{n} f_i}{A_{fluid} L_{box}},$$

where $L_{box}$ is the length of the simulation box along the direction of the externally applied forces (x) and $A_{fluid}$ is the area of the fluid in the plane perpendicular to the direction of the applied forces (yz plane). By choosing a=263.592 nm/ns2, and using the characteristic values for the parameters describing the simulation system (i.e., the number of atoms in the flow region and their mass, the area perpendicular to the flow, and the length of the simulation box) the pressure gradient that drives the flow in the nanoslit is about dp/dx=2.836 bar/nm. The applied forces generate an approximately parabolic velocity profile across the z direction characterized by a maximum flow velocity of about 1.5 m/s. Simulation at such high velocities relative to velocities typical of nanoscale flows is necessary in MD simulations due to the relatively short time that is accessible, usually just few hundred nanoseconds. As discussed later, despite the very high velocities, the characteristic parameters describing the adsorption and desorption of dNMPs to and from the wall do not seem to be affected substantially by the flow. The first 15 ns of each flow simulation were discarded from the analysis to allow for steady state conditions to be achieved. In the equilibrium simulations, a 1 ns equilibration period was discarded.

Algorithm for Determination of Nucleotides Adsorption and Desorption Events.

Figure 35:
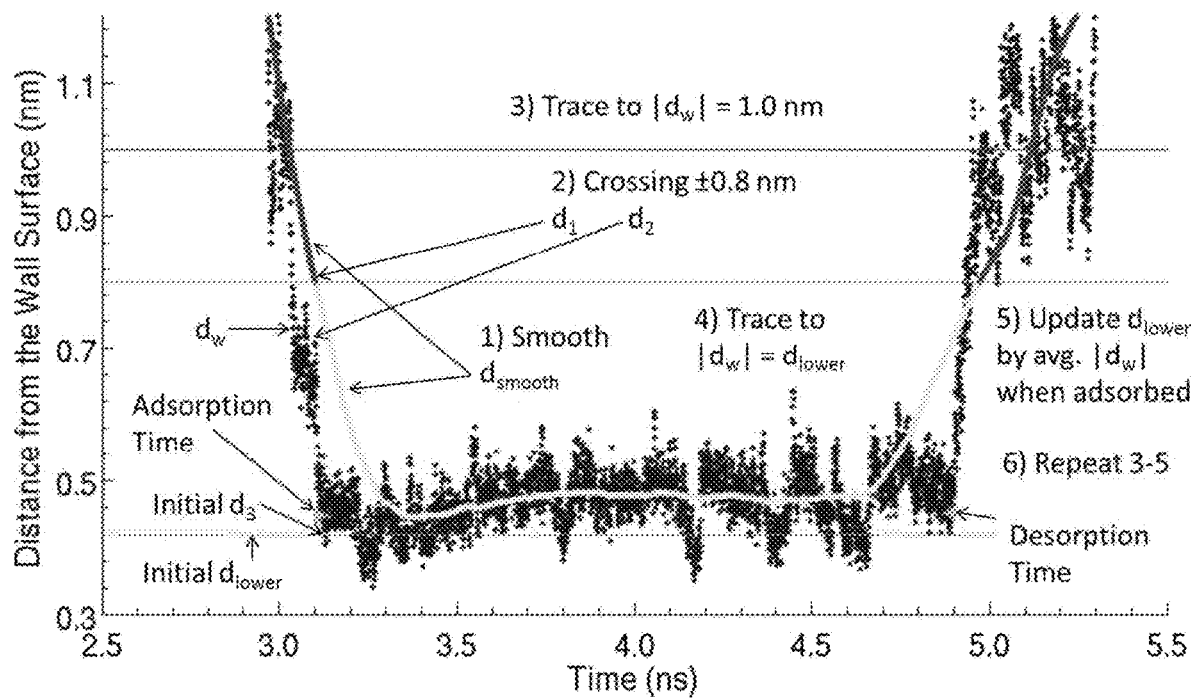
FIG. 35 depicts the steps in the algorithm to determine adsorption and desorption times. For calculation of the energy between the dNMPs and the wall during adsorption periods, a different definition was used for adsorption. If the energy was less than −2.0 kcal/mol, then the dNMP was considered adsorbed.
Figure 36:
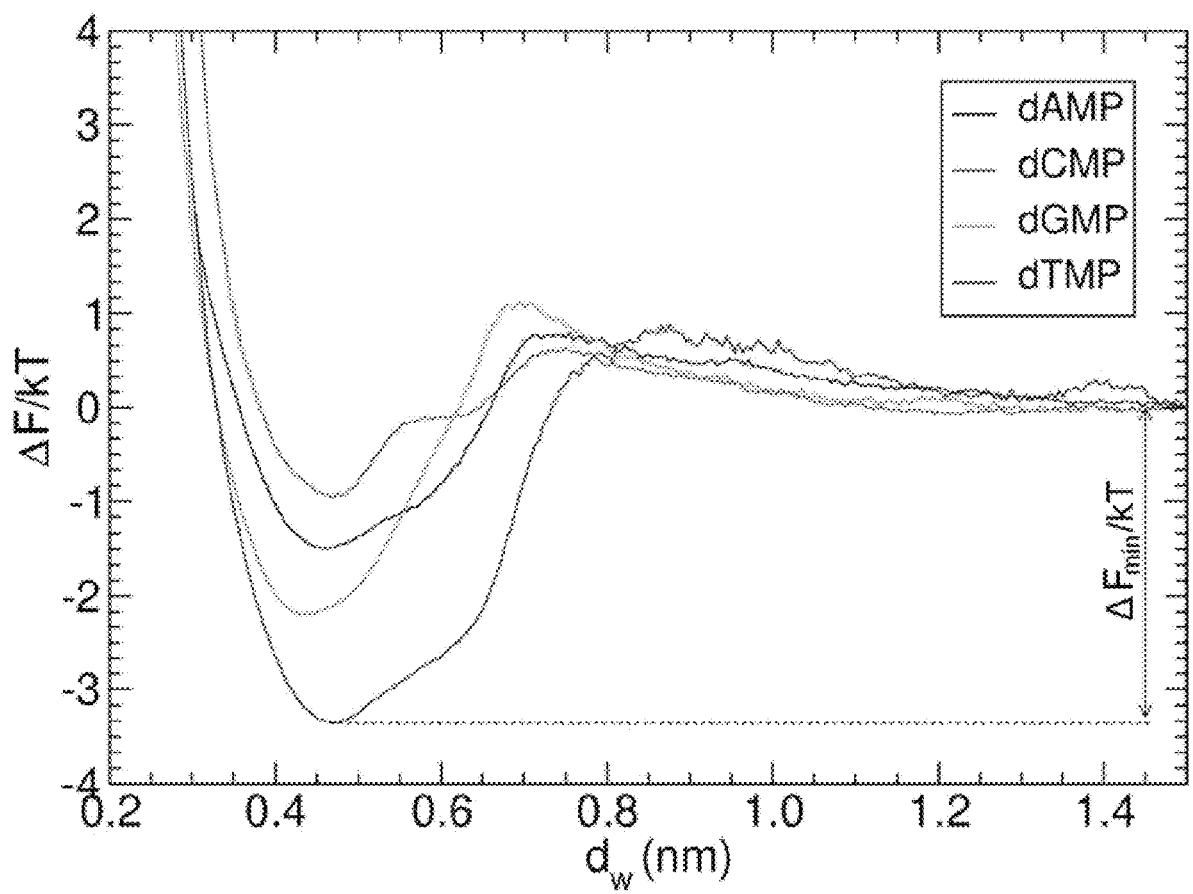
FIG. 36 shows the free energies of the four dNMPs as a function of the distance from the hydrophobic walls, $d_w$. These curves are averages over all the different sets of wall configurations.

The algorithm used for determining adsorption and desorption times is illustrated in FIG. 35 for a single adsorption and desorption event from the lower wall, and was carried out as follows. First $d_w$ was smoothed (labeled $d_{smooth}$) using a running average of length 0.5 ns. The points labeled $d_1$ were defined where $d_{smooth}$ crossed ±0.8 nm. This is approximately where the PMF curves begin to flatten out (FIG. 36). These points were assumed to precede an adsorption event or follow a desorption event depending on which direction they crossed the ±0.8 nm boundaries. The rest of the steps used the original, non-smoothed $d_w$. A set of points (labeled $d_2$) were defined with the same times as for $d_1$, but corresponded to $d_w$. Starting from $d_2$, the data were traced forward (desorption) or backward (adsorption) in time until the value of $d_w \geq 1.0$ nm, far from the minima in the PMF curves (FIG. 36). The direction of the tracing was then reversed and performed until $d_w \leq d_{upper}$ (when approaching the upper wall), $d_w \leq d_{lower}$ (when approaching the lower wall), or until the beginning or end of the data was reached. In most cases, $d_{upper}$ and $d_{lower}$ were set to 0.42 nm, which was slightly closer to the walls than the global minima in the PMF curves (FIG. 36). In some cases, one of them had to be modified slightly so that obvious adsorption and desorption events were not missed. This was necessary because the configuration of atoms in each wall was different, so the adsorption on each wall was slightly different. Of course an algorithm might be devised to determine the initial $d_{upper}$ and $d_{lower}$ such that they would never have to be manually adjusted to capture the events properly. However, the exact starting values did not influence the final values of adsorption and desorption times. The points resulting from this tracing were denoted as $d_3$. If there were repetitions in $d_3$ or times equal to the first or last time in the data set, these points were eliminated because they corresponded to $d_2$ points that were not near adsorption or desorption events. After the elimination of points, the averages of $d_w$, while the dNMP was adsorbed to the upper and lower walls were calculated using $d_3$ as the points of adsorption and desorption. The tracing steps were then repeated except that $d_{upper}$ and $d_{lower}$ were replaced with the averages that were just calculated, $d_3$ was updated, and the average of $d_w$ while adsorbed was calculated again. After a couple of iterations, $d_3$ converged to a steady value. The smoothing and choice of $d_w$, =0.8 nm to determine $d_1$ eliminated short time or distance departures from the surface from being classified as desorption events and the initial choice of $d_{upper}$ and $d_{lower}$ to determine the initial $d_3$ prevented events where the dNMP bounced off of the surface from being classified as adsorption events Uncertainty Estimation of the PMFs.

The uncertainties in the PMFs, shown in FIG. 36, were calculated by dividing the production time in each bin into three pieces. Furthermore, for each mononucleotide three PMF curves were then generated from these pieces. This allowed to evaluate the mean and the standard deviations from the mean for each point on the resulting averaged PMF curve. In order to estimate the uncertainty in the positions of the maxima in the four PMFs and in the average adsorption free energies, the following numerical error propagation methodology was used: i) assumed that the mean and standard deviations of the mean for each point on the curve defined a normal distribution for each bin, ii) 100,000 random samples from the distributions for each point were taken to generate 100,000 PMF curves. The uncertainty in the positions of the maxima in the PMFs and the average adsorption free energies were obtained from the 100,000 free energy curves from 100,000 maxima and average adsorption free energies calculated from those curves. The uncertainties were taken to be two times the standard deviations.

For the velocity in the flow direction and the angles, which were calculated only while the dNMPs were adsorbed to the wall or not, the uncertainties were estimated as follows. Block averaging was used, but not in the usual way where every block has an equal length. Instead each adsorption or desorption period for all simulations for each dNMP was taken as a separate block. The mean of the data in each block was used to get the block averages, $x_i$. The overall mean was obtained by taking a weighted average of the n block averages where the weights, $w_i$ were the number of data points in each block. The weighted mean and variance of the $x_i$ were calculated using $$w'_i = w_i / \min(w_i) \tag{S1}$$

$$\bar{x}_w = \sum_{i=1}^{n} w'_i x_i \bigg/ \sum_{i=1}^{n} w'_i \tag{S2}$$

$$s_w^2(x_i) = \frac{\sum_{i=1}^{n} w'_i (x_i - \bar{x}_w)^2}{\left(\sum_{i=1}^{n} w'_i\right) - 1} \tag{S3}$$

The variance of the weighted mean was calculated dividing by the effective base (b) which reduces to n in the case of equal weights, and the uncertainty (u) was taken as two times the standard deviation of the weighted mean.

$$s^2(\bar{x}_w) = s_w^2(x_i)/b \quad (S4)$$

$$b = \left(\sum_{i=1}^{n} w_i\right)^2 / \sum_{i=1}^{n} w_i^2 \quad (S5)$$

$$u(\bar{x}_w) = 2\sqrt{s^2(\bar{x}_w)} \quad (S6)$$

The overall mean velocity in the flow direction and its uncertainty were calculated using $$\bar{v} = f_{ads}\bar{v}_{ads} + (1-f_{ads})\bar{v}_{doz} \quad (S7)$$

$$u(\bar{v}) = \sqrt{2f_{ads}^2 s^2 + (1-f_{ads})^2 s^2(\bar{v}doz)} \quad (S8)$$

where fads is the adsorption time for all simulations divided by the total time for all simulations for each dNMP.

The mean fraction of time adsorbed, mean frequency of adsorption events, and their uncertainties were also calculated with equations S1-S6. The only difference was that the "blocks" were entire simulations for each dNMP, the weights (wi) for the fraction of time adsorbed were the total simulation times, and the weights for the frequency of adsorption were the total distances traveled in the flow direction. For the dNMP-wall energy while adsorbed, block averaging with equal block lengths was used (all wi equal in equations S1-S6). The block lengths were 1300 points which corresponded to 0.52 ns.

Axis 2 Angle with the Wall Surface.

Figure 41:
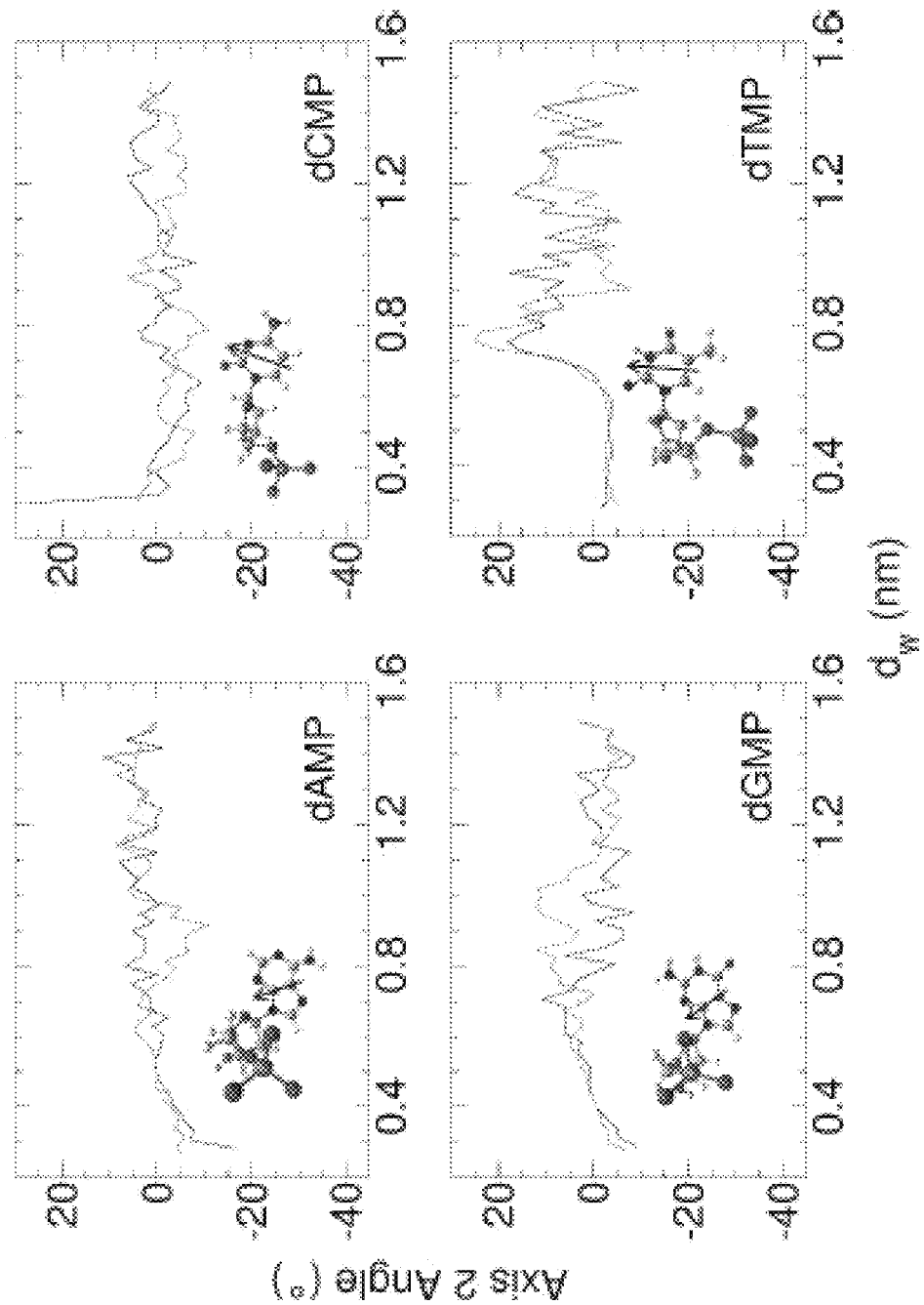
FIG. 41 shows the angle of Axis 2 with the surface plane as a function of $d_w$, for adsorption in the equilibrium case (gray) and non-equilibrium case (black). The arrows on the structures indicate the direction the axis points. Negative is pointing away from the center plane of the slit ($d_w$=1.5 nm).
Figure 42:
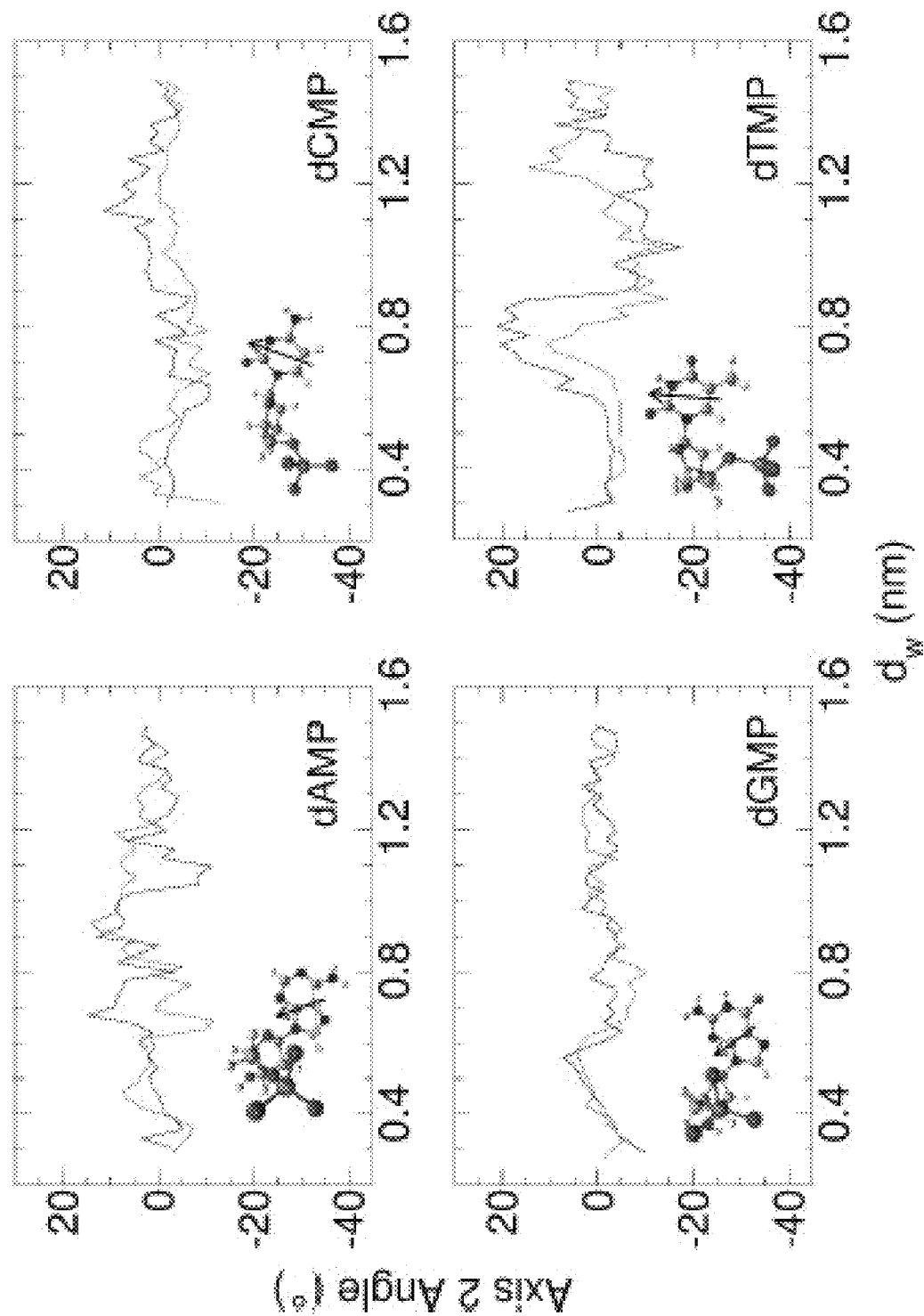
FIG. 42 show the angle of Axis 2 with the surface plane as a function of $d_w$, for desorption in the equilibrium case (gray) and non-equilibrium case (black). The arrows on the structures indicate the direction the axis points. Negative is pointing away from the center plane of the slit ($d_w$=1.5 nm).

The average angles of Axis 2 defined in FIG. 35 with the nearest wall surface plane as a function of dw are shown in FIG. 41 for adsorption and FIG. 42 for desorption in both the equilibrium and non equilibrium cases. Table 7 (below) shows the average Axis 2 angles calculated while the dNMPs were adsorbed, regardless of whether this was during an adsorption or desorption period. The adsorption and desorption curves for a given nucleotide shown in FIG. 41 and FIG. 42 for Axis 2 are not easily distinguishable from each other because the change in the angles is comparable to the noise. When the nucleotides are near the wall during adsorption, the side of the dNMP that is most hydrophobic is generally closer to the wall; dTMP is an exception. The non-planar methyl group causes the side of the nucleotide it is on to be farther from the wall even though the methyl group is hydrophobic. The orientation of Axis 2 near the wall is not as strong during desorption. Given the level of noise, there are no significant minima or maxima in the Axis 2 angle for dAMP, dCMP, or dGMP. For dTMP, the hydrophobic methyl-surface interaction causes a significant maximum in the Axis 2 angle during adsorption and desorption. The dTMP maximum angle for desorption is smaller than for adsorption in the equilibrium case. This maximum is also smaller in the equilibrium case compared to the non-equilibrium case. For the desorption of dTMP, there is also a minimum in the Axis 2 angle following the maximum.

Determination of the Required Channel Length to Separate Time of Flight Distributions.

The details for the determination of the minimum channel length, L, required to separate the mononucleotides time of flight (TOF) distributions are as follows. No prior form for the time of flight distributions was assumed. Instead, the continuous distribution functions (CDF) were estimated by numerical integration of the probability histograms of the times of flight distribution over 0.5 nm ($d^{TOF}$) long trajectory segments using the trapezoidal rule. Subsequently, the points where each CDF reached the values 0.00135 (μ−δ) and 0.99865 (μ+δ$^+$), where μ is the mean TOF, were estimated by linear interpolation. These points define the width of the sample distributions. In the equations below, these points were considered the edges of the TOF distributions. The numbers 0.00135 and 0.99865 define how much overlap is allowed and can be changed to get more or less accuracy in separating the distributions. For the sake of simplicity, in this analysis the DTOF$_{0.5 \times N}$, defined in the main text, were used in the normalized form (that is the values of the random variables, TOFs, were all divided by N). Consequently, in the normalized form the DTOF$_{0.5 \times N}$ for any nucleotide α is characterized by the mean TOF value, μα, and has a width that decrease with the square root of N. The minimum values of $N_q$, required so that the distributions for each pair of nucleotides (α,β) do not overlap are given by equation (S11), which is a combination of equations (S9) and (S10). The minimum required channel length (L) is given by equation (S12).

$$\mu_\alpha + \frac{H[\mu_\beta - \mu_\alpha]\delta_\alpha^+ - H[\mu_\alpha - \mu_\beta]\delta_\alpha^-}{\sqrt{N_\alpha}} = \quad (S9)$$

$$\mu_\beta + \frac{-H[\mu_\beta - \mu_\alpha]\delta_\beta^- + H[\mu_\alpha - \mu_\beta]\delta_\beta^+}{\sqrt{N_\beta}},$$

$$N_\beta = \frac{d_\alpha^{TOF}}{d_\beta^{TOF}} N_\alpha = N_\alpha = N_{\alpha,\beta}, \quad (S10)$$

$$N_{\alpha,\beta} = \frac{H[\mu_\beta - \mu_\alpha](\delta_\beta^- + \delta_\alpha^+)^2 + H[\mu_\alpha - \mu_\beta](\delta_\alpha^- + \delta_\beta^+)^2}{(\mu_\alpha - \mu_\beta)^2}. \quad (S11)$$

$$L = \max[N_{\alpha,\beta} d^{TOF}]. \quad (S12)$$

In these equations, μ is the mean, δ− and δ+ are the distances from the mean to the points where the CDF is equal to 0.00135 and 0.99865. H[x] is the Heaviside step function (H[x]=0 for x≤0 and H[x]=1 for x>0), which is used to distinguish the two possible arrangements of the distributions; either the mean of the distribution for type α is smaller than for type β ($\mu_\alpha < \mu_\beta$), or the mean of the distribution for type α is larger than for type β ($\mu_\alpha > \mu_\beta$). The number of samples required for nucleotide types α ($N_\alpha$) and β ($N_\beta$) have many possible combinations which satisfy equation (S1). However, they are constrained by the fact that the two nucleotides must travel the same overall distance ($d_\beta^{TOF} N_\beta = d_\alpha^{TOF} N_\alpha$). Since distances used to calculate times of flight for types α ($d_\alpha^{TOF}$) and β ($d_\beta^{TOF}$) are both 0.5 nm ($d^{TOF}$), then $N_\alpha = N_\beta = N_{\alpha,\beta}$. $N_{\alpha,\beta}$ is now the only unknown in equation (S9), and solving for it gives equation (S11). The maximum value of $N_{\alpha,\beta}$ times $d^{TOF}$ is the required channel length.

Example 1—Equilibrium Simulations and Adsorption Free Energy

The goal of the equilibrium simulations was to investigate the mechanism and the energetics of individual dNMPs adsorption and desorption in the absence of flow. For each dNMP several simulations were run with different wall configurations (see Table 8). Each simulation lasted for about 65 ns, while the total simulation time for all four dNMPs and all of the various wall configurations was about 966 ns. The interaction of individual dNMPs with the slit walls is best described by their free energy profiles across the nanoslit. The free energy difference relative to a reference state, ΔF, as a function of a reaction coordinate (potential of mean force or PMF) is related to the probability, Pr, of the dNMP being located at a given value of the reaction coordinate. Because the probability for a dNMP to be adsorbed or desorbed from a smooth surface was of interest, the reaction coordinate was taken as the distance, $d_w$, of the dNMP center of mass from the nearest slit wall plane located at $z=\pm 1.5$ nm. Using the values of $Pr(d_w)$, the free energy profile is given by $$\Delta F(d_w) = -kT\ln\left[\frac{Pr(d_w)}{Pr(d_{w,ref})}\right] \quad (1)$$

where, k is Boltzmann's constant, T is the temperature, and $d_{w,ref}$ is the reference state chosen far from the wall in the center of the nanoslit (z=0).

During the equilibrium simulations, all four dNMPs adsorbed and desorbed from the wall surface multiple times, therefore equation (1) could be applied directly. Biased equilibrium simulations, such as umbrella sampling (Torrie & Valleau, *Chem. Phys. Lett.* 28:578-581 (1974); Novak et al., "Umbrella Sampling Simulations of Biotin Carboxylase: Is a Structure With an Open ATP Grasp Domain Stable in Solution?" *J. Phys. Chem. B* 113:10097-10103 (2009); and Novak et al., "Behavior of the ATP Grasp Domain of Biotin Carboxylase Monomers and Dimers Studied Using Molecular Dynamics Simulations," *Proteins: Struct. Funct. Bioinform.* 79:622-632 (2011), which are hereby incorporated by reference in their entirety), may be required to calculate the free energy in cases when dNMPs adsorb onto the slit surface for time periods comparable to the total simulation time (e.g., longer than a few nanoseconds). The multiple adsorption and desorption events also allowed for different adsorption sites on the heterogeneous surfaces to be sampled, so the ΔF in eq 1 is an average over those different sites. In fact, the dNMPs were mobile in the directions tangential to the wall plane even when adsorbed to a wall which allowed them to sample more of the wall surface. This is an indication that there are not any strong adsorption sites for the dNMPs on the wall surfaces and that there is little variation in adsorption strengths across the surfaces. These are characteristics of the wall surfaces that are desired in order to make time-of-flight-based sequencing feasible. However, the wall surfaces are not made of a real material and are smoother than a real surface. It has been found that adsorption at different sites on amorphous silica surfaces varied in strength from 0 to 10 kT (Carr et al., *J. Phys. Chem. Lett.* 2: 1804-1807 (2011), which is hereby incorporated by reference in its entirety). The variation of dNMP adsorption strengths on PMMA surfaces is the subject of future work.

FIG. 36 shows the profiles of the free energy as function of $d_w$ for all four dNMPs. The profiles are similar and are characterized by the presence of well-defined minima. The existence of potential wells with depths of at most a few times the thermal energy, kT, reflects the fact that the dNMPs adsorb to the hydrophobic walls, but not strongly. The minima for the four curves are approximately located at the same distance, about 0.475 nm from the wall. As discussed in the next section, when dNMPs are adsorbed to the wall and are located in their minimum free energy state two of their main molecular units, the nitrogenous base and the sugar group, are in similar geometrical arrangement with respect to the wall surface, and therefore, they all have their center of mass located at about the same distance from the wall. All four curves show the presence of small barriers, of up to kT, located between the adsorption region and the bulk solvent close to the center of the slit. Here the adsorption region is defined as the region close to the wall in which the dNMP experience pulling force toward the minima of their potential well. As seen in FIG. 36 the outward extent of the adsorption regions for the four nucleotides can be delimited by the locations of the corresponding peaks, $d_w^M$, of the small energy barriers. While the profiles of the free energies and the corresponding global minima, $\Delta F_{min}$, (shown in Table 6), give a direct measure of the strength of dNMPs interaction with the walls, the scalar parameter, $\Delta F_{ads}$, the so called net free energy of adsorption, is more appropriate for a comparison with experiment (Raut et al., "Molecular Dynamics Simulations of Peptide-Surface Interactions," *Langmuir* 21:1629-1639 (2005), which is hereby incorporated by reference in its entirety). From the free energy profile, the net free energy of adsorption, $\Delta F_{ads}$ is obtained by evaluating the weighted sum of the free energies of all states characterizing dNMPs in the adsorbed state as $$\Delta F_{ads} = -\ln\left(\frac{C_{ads}}{C_{bulk}}\right) = \quad (2)$$

$$\int_0^{d_w^M} PD(d_w)\Delta F(d_w)d(d_w) \approx \sum PD_i \Delta F_i (\Delta d_w)_i = \sum Pr_i \Delta F_i$$

In this equation, $\Delta F_{ad}$, and ΔF are expressed in units of kT. $C_{ads}$, is concentration in the adsorption region, and $C_{bulk}$ is concentration in the bulk solution far from the walls. The subscript i denotes the bin number. $(d_w)_i$ is the location of bin i, which has a width of $(\Delta d_w)_i$. $Pr_i$ represents the probability of the dNMP being in a given bin. $PD_i = Pr_i/(\Delta d_w)_i$ represents the normalized probability density in a given bin. Table 6 gives a summary of the relevant quantities characterizing the energetics and the extent of the adsorption regions of dNMPs adsorption to the slit hydrophobic walls.

TABLE 6

The minima of the free energy profiles ($\Delta F_{min}$) for the four dNMPs interacting with the hydrophobic slit walls and their average free energy of adsorption, $\Delta F_{ads}$, together with the position of the free energy maxima ($d_w^M$) used to delimit the adsorption region.

| Nucleotide | $\Delta F_{min}/kT$ | $\Delta F_{ads}/kT$ | $d_w^M$ (nm) |
|---|---|---|---|
| dAMP | −1.6 ± 0.4 | −0.69 ± 0.07 | 0.71 ± 0.09 |
| dCMP | −1.0 ± 0.7 | −0.21 ± 0.05 | 0.71 ± 0.05 |
| dGMP | −2.2 ± 0.7 | −1.19 ± 0.03 | 0.70 ± 0.04 |
| dTMP | −3.4 ± 0.4 | −2.62 ± 0.04 | 0.88 ± 0.03 |

Example 2—Adsorption and Desorption Dynamics

Relating the adsorption and desorption statistical and dynamical properties to other properties such as flight times is of great interest. The analysis of the simulation results indicate that while the dNMPs were adsorbed, the rings of the relatively hydrophobic nucleobases tended to be nearly flat on the surface, the hydrophilic phosphate groups pointed away from the surface, and the sugar also had some contact with the surface (see FIG. 34A). This hydrophobic adhesion of the nucleobases to a surface has been observed previously in simulations of transport of DNA strands through a silicon nitride nanopore (Aksimentiev et al., *Biophys. J.* 87: 2086-

Figure 37:
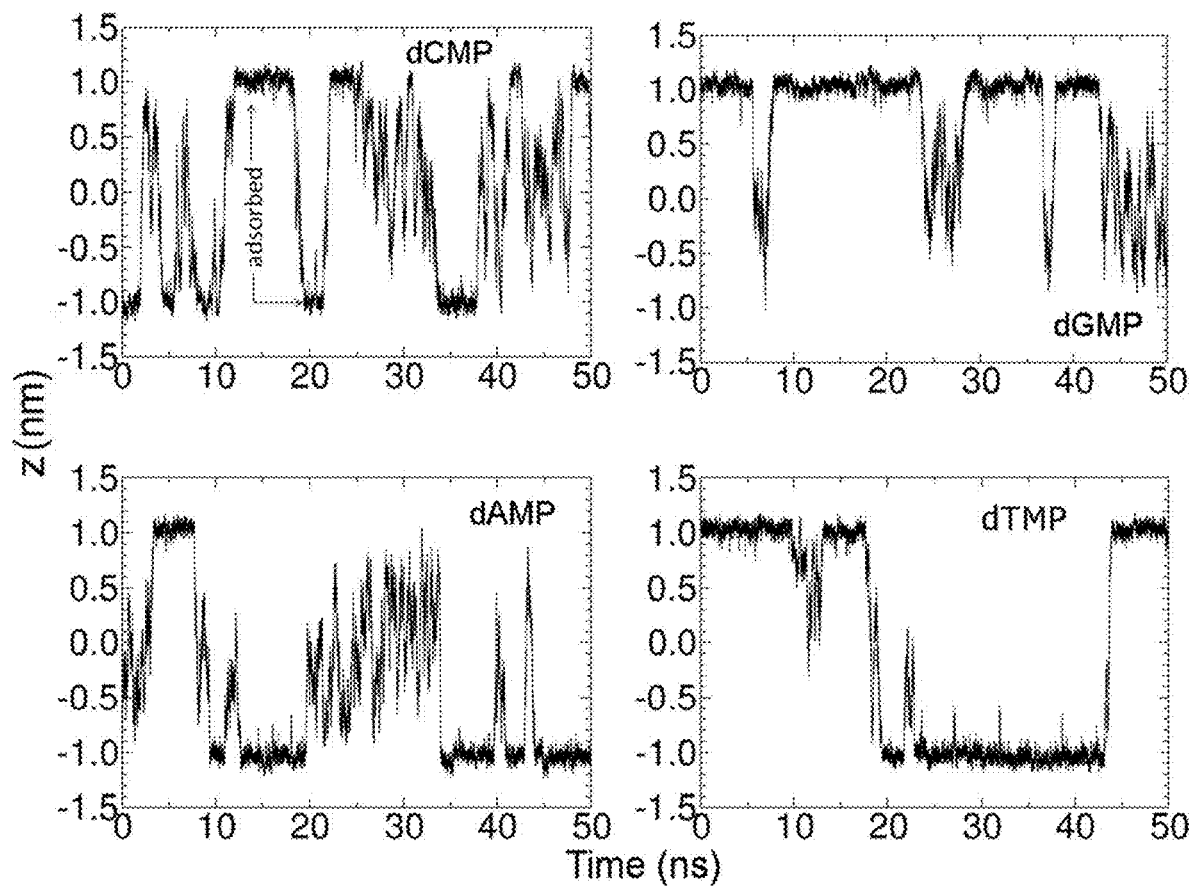
FIG. 37 shows the typical 50 ns trajectories of the center of mass of the dNMPs in the z direction (perpendicular to the wall surfaces)

2097 (2004), which is hereby incorporated by reference in its entirety), and with a grapheme sheet in simulations of the transport of DNA strands through a grapheme nanopore (Wells et al., *Nano Lett.* 12: 4117-4123 (2012), which is hereby incorporated by reference in its entirety). FIG. 37 shows 50 ns segments of the z-component of the trajectories of the dNMPs center of mass during flow simulations. Trajectories for equilibrium simulations are similar. There are clear differences between the trajectories of the four dNMPs as indicated by the differences in the frequency and the length of the adsorption events. In order to quantify the adsorption and desorption statistics, a methodology for determining adsorption and desorption times was introduced and is explained in detail above.

Figure 38:
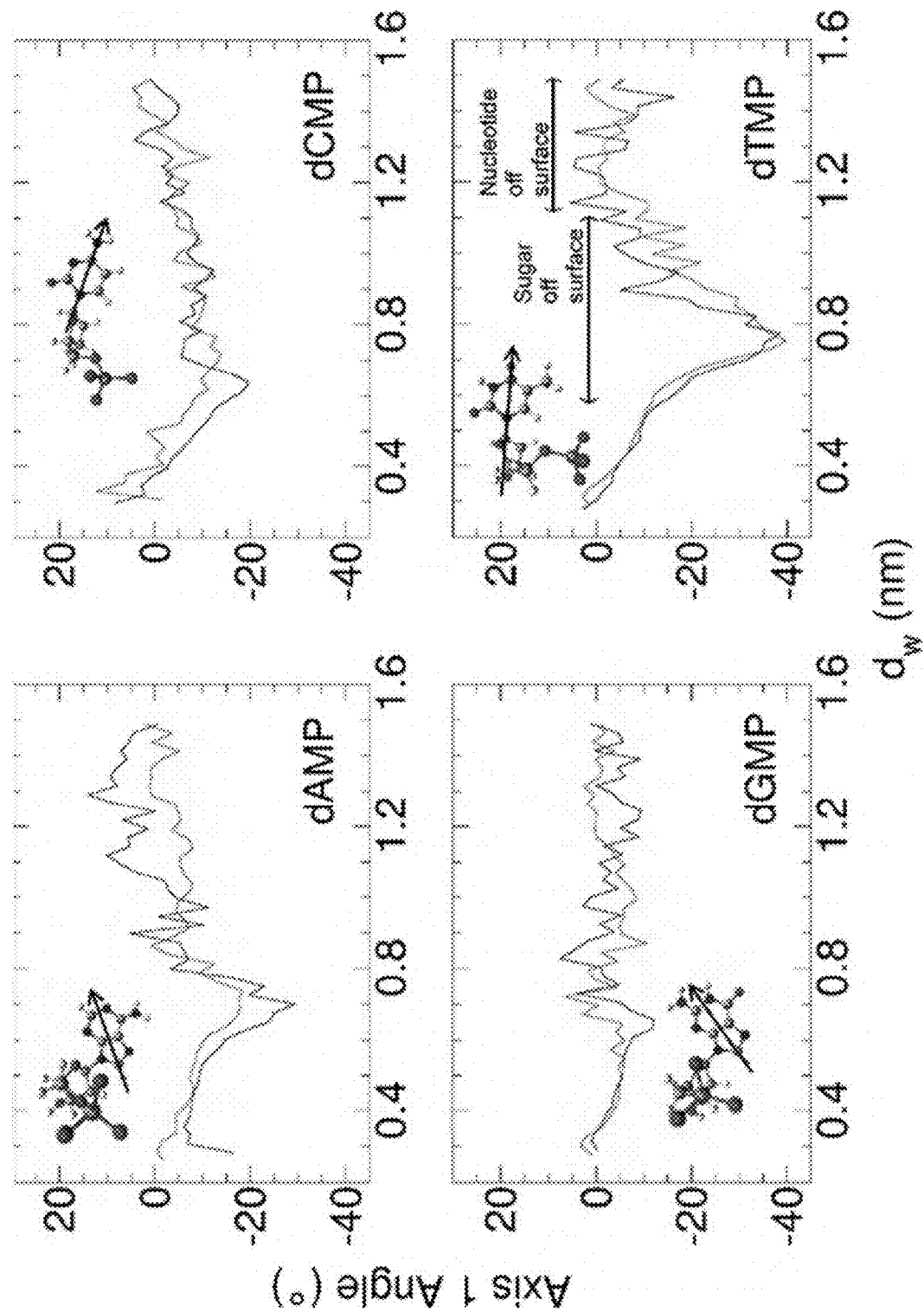
FIG. 38 shows the angle of Axis 1 with the surface plane as a function of $d_w$ for adsorption in the equilibrium case (gray) and non-equilibrium case (black). The arrows on the structures indicate the direction the axis points. Negative is pointing away from the center plane of the slit ($d_w$=1.5 nm).

The global minima and the small barriers in the PMF curves are related to the adsorption and desorption mechanism. Because the planar rings of the dNMPs tend to adsorb to the walls, the angles between two axes defined in the plane of the nucleobases and the wall surface planes are useful for looking at the adsorption/desorption mechanism. The average angles of an axis pointing from or near the atom in the nucleobase where the sugar attaches to the other end of the nucleobase (Axis 1) with the nearest wall surface plane as a function of $d_w$, are shown in FIG. 38 for adsorption and FIG. 39 for desorption in both the equilibrium and non-equilibrium cases. The average angles of an axis orthogonal to Axis 1 and in the plane of the nucleobase (Axis 2) with the nearest wall surface as a function of $d_w$, are shown in FIG. 41 for adsorption and FIG. 42 for desorption in both the equilibrium and non-equilibrium cases. The axes are shown in FIG. 33 (axis 1) and FIG. 40 (Axis 2) as well as on the plot insets. For the purpose of calculating the average angles, the periods for adsorption were from halfway between the previous desorption time and a given adsorption time to halfway between that adsorption time and the next desorption time. A similar approach was used to determine desorption periods. Table 7 shows the average Axis 1 and Axis 2 angles calculated while the dNMPs were adsorbed, regardless of whether this was during an adsorption or desorption period.

TABLE 7

Average Axis 1 and Axis 2 angles with the wall surface while the dNMP's are adsorbed for the equilibrium and non-equilibrium cases. The uncertainties are two times the standard deviation of the mean and calculated as described above.

| Nucleotide | Equilibrium | | Non-equilibrium | |
|---|---|---|---|---|
| | Axis 1 | Axis 2 | Axis 1 | Axis 2 |
| dAMP | −8.60 ± 1.15 | −0.63 ± 1.66 | −9.00 ± 1.10 | −0.67 ± 0.83 |
| dCMP | −7.86 ± 1.33 | −0.81 ± 1.29 | −6.16 ± 3.25 | −2.72 ± 3.04 |
| dGMP | −4.63 ± 0.58 | 0.82 ± 0.82 | −4.37 ± 2.09 | 0.72 ± 0.70 |
| dTMP | −8.84 ± 0.93 | −3.18 ± 0.89 | −8.91 ± 0.66 | −2.99 ± 0.66 |

Figure 39:
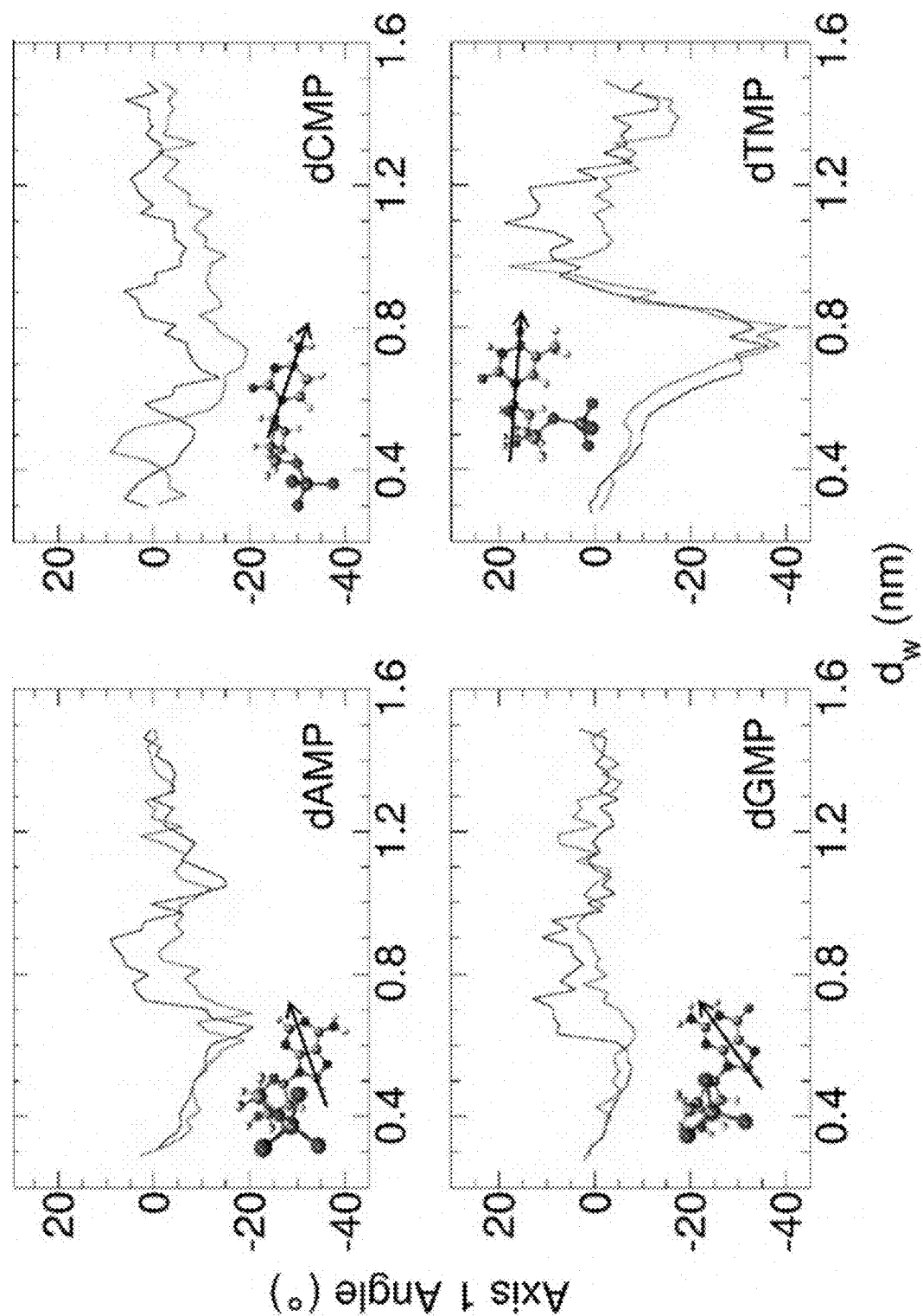
FIG. 39 shows the angle of Axis 1 with the surface plane as a function of $d_w$, for desorption in the equilibrium case (gray) and non-equilibrium case (black). The arrows on the structures indicate the direction the axis points. Negative is pointing away from the center plane of the slit ($d_w$=1.5 nm).
Figures 40A, 40B, 40C, 40D:
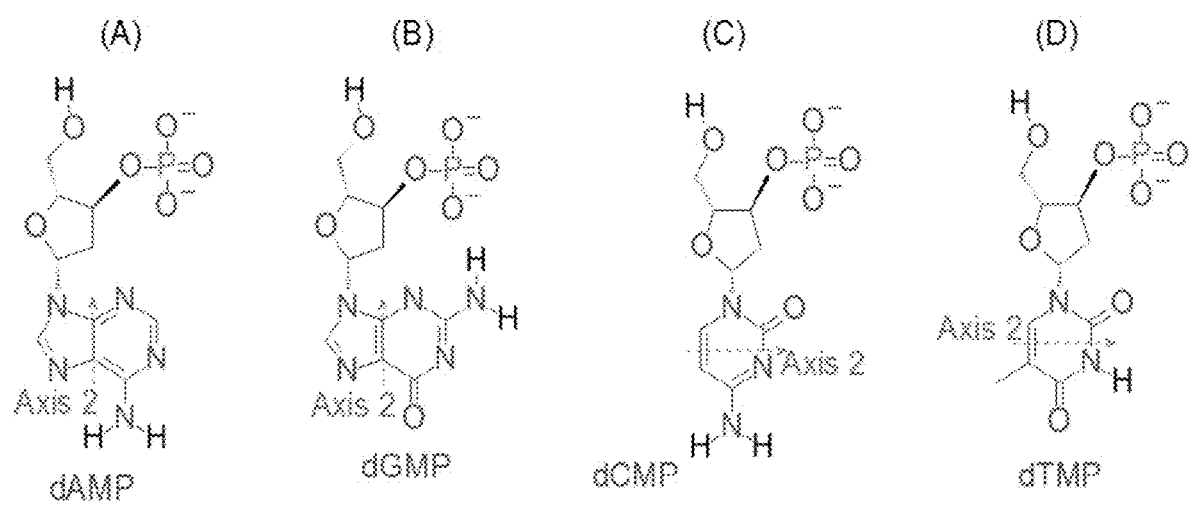
FIGS. 40A-40D depict the definitions of Axis 2, which lies in the plane of the nucleobases.

The curves in FIG. 38 and FIG. 39 show that the ends of the nucleobases attached to the sugar adsorb last and desorb first. This is because the sugar and phosphate groups are more hydrophilic than the nucleobases, which more favorably interact with the hydrophobic slit walls. The magnitudes of the global minima in the Axis 1 angles follow the same trend as the hydrophobicities of the nucleobases (G<C<A<T) (Shih et al., "Hydrophobicities of the Nucleic Acid Bases: Distribution Coefficients from Water to Cyclohexane," *J. Mol. Biol.* 280:421-430 (1998) and Munoz-Muriedas et al., "A Hydrophobic Similarity Analysis of Solvation Effects on Nucleic Acid Bases," *J. Mol. Model.* 13:357-365 (2007), which are hereby incorporated by reference in their entirety). For the nucleobases that are closer in hydrophobicity to the sugar, the minimum in the Axis 1 angle is not as severe. The minima in the PMF curves, around $d_w$=0.475 nm, occurred when the sugar end of the nucleobase was slightly farther from the surface than the other end, but was still adsorbed. Detachment of the sugar end from the surface increases the free energy. The barriers in the PMF curves at $d_w=d^M$ (see Table 6) are associated with adsorption and desorption of the end of the nucleobase opposite the sugar end, which is the last part of the dNMP to leave the surface.

The adsorption and desorption curves for a given dNMP shown in FIG. 38 and FIG. 39 for Axis 1 are not identical. For dAMP, dCMP, and dGMP, the magnitudes of the global minima in the Axis 1 angles were larger for desorption than for adsorption. For dTMP, the magnitude of the global minimum in the Axis 1 angles was smaller for desorption than adsorption, and there was a significant maximum in the desorption curve. The larger magnitudes of the minima for dTMP were due to the hydrophobic methyl group sticking to the surface.

The adsorption and desorption curves for a given nucleotide shown in FIG. 41 and FIG. 42 for Axis 2 are not easily distinguishable from each other because the change in the angles is comparable to the noise. When the nucleotides are near the wall during adsorption, the side of the dNMP that is most hydrophobic is generally closer to the wall; dTMP is an exception. The non-planar methyl group causes the side of the nucleotide it is on to be farther from the wall even though the methyl group is hydrophobic. The orientation of Axis 2 near the wall is not as strong during desorption. Given the level of noise, there are no significant minima or maxima in the Axis 2 angle for dAMP, dCMP, or dGMP. For dTMP, the hydrophobic methyl-surface interaction causes a significant maximum in the Axis 2 angle during adsorption and desorption. The dTMP maximum angle for desorption is smaller than for adsorption in the equilibrium case. For the desorption of dTMP, there is also a minimum in the Axis 2 angle following the maximum.

The angles of the axis 1 with the wall surface usually have the same qualitative and often quantitatively very similar behavior in the non-equilibrium case compared to the equilibrium case. The exception in the qualitative behavior is that during desorption for the pyrimidine bases (dAMP and dGMP) there is a maximum in the non-equilibrium case, but not in the equilibrium case. A quantitative exception is that the maximum for the Axis 2 angle during desorption of dTMP is smaller in the equilibrium case.

Example 3—Role of dNMP Interaction with Channel Walls on Various Equilibrium and Flow Characteristics Table 8 shows various quantities calculated from the simulations. These show, among others, that: i) For each of the four dNMPs the fraction of time adsorbed for the non-equilibrium case is nearly the same as in the equilibrium case. This is an indication that the adsorption/desorption behavior of the dNMPs is not significantly altered by the relatively high flow velocities used in these simulations. The flow velocities used are still small compared to the largest instantaneous thermal velocities of the molecules, which are on the order of hundreds of meters per second. ii) The times-of-flight of dCMP and dTMP are well separated even over only 50 nm travel distance, meaning that an uncharged, hydrophobic surface, such as that used in these simulations, is sufficient to distinguish these two dNMPs. This can be attributed to differences in hydrophobicity of the nucleobases: G<C<A<T (Shih et al., "Hydrophobicities of the Nucleic Acid Bases: Distribution Coefficients from Water to Cyclohexane," *J. Mol. Biol.* 280:421-430 (1998) and Munoz-Muriedas et al., "A Hydrophobic Similarity Analysis of Solvation Effects on Nucleic Acid Bases," *J. Mol. Model.* 13:357-365 (2007), which are hereby incorporated by reference in their entirety). Thymine has a hydrophobic methyl group, whereas cytosine has a hydrophilic amine group. iii) The increasing hydrophobicity trend matched the increasing time-of-flight trend except that the order of dGMP and dCMP was reversed. This was due to dNMP-wall interactions; the magnitude of the dGMP-wall energy ($V_{nuc-wall}$) while adsorbed was larger than the dCMP-wall energy while adsorbed. Because there are no strong specific interactions between different groups on the nucleobases and the wall surface and because the nucleobases sit nearly flat on the surface, $V_{nuc-wall}$ follows the same trend as the solvent accessible surface area of the nucleobases ($A_{base}$). Because guanine has a larger area than cytosine, dGMP has a larger area in contact with the wall than dCMP and a larger $V_{nuc-wall}$. iv) dAMP had twice as many adsorption events as did dGMP, but it was adsorbed for only a slightly smaller fraction of time and had a time-of-flight that was longer than that of dGMP. This resulted from the fact that dGMP spent longer stretches of time on or off the wall before desorbing or adsorbing again and that dGMP had a slightly larger wall sliding velocity. Comparing the data shown in Table 8 with the data shown in Table 6 shows that the free energies calculated from equilibrium simulations show the expected trend, more negative minimum or average adsorption free energy gives a longer time-of-flight. The free energies for dGMP and dAMP are an exception to this.

TABLE 8

Quantities calculated from the flow simulations, except for the last three rows. The area of the bases is from a single configuration, and the last two rows are from equilibrium simulations. Uncertainties in parentheses are two times the standard deviation of the mean and their calculation is described above.

| dNMP | dCMP | dGMP | dAMP | dTMP |
|---|---|---|---|---|
| $N_{sim}$[1] | 3 | 4 | 4 | 4 |
| $T_{sim}$ (ns)[2] | 155.9 | 252.9 | 213.1 | 305.2 |
| D (nm)[3] | 50.0 | 48.0 | 32.0 | 32.0 |
| $n_{ads}$[4] | 0.21(0.06) | 0.08(0.03) | 0.18(0.03) | 0.09(0.06) |
| $f_{ads, neq}$[5] | 0.38(0.15) | 0.68(0.23) | 0.63(0.10) | 0.93(0.03) |
| $t_{flight}$ (ns)[6] | 52(7) | 66(22) | 77(19) | 121(30) |
| $v_{all}$ (m/s)[7] | 0.99(0.23) | 0.80(0.17) | 0.63(0.18) | 0.41(0.13) |
| $v_{slide}$ (m/s)[8] | 0.68(0.61) | 0.42(0.24) | 0.33(0.28) | 0.38(0.14) |
| $V_{nuc-wall}$/(kT)[9] | −10.9(0.4) | −14.5(0.3) | −13.2(0.3) | −12.4(0.2) |
| $A_{base}$ (nm²)[10] | 2.4270 | 2.7963 | 2.6446 | 2.6197 |
| $f_{ads, eq}$[11] | 0.38(0.09) | 0.68(0.14) | 0.60(0.05) | 0.90(0.09) |

[1]Number of wall configurations (simulations)
[2]Total simulation time for all configurations
[3]Distance traveled in the flow direction for each configuration
[4]Number of adsorption events per nm travelled
[5]Fraction of time adsorbed, non-equilibrium
[6]Time-of-flight over 50 nm distance
[7]Average velocity in the flow direction
[8]Average velocity in the flow direction while adsorbed
[9]dNMP-wall potential energy while adsorbed
[10]Solvent accessible surface area of the nucleobases
[11]Fraction of time adsorbed, equilibrium

Example 4—Required Channel Length for Separation of dNMPs Based on the Nonequilibrium MD Simulations The required channel length to achieve reliable separation of the times of flight of the dNMPs was calculated from the distributions of the times of flight ($DTOF_{0.5}$) of the dNMPs over 0.5 nm segments sampled from the total length of the corresponding MD trajectories. The total lengths of these trajectories are 128 nm for dTMP and dAMP, 150 nm for dCMP, and 192 nm for dGMP (see Table 8, rows 1 and 3). The choice of 0.5 nm is arbitrary, and using any other length between 0.5 and 50.0 nm gives approximately the same result.

Using the $DTOF_{0.5}$ and employing the classical central limit theorem (Wasserman L. W., ALL OF STATISTICS: A CONCISE COURSE IN STATISTICAL INFERENCE (2004), which is hereby incorporated by reference in its entirety) one can calculate for each dNMP the distribution of the time of flight ($DTOF_{0.5N}$) over the larger distance, d=0.5N nm, where N is a positive integer number. For each dNMP using the $DTOF_{0.5}$ one can construct the corresponding $DTOF_{0.5N}$ as a function describing the distribution of the random variables $T_N=t_1+t_2+ \ldots +t_N$, where $\{t_1, t_2, \ldots, t_N\}$ is a set of independent time-of-flight values $t_i (i=1, N)$, randomly drawn from $DTOF_{0.5}$. Each new random variable, $T_N$, represents a dNMP time of flight over d=0.5N nm. According to the central limit theorem, if μ and $\sigma^2$ are the mean and the variance, respectively, characterizing the $DTOF_{0.5}$, which needs not necessarily be a normal or even symmetric distribution, in the limit of large values of N the $DTOF_{0.5N}$ will approximate the normal distribution and will be characterized by the mean value Nμ and by the variance $N\sigma^2$ (or standard deviation equal to $(N)^{1/2}\sigma$). As the number of segments N is increased the width of the $DTOF_{0.5N}$ increases only as the square root of N compared to the mean value which increases linearly with N. Therefore, the increase of N, which in this case translates in the increase of the distance of flight, leads to better separation of the $DTOF_{0.5N}$. Obviously, when estimating the required minimum channel length $d_{min}$=0.5N nm for separation one needs to define the acceptable level of distributions overlap. In our approach $d_{min}$=0.5N nm was estimated as the distance traveled by the dNMPs when N was such that less than 0.27% of any one of the distributions of the mean overlapped with one of the other distributions of the mean. This percentage corresponds to 3 standard deviations from the mean for a normal distribution. The misidentification rate for C and T would be 0.27%, and the rate for A and G would be 0.46%. The details on the calculation of N and the required length are described supra.

Table 9 shows the values of distances required to separate times of flight for each of the six different dNMP pairs. The length required to fully distinguish all of the dNMPs is the distance required to separate the times of flight of dAMP and dGMP, 5.9 μm. Although approximate, and for the conditions of the simulation which would be difficult to replicate in a real system, this number may be used as the basis for comparison of different surfaces.

TABLE 9

Distances (μm) required to separate the times of flight of dNMP pairs.

| | dCMP | dGMP | dAMP | dTMP |
|---|---|---|---|---|
| dCMP | ∞ | 1.31 | 0.43 | 0.06 |
| dGMP | 1.31 | ∞ | 5.94 | 0.24 |
| dAMP | 0.43 | 5.94 | ∞ | 0.56 |
| dTMP | 0.06 | 0.24 | 0.56 | ∞ |

Figure 43:
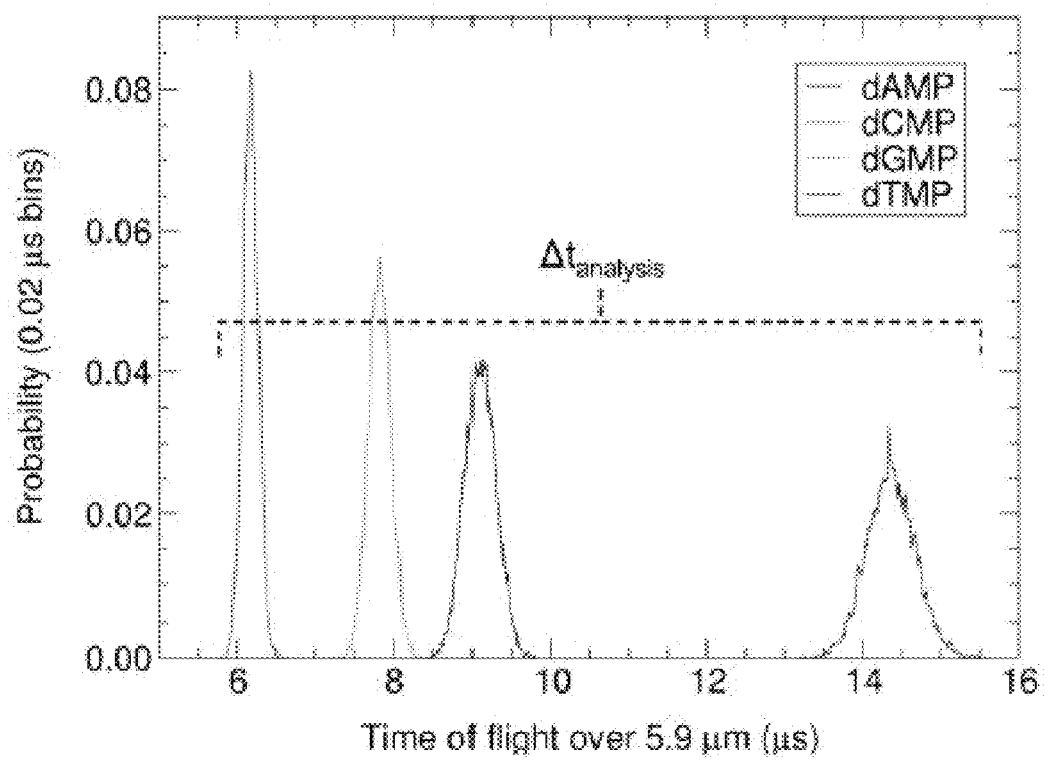
FIG. 43 is a graph showing flight time distributions over 5.9 m. A total of 10,000 times-of-flight were used for each dNMP with each data point generated by summing up the times-of-flight of $N_{dAMP,dGMP}$11 887 random samples from the flight time distributions over 0.5 nm. The minimum analysis time per dNMP ($\Delta t_{analysis}$) is about 10 s.

FIG. 43 shows the time-of-flight distribution over 5.9 m with each time of flight generated by summing up N=$N_{dAMP}$, $d_{GMP}$ samples from the 0.5 nm time-of-flight distributions. At this distance the distributions for dAMP and dGMP are just barely separated. The width of the whole set of distributions is the minimum analysis time per dNMP ($\Delta t_{analysis}$), since the time between dNMPs entering the channel must be at least this long in order to prevent misordering.

Example 5—Estimate for Realistic Flow Rates

Although the dNMPs can be separated over a short distance on the order of micrometers with the minimum analysis time per dNMP on the order of 10 µs in the MD simulation, realistic flow rates will be 2-3 orders of magnitude smaller. Under those conditions, there will be significantly more broadening of the time-of-flight distributions due to diffusion. In this subsection, the effect of diffusion on the required channel length and the minimum analysis time per dNMP are estimated. Perhaps the best way of estimating the effect of realistic flow rates, short of doing extremely expensive MD simulations at low flow rates, would be to use the strategy introduced by Carr et al., which would involve calculating potentials of mean force (PMF) between the dNMPs and the walls in all three Cartesian dimensions and then using the resulting forces as a function of position in Brownian dynamics (BD) simulations (Carr et al., *Lab Chip* 11: 3766-3773 (2011), which is hereby incorporated by reference in its entirety). Although the forces derived from an equilibrium PMF calculation are not strictly correct under nonequilibrium conditions, Carr et al. showed that there was good agreement between BD simulations and MD simulations with pressure-driven flow (Carr et al., *Lab Chip* 11: 3766-3773 (2011), which is hereby incorporated by reference in its entirety). The advantage of this 3D PMF+BD strategy would be that, although the PMF calculation would be expensive, the BD simulations would involve only a single dNMP which would allow for much larger time scales and channel widths compared to MD simulations.

Using some assumptions about the diffusivities and velocity profiles of the dNMPs and the probability of observing the dNMPs as a function of distance from the walls which is related to the PMFs by eq 1, order of magnitude channel lengths and analysis times per dNMP can be obtained without having to calculate a 3D PMF. The following assumptions were used:
(1) The diffusivities of all of the dNMPs at any distance from the walls are the same and equal to the diffusivity of cyclic AMP which is $4.44 \times 10^{-6}$ cm$^2$/s (Dworkin et al., *J. Biol. Chem.* 252:864-865 (1977), which is hereby incorporated by reference in its entirety).
(2) The velocity profile of the dNMPs is parabolic with a maximum velocity ($v_{max}$) of 0.048 cm/s, which is about the speed that the dNMPs would travel by electrophoresis in bulk aqueous solution under an electric field of 1000 V/cm, and a velocity of zero for values of $d_w$ less than or equal to the average dNMP position while adsorbed. Assuming zero sliding velocity is probably not correct, but at lower velocities and with rougher walls the ratio of sliding velocity to average velocity will be much lower than in the MD simulations. Assuming a different shape of the velocity profile would alter the average velocities somewhat, but not change the order of magnitude of the estimates.
(3) The average velocity in the flow direction (x) is $$\bar{v}_x = \int_0^{d_w^{CL}} PD(d_w)v_x(d_w)d(d_w) \approx \sum_i PD_i v_{x,i}(\Delta d_w)_i = \sum_i Pr_i v_{x,i} \quad (3)$$

This is similar to eq 2 and uses the same symbols except for $v_{x,i}$, which is the velocity in the flow direction in bin i, and $d_w^{CL}$, which is the distance from the walls at the center line of the slit. The use of eq 3 assumes that the probabilities are the same in the flow situation as in the equilibrium simulation. Given that even in the nonequilibrium MD simulations at very high velocity the fractions of time adsorbed were similar, this is a valid assumption.
(4) For a given channel length L, average velocity $\bar{v}_x$, and diffusivity D, the time-of-flight probability density distribution is $$\rho(t) = \frac{1}{\sqrt{4\pi Dt}} \exp\left[\frac{-(L - \bar{v}_x t)^2}{4Dt}\right] \quad (4)$$

which is just the distribution for one-dimensional diffusion with a time-dependent average position of $\bar{v}_x t$.
(5) The allowed overlap of distributions was the same as used in the analysis of the MD simulations.

Figure 44:
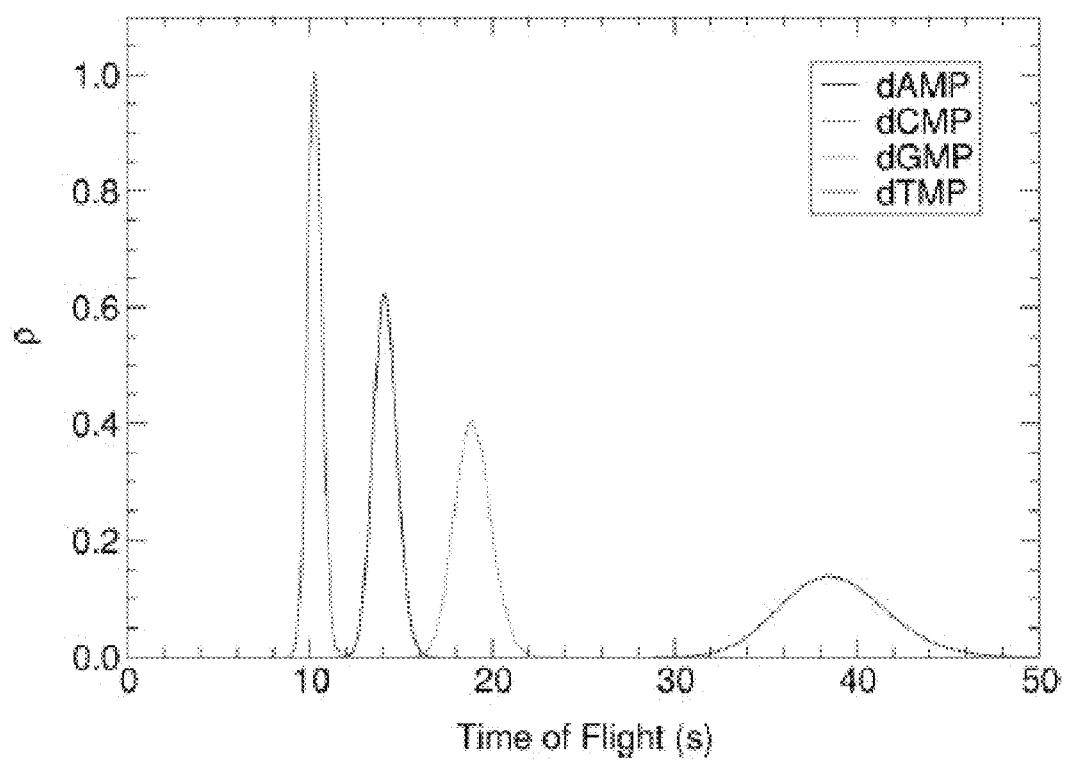
FIG. 44 is a graph showing the estimated time-of-flight distributions for a center line velocity ($v_{max}$) of 0.048 cm/s and a channel length of 2.47 mm.

With these assumptions in place, the goal was to find the minimum L that did not violate the desired overlap of distributions and the corresponding $\Delta t_{analysis}$. The values of L and $\Delta t_{analysis}$ determined for $v_{max}$=0.048 cm/s were estimated to be about 2.5 mm and 39 s, respectively. FIG. 44 shows the time-of-flight distributions over the 2.5 mm distance. Although channels with sub-20 nm dimensions of up to 1 cm long have been fabricated (Liang et al., *Nano Lett.* 7: 3774-3780 (2007), which is hereby incorporate by reference in its entirety), the time to analyze each dNMP is too long considering that millions or billions of dNMPs (the human genome has about 3 billion base pairs) might need to be sequenced. Sequencing the human genome in a day at that rate would require about 1.4 million channels in parallel, not including any redundancy. Fortunately, while L is only inversely proportional to the velocity, $\Delta t_{analysis}$ is inversely proportional to the velocity squared. If the velocity was increased by a factor of 10, the required length would be 250 m and $\Delta t_{analysis}$ would be 390 ms.

For a given $v_{max}$, there is a minimum possible $\Delta t_{analysis}$ which can be estimated. In addition to assumptions 1,4, and 5 above, one of the dNMP types is assumed to have $\bar{v}_{x,1}=v_{max}$; it is assumed to not be affected by the walls. A second dNMP type is assumed to have $\bar{v}_{x,2}=\bar{v}_{x,2}-\Delta v_x$, and the third and fourth types to have even smaller velocities ($\bar{v}_{x,4}<\bar{v}_{x,3}<\bar{v}_{x,2}$) such that all of the distributions are crowded against each other as far as possible given assumption 5 above. By varying $\Delta v_x$, a minimum for $\Delta t_{analysis}$ can be found. For $v_{max}$=0.048 cm/s, the minimum $\Delta t_{analysis}$ is about 5.0 s and L is about 1.29 mm. For $v_{max}$=0.48 cm/s, the minimum $\Delta t_{analysis}$ is about 50 ms and L is about 129 m.

Discussion of Examples 1-5

The four deoxydNMP 5'-monophoshates commonly found in DNA were simulated in aqueous solution in 3 nm wide nanoslits composed of disordered Lennard-Jones carbon atoms in order to compare their times of flight and dynamics. The solution was driven by body forces, which are known to induce flow that is similar to that induced by pressure difference or capillary forces. For comparison, and to calculate the free energy for adsorbing the dNMPs onto the slit walls, a case with no external forces was also considered. The dNMPs adsorb and desorb within nanoseconds even with no flow. The flow did not have a large effect on the adsorption and desorption behavior of the dNMPs, and the fractions of time that the dNMPs were adsorbed were nearly the same in equilibrium and nonequilibrium simulations. The times of flight of the most hydrophobic dNMP (dTMP) and one of the most hydrophilic dNMP (dCMP) were easily separated using hydrophobic carbon slit walls, indicating that modifying the wettability properties of the wall material may be a promising way to achieve high reliability in discriminating between dNMPs on the basis of their flight times through nanochannels, although interactions of specific chemical groups in dAMP and dGMP with groups on the wall surface will also be important for their separation since their times of flight were nearly the same. Important questions regarding dAMP and dGMP are whether their qualitatively different behavior during desorption under flow conditions compared to equilibrium conditions plays a role in the ability to separate their times of flight and whether this behavior persists at the much lower velocities that would be used in a real device. Analysis of the effect of diffusion at realistic flow rates indicates that the dNMP velocity should be relatively high in order to get a reasonable minimum analysis time per dNMP.

Example 6—Solid Phase Immobilization of i-Exonuclease (λ-Exo)

λExonuclease (λ-Exo) was immobilized on a thermoplastic (PMMA) solid phase surface. λExo was provided with a 10× reaction buffer (670 mM glycine-KOH, pH 9.4, 25 mM $MgCl_2$, 0.1% (v/v) Triton X-100) (Fermentas Life Sciences, Glen Burnie, Md.). No purification steps were performed prior to use.

Figure 45:
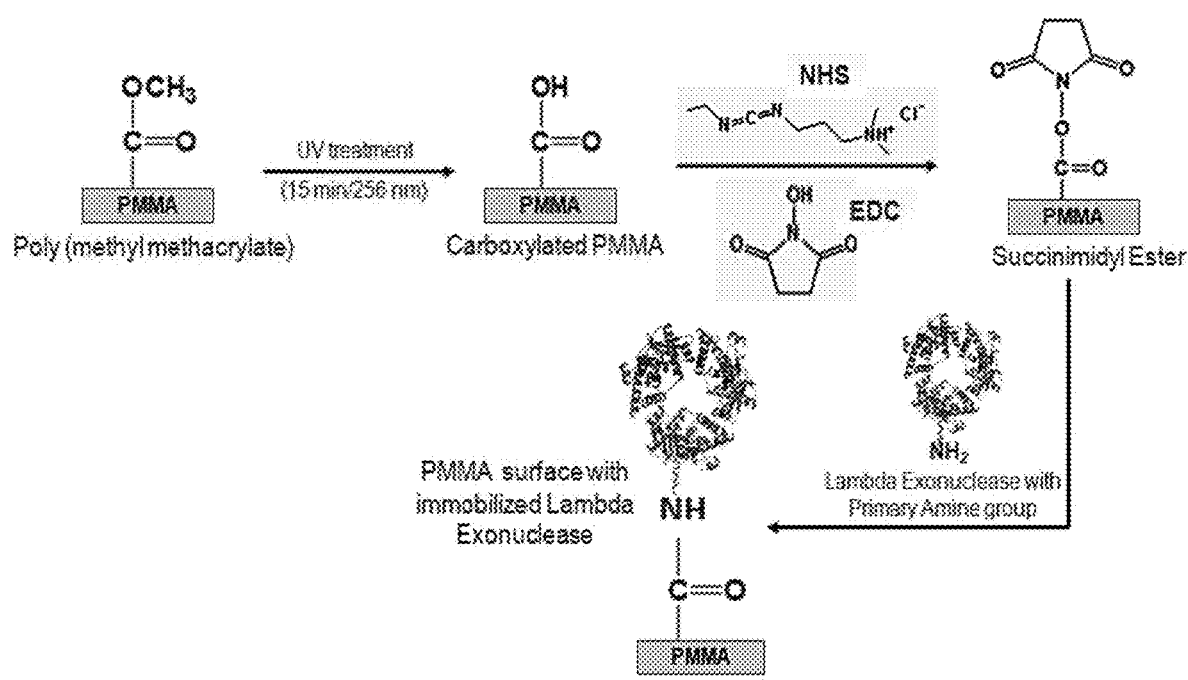
FIG. 45 is a schematic showing the process of immobilizing λ-Exonuclease (λ-Exo) to a poly(methylmethacrylate) (PMMA) surface.

Following thermal fusion bonding of the PMMA cover plate to the PMMA substrate to which the λExo is immobilized (Henry et al., "Surface Modification of Plastics Used in the Fabrication of Microanalytical Devices," *Analytical Chemistry* 72: 5331-5337 (2000); McCarley et al., "Resist-Free Patterning of Surface Architectures in Polymer-Based Microanalytical Devices," *J. Am. Chem. Soc.* 127: 842-843 (2005), which are hereby incorporated by reference in their entirety), succinimidyl ester intermediates were formed to facilitate enzyme attachment. This was carried out by filling the solid-phase reactor with a solution containing 200 mM 3-(3-dimethylaminopropyl) carbodiimide (EDC), and 50 mM N-hydroxysuccinimide (NHS) in 0.1 M 2-(4-morpholino)-ethane sulfonic acid at pH 5.1 (MES, Fisher Biotech, Fair Lawn, N.J.) for 15 min at room temperature. The EDC/NHS reagents were then hydrodynamically displaced with a solution consisting of 0.03 μg/4 μL λExo enzyme. The reaction was allowed to proceed overnight at 4° C. The enzyme-functionalized device was rinsed with 1×λExo reaction buffer to remove all unbound reagents from the PMMA surface. FIG. 45 is a schematic summarizing the process of λExo immobilization.

Characterization of the surface-immobilized λ-Exo was performed using an Asylum Research MFP3D Atomic Force Microscopy (AFM) at a 1.00 Hz scanning rate in AC (tapping) mode. The samples used for AFM consisted of PMMA sheets containing the immobilized λ-Exo enzyme. The PMMA sheets were cut into 1.7 cm×1.7 cm squares and were 3 mm in thickness. Following cutting, the substrates were cleaned, dried, and UV activated as previously described. The sheets were subjected to EDC/NHS coupling with enzyme addition completed as described above. Samples were rinsed with reaction buffer, dd$H_2O$, and gently dried with compressed air prior to AFM analysis.

Figure 46A:
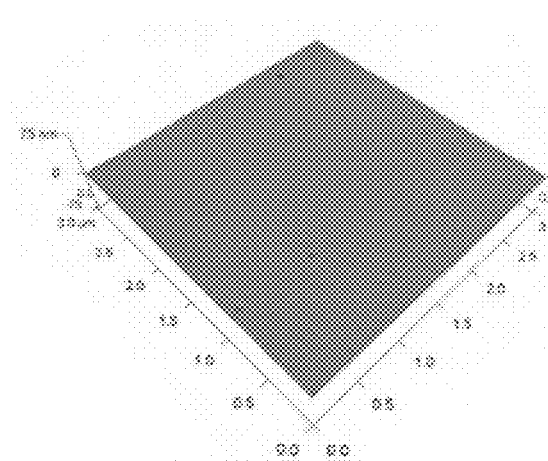
FIGS. 46A-46C demonstrate λ-Exo immobilization on PMMA surface.
Figure 46B:
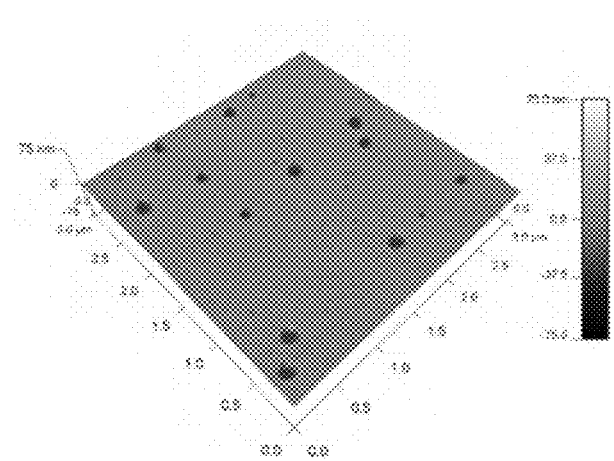
Figure 46C:
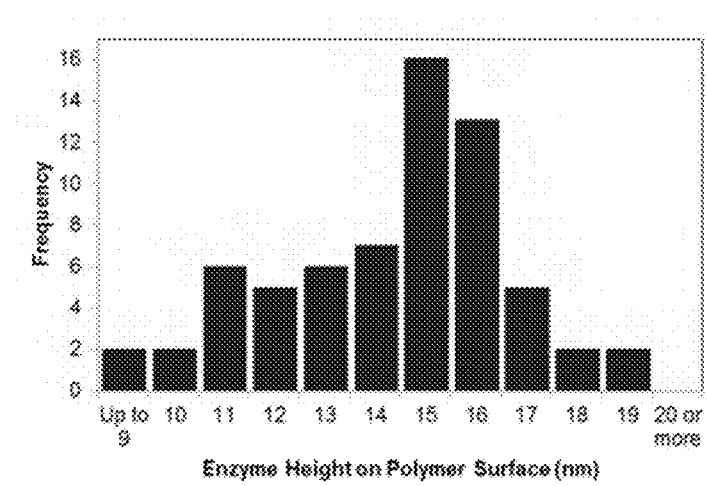

Immobilization of λ-Exo to PMMA was performed via EDC/NHS mediated conjugation of amine groups on the protein exterior to carboxylic acid groups generated on the substrate surface. Successful attachment of λ-Exo onto PMMA was confirmed by AFM analysis. To determine any enzyme non-specific adsorption, the PMMA substrate was activated with UV light and, in the absence of EDC/NHS coupling reagents, was incubated with the λExo enzyme solution overnight at 4° C. FIG. 46A is an AFM scan of the PMMA/λ-Exo reaction performed in the absence of the EDC/NHS coupling reagents. This scan shows no evidence of surface textures consistent with the size and shape of the λExo enzyme, confirming that physisorption of the enzyme onto the polymer surface did not occur under these current conditions. FIG. 46B is an AFM image of the PMMA/λ-Exo reaction performed in the presence of the EDC/NHS coupling reagents. As compared to the scan of FIG. 46A, the scan of FIG. 46B shows surface features consistent with the size of λExo. Substrates containing covalently attached protein had an average RMS roughness of 1.58±0.18 nm as compared to 0.34±0.01 nm for substrates where enzyme with no EDC/NHS coupling agents were present. Therefore, covalent attachment of enzyme to the PMMA surface was observed only in the presence of EDC/NHS coupling, and physisorption did not occur. From multiple scans conducted over a 15 μm area across various regions (n=6) of the substrate, AFM height profiles of the surface features suggested that the average height of these features was 15 nm, which corresponds to the reported λExo outer diameter (~150 Å) based on x-ray crystallographic data. FIG. 46C is histogram of feature heights created to determine the size distribution of these features. From this data, 71% of the features detected fell within a height range of 14.3±2.3 nm. The height variations could be due to the non-contact mode of imaging used to reduce sample disruption or displacement during analysis. This data indicates that the majority of the features are consistent with single-point attachment of the λ-Exo to the activated surface. Therefore, the majority of the immobilized enzymes are oriented with their access pore for inclusion of dsDNA near normal to the substrate surface. The absence of a double-distribution of feature heights in the histogram indicates that the enzyme under the UV dose and enzyme concentration used for the immobilization reaction did not lead to surface cross-linking in which the enzyme and its access pore would lie parallel to the surface making it inaccessible to dsDNA based on surface steric considerations. The AFM data from immobilization also confirms that conjugation of the complete homotrimer was achieved and no dissociation of the enzyme into its monomer units, as a result of the attachment process, was observed.

Example 7—Solid-Phase Digestion of hDNA Using λExonuclease

Duplex λ-DNA (48,502 bp) (New England Biolabs, Ipswich, Mass.), was incubated in the λExo-modified reactor for various reaction times, which were selected by hydrodynamically pumping the λ-DNA solution through the solid-phase reactor at the appropriate velocity to provide the desired residence time. Hydrodynamic pumping was controlled using a mechanical pump (PHD2000 syringe pump, Harvard Apparatus, Holliston, Mass.). Reactor assays were temperature controlled at 37° C. via a custom-built thermocouple heating stage. The effluent was collected at the device outlet for downstream analyses.

PicoGreen® (Life Technologies, Grand Island, N.Y.), a double-stranded DNA (dsDNA) intercalating dye, was used for determining the amount of dsDNA remaining following passage through the enzyme reactor. Picrogreen® shows high specificity for binding to dsDNA with a resultant fluorescence enhancement (approximate 1,000-fold increase in its fluorescence quantum efficiency when intercalated to dsDNA). Because the dye does not bind to single stranded DNA (ssDNA) or mononucleotides with an associated fluorescence increase, it is suitable for determining specifically the dsDNA content from a λ-Exo solid-phase reaction, which should consist of ssDNA, dsDNA, and mononucleotides. The dye was added post-digestion for quantification of intact dsDNA amount. Post-digestion addition was performed as opposed to pre-digestion because previous reports noted a decrease in enzymatic activity of λExo upon nuclear staining (Subramanian et al., "The enzyme bias of processivity in lambda exonuclease," *Nucleic Acids Research* 31: 1585-96 (2003), which is hereby incorporated by reference in its entirety). The dye-labeled samples were excited at 480 nm and fluorescence spectra were collected from 490 nm to 700 nm using a Fluorolog-3 spectrofluorometer (Horiba JobinYvon, Edison, N.J.) and DataMax Software 2.20.

Figure 47:
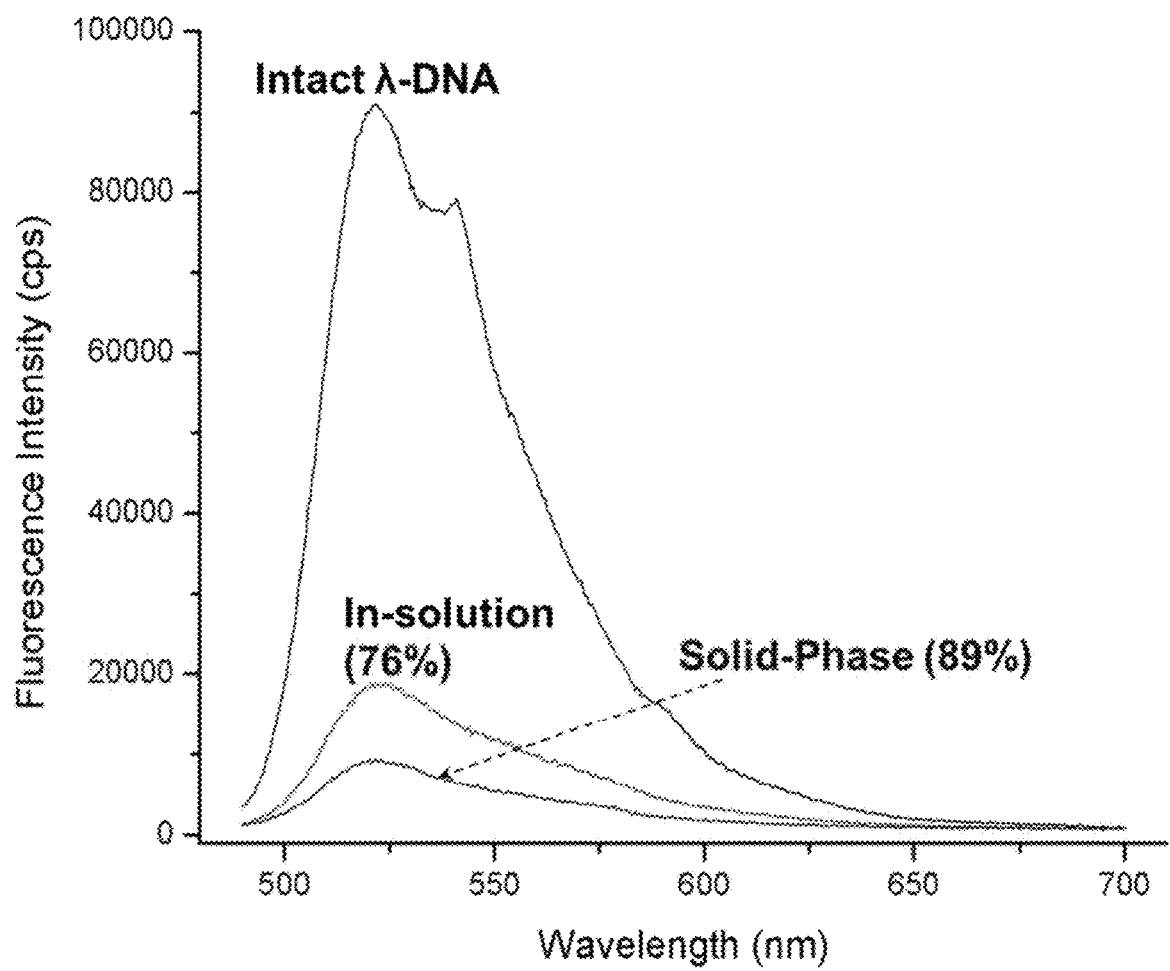
FIG. 47 shows the fluorescence spectra of λ-DNA following free solution λExo digestion and solid phase reactor λExo digestion. The fluorescence spectra of undigested λ-DNA is also shown as a control.

FIG. 47 shows fluorescence spectra of a free solution λExo digested λ-DNA and a solid-phase reactor λ-Exo digested λ-DNA (same effective reaction times). To determine the extent of DNA digestion in the reactor, Picogreen®, a nuclear staining dye was added to the reactor bed effluent or the free enzyme reaction solution, and fluorescence spectra was acquired indicating the amount of dsDNA remaining in solution. As shown in the graph of FIG. 47, the amount of fluorescence observed for the free solution digestion was considerably higher than that detected from the solid-phase reactor digestion, indicating that more dsDNA was present in the free solution digestion compared to the solid phase digestion.

Example 8—Real-Time Monitoring of Surface-Immobilized λExonuclease Digestion

To determine the digestion rate of the immobilized λ-Exo, real-time fluorescence monitoring was employed. The microscope utilized in these studies consisted of a Zeiss Aviovert 200M inverted microscope (75 W Xe lamp, Zeiss, Germany) that was equipped with a Zeiss 100×/1.3 NA oil-immersion microscope objective and an Andor iXon3 EMCCD camera. A custom mount was machined to hold the assembled PMMA devices onto the microscope stage during analysis. All images were collected and analyzed using MetaMorph Advanced 7.7.6.0 software (Molecular Devices LLC, Sunnyvale, Calif.) and ImageJ 1.46 (National Institutes of Health, Bethesda, Md.). λ-Exo 10× reaction buffer without co-factor (glycine-KOH in ultra-pure water at pH 9.4, 0.1% (v/v) Triton X-100) was prepared for use in these experiments to control initiation of enzyme digestion of dsDNA. Following attachment of λExo enzyme to PMMA, YOYO®-1 labeled λ-DNA in a 1:50 dye-to-base pair ratio was incubated in the reactor for ~3 hours to create an enzyme-DNA complex. Reaction buffer (1×) containing 25 mM $MgCl_2$ co-factor was introduced into the device and heated to 37° C. followed by imaging for real time monitoring of enzyme activity (see FIG. 48). To allow pumping of reagents and dsDNA through the reactor, a PHD2000 syringe pump (Harvard Apparatus, Holliston, Mass.) was used. The pump was connected to the reactor by sealing peak tubing to inlet/outlet reservoirs via epoxy with the inlet tube connected to a syringe using a leur-lock connector.

Figure 48:
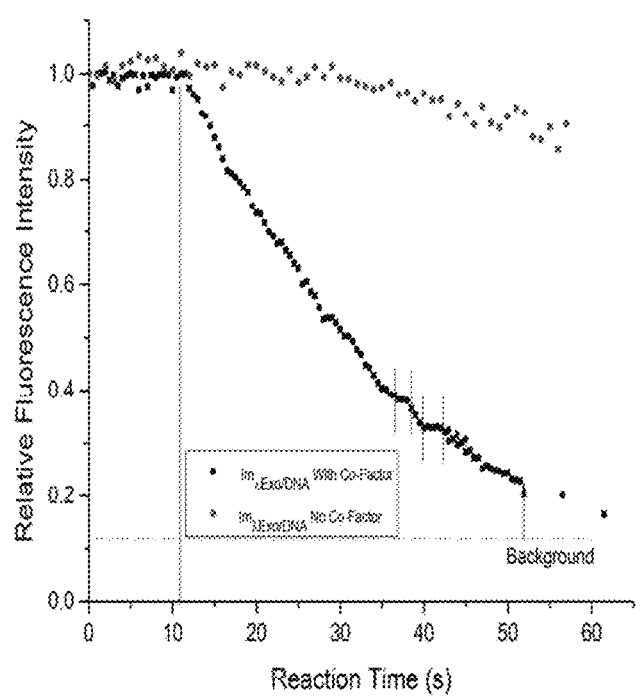
FIG. 48 is a graph showing real-time fluorescence monitoring of λ-Exo digestion activity. Fluorescently labeled λ-DNA was incubated with immobilized λExo in the presence (■) and absence (•) of $MgCl_2$ co-factor, and the decrease in relative fluorescence intensity, indicative of of λExo digestion activity, was monitored over the course of the reaction time.

The average digestion rate of the surface immobilized λ-Exo, determined based on the total number of base-pairs for 2λ-DNA (48,502 bp) and the total digestion time, was 1135±124 nucleotides/second (n=4). This digestion rate is in line with those previously reported (Matsuura et al., "Real Time Observation of a Single DNA Digestion by Lambda Exonuclease under a Fluorescence Microscope," *Nucleic Acids Research* 29: e79 (2001), which is hereby incorporated by reference in its entirety), but with increased digestion efficiencies (Ayub et al., "Nanopore Based Identification of Individual Mononucleotides for Direct RNA Sequencing," *Nano Letters* 13: 6144-6150 (2013); Matsuura et al., "Real Time Observation of a Single DNA Digestion by Lambda Exonuclease under a Fluorescence Microscope," *Nucleic Acids Research* 29: e79 (2001), which are hereby incorporated by reference in their entirety). This information suggests that the processive behavior of λ-Exo yields digestions >30,000 nucleotides, a value 10 fold higher than previous reports. To ascertain that the reduction in fluorescence intensity was a result of digestion and not photobleaching or photonicking, control experiments were performed by exposing a threaded λ-DNA molecule in the absence of the co-factor, to the excitation light for a duration longer than the total observed digestion times. Relatively constant fluorescence was observed throughout the time duration of a typical digestion experiment as depicted in FIG. 48 when the reaction was not fortified with the enzyme co-factor (i.e., enzyme activity is equal to 0.0).

Example 9—Microchip (PMMA) Capillary Electrophoresis of Mononucleotides

Capillary electrophoresis (CE) was performed using a Beckman Coulter CE instrument with UV detection at 254 nm. Bare fused silica capillaries from Molex Polymicro Technologies (Phoenix, Ariz.), possessing a 50 μm internal diameter, were used for the CE (total length=33 cm, 20 cm effective length). The CE columns were preconditioned with 0.1M NaOH for 30 min and rinsed by flushing with filtered 0.5×TBE buffer (45 mM Tris, 45 mM borate, 1 mM EDTA, pH 8.3, in ultrapure water—18 MΩ). Finally, the capillary surface was treated with a dynamic coating containing 2% (w/v) polyvinylpyrrolidone (PVP, Mr=40,000; Sigma Aldrich St. Louis, Mo.) in 0.5×TBE, pH 8.3 to suppress the electro-osmotic flow. The CE running buffer also contained a cationic surfactant, in this case cetyltrimethylammonium bromide (CTAB). Sample introduction was performed by electrokinetic injection at 10 kV for 180 s. The CE was performed on the native deoxynucleotide monophosphates (dNMPs, 4 including the methylated C) at a concentration of 1 μM.

Figure 49:
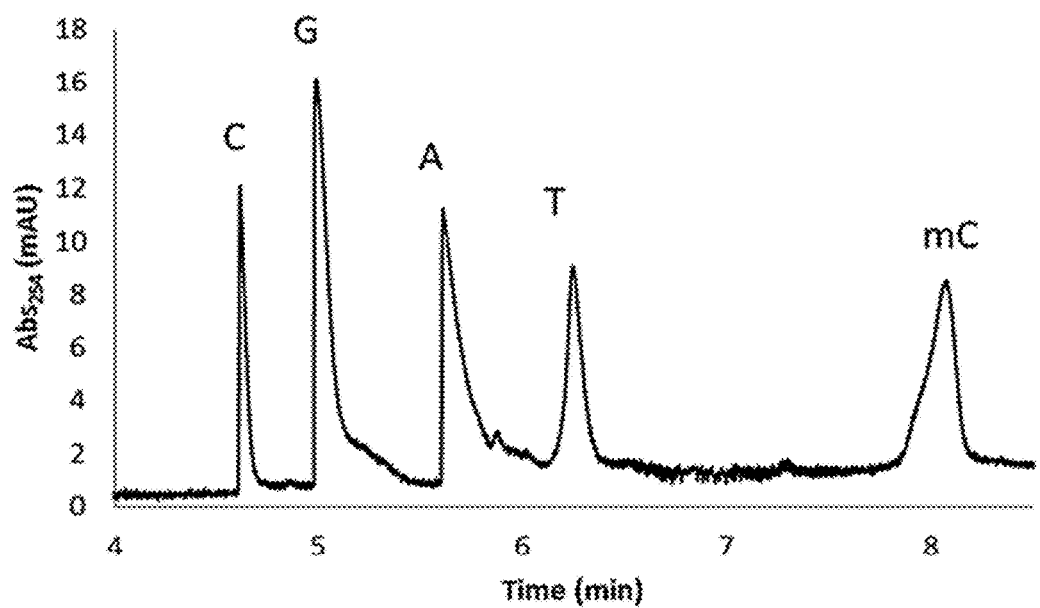
FIG. 49 is a graph showing the baseline resolution of native deoxynucleotide monophosphates (dNMPs) by capillary electrophoresis (CE).

Using the CE conditions described herein, a baseline resolution of native dNMPs was obtained as depicted in FIG. 49. However, this was accomplished using a column that was nearly 20 cm in length and required a development time of 8 min. For time-of-flight analyses, the separation time will be on the order of 1 ms and the column length will be about 50 μm. In spite of this shorter development time and column, the resolution will not be degraded because the resolution only depends on the peak width and differences in the electrophoretic mobility of the dNMPs. The electrophoretic mobilities are independent of electric field strength, column length, and CE development time.

Example 10—Effects of Surface Treatment on Thermoplastic Electro-Osmotic Flow in PMMA Nanochannels PMMA nanofluidic devices were fabricated using Nanoimprint Lithography (NIL). Briefly, the nanochannel-based fluidic device consisted of three major parts: (a) a microfluidic network, which included reservoirs and transport channels of 75 μm in width and 20 μm in depth; (b) a gradient interface at the inlet of the nanochannels, the funnel-like inlet consisting of 16 trapezoidal prisms with widths decreasing from 30 μm to 75 nm and a depth decreasing from 10 μm to 75 nm; and (c) an array of nanochannels that were 75 nm in width and 75 nm in depth.

The fabrication steps can be divided into four key steps: (1) forming the silicon master with recessed nanochannels and hierarchical microscale fluidic networks; (2) transferring the silicon master pattern into a UV-curable resin layer coated onto a cyloolefin copolymer (COC) substrate via UV-NIL to produce polymer stamps with protrusive structures; (3) nanoimprinting with the UV-resin stamp into PMMA substrates to generate the nanofluidic structure; and (4) bonding a PMMA cover slip to the substrate to form the fluidic system.

To build the silicon master, silicon wet etching and focused ion beam (FIB) milling were combined to build a hierarchical structure. Reservoirs and transport channels were defined by conventional photolithography and etched anisotropically with 30% KOH solution on the surface of silicon. Funnel inlet and nanochannel arrays were then milled step by step with FIB (FEI Quanta 3D FEG). Finally, a monolayer of 1H,1H,2H,2H-perfluorodecyltrichlorosilane was coated from the gas phase in a vacuum chamber.

A UV-curable polymeric blend containing 69 wt % tripropylene glycol diacrylate (TPGDA) as the base, 29 wt % trimethylolpropane triacrylate as crosslinking agent, and 2 wt % Irgacure 651 as photo-initiator, was selected as the material for the polymer stamp. The silicon mold was coated with the UV resin by dispensing with a pipette. Then, a COC substrate (COC-TOPAS 6017, TOPAS Advanced Polymers, Florence Ky.) was placed on the UV resin-coated stamp and was gently pressed in order to ensure complete filling of the resin into mold cavities. This was followed by an exposure of UV light for 20 sec for curing. The UV lamp used for curing had an intensity of 1.8 W/cm$^2$; the broadband wavelength with a cut-off angle of 400 nm and the maximum wavelength intensity at ~365 nm. After curing, the UV-curable resin was gently demolded from the silicon mold to get the negative copy on UV-curable resin.

The patterned UV-curable resin was then used as stamp to hot impress into a 3 mm-thick PMMA sheet (Lucite CP) with previous milled holes for reservoirs. The imprinting was carried out at 130° C. and 20 bar for 5 min by NIL (Obducat nanoimprint system), which applied pressure to the stamp and substrate using compressed air, ensuring pressure uniformity over the entire imprint area. The pressure was added after the 30 s preheating of both the stamp and substrate at the desired molding temperature, and was kept during the imprinting process until the system had been cooled to 70° C. After the stamp and substrate were cooled to room temperature, a PMMA copy could be easily demolded from the UV-resin stamp.

A 125 mm thick PMMA sheet (Goodfellow Corporation) was used as the cover slip. Both the patterned PMMA sheet and cover slip were treated by oxygen plasma under 15 W for 15 s to activate the surface. The thermal bonding was done immediately after plasma treatment. A pressure of 20 bar, temperature of 80° C. and time of 10 min was used to achieve a desirable bonding strength without affecting the structures on PMMA. The NIL machine was employed to give a homogeneous pressure during bonding process.

The electroosmotic flow (EOF) was measured using a discontinuous buffer system in which the anodic reservoir was filled with 2 μM KCl and the cathodic reservoir was filled with 1 μM KCl following filling of the nanochannel with the 1 μM KCl solution. During electrophoresis, in which an electric field of 200 V/cm was applied, the current was monitored continuously using an AxoPatch current amplifier. The EOF, unless otherwise stated, flowed toward the cathodic reservoir due to the negative charge on the channel walls. In the case of the amine-modified PMMA nanochannel wall, the EOF flowed in the direction of the anode.

Figures 50A, 50B:
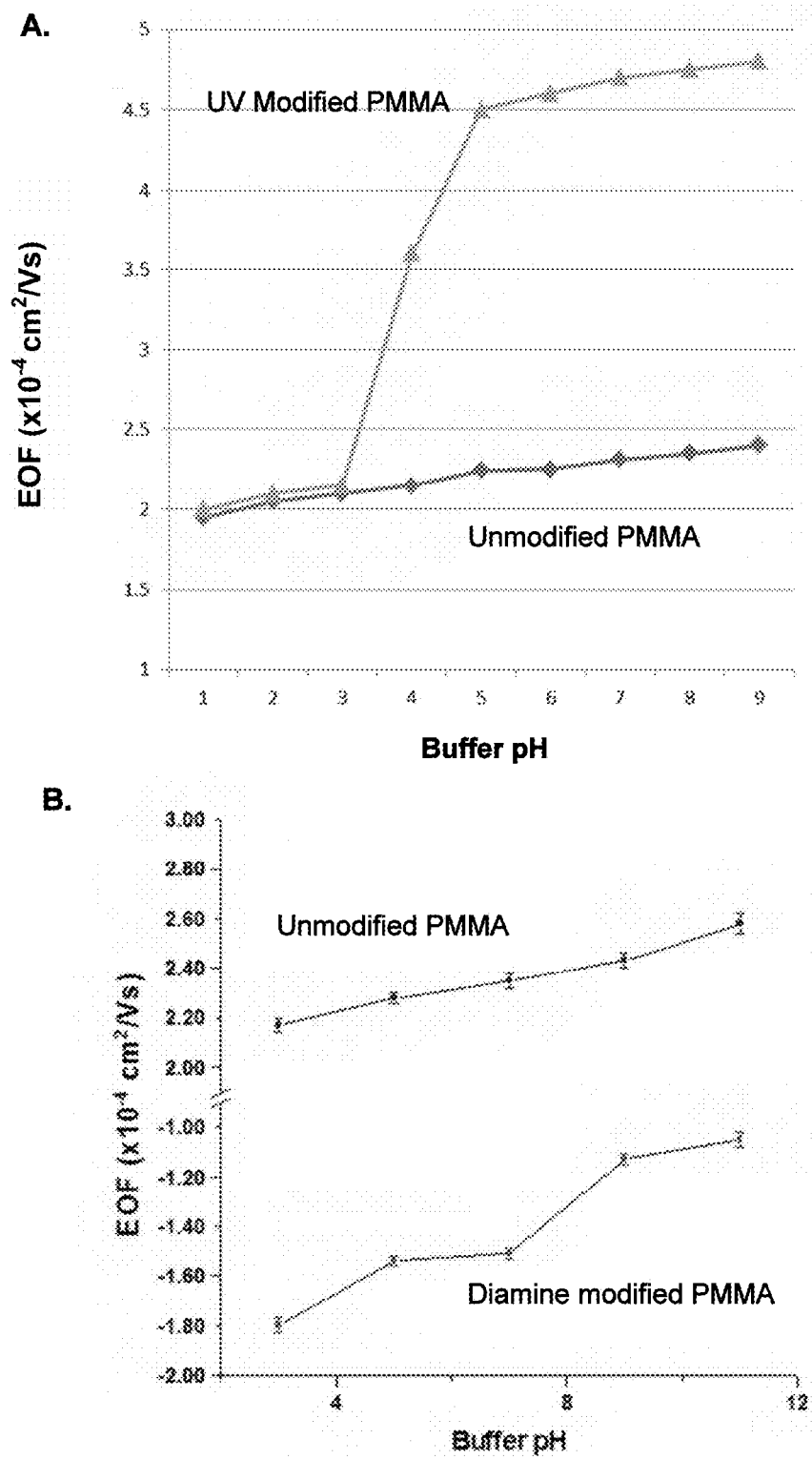
FIGS. 50A-50B show the effect of thermoplastic (PMMA) surface treatment on electoosmotic flow (EOF).

For the native PMMA nanochannel (FIG. 50A), the EOF moved in the direction of the cathode at all pH values. As can be seen, the EOF was fairly independent of solution pH, consistent with previous results for microchannels. However, when the PMMA nanochannel was treated with an O$_2$ plasma, the EOF became substantially higher at a pH>3. This significant EOF increase can be attributed to deprotonation of surface confined carboxylic acids, because the O$_2$ plasma induces oxidation of the PMMA surface creating surface confined carboxylic acid groups. When these groups become deprotonated, the surface charge density increases resulting in significant changes in the EOF. Therefore, the surface charge density on polymer nanochannels can be modified using O$_2$ plasma treatment. When the PMMA nanochannel is plasma oxidized followed by treatment with ethylene diamine (EDA) in the presence of EDC/NHS coupling reagents (FIG. 50B), one of the amine groups of EDA is covalently anchored to the pendant carboxylic acid groups generated on the PMMA nanochannel surface. This modification results in a reversal of the EOF (travels from cathode to anode) indicating a surface charge that is positive, compared to negative for the EOF running from anode to cathode. The trends observed in this data are similar to what has previously been observed in PMMA microchannels.

Example 11—Evaluating SME Using Polymer Nanocolumns: Tracking Fluorescently Labeled dNMPs Nanochannels were prepared as described above. In this case, however, the channels were fabricated in cyclic olefin copolymer (COC) using thermal NIL. The nanochannels were 100 nm×100 nm with a length of 100 μm. The channels were treated with an O$_2$ plasma as well as the cover plate, also made from COC, and the device was thermally assembled at a temperature of 78° C., which is slightly below the glass transition temperature of the native thermoplastic. For these experiments, single molecules were tracked using dark field microscopy. The molecules consisted of single silver (Ag) nanoparticles (NP) that were 10 nm in diameter and were coated with citrate ions, which imparts a negative charge on the Ag-NP. The Ag-NPs were placed in the cathodic reservoir and electrophoresed at different electric field strengths into the anodic reservoir. The electrophoresis was performed in a TBE buffer (1×, pH=8.0) that was also loaded with 10 mM KCl to reduce the thickness of the electrical double layer in the nanochannel.

Figure 51A:
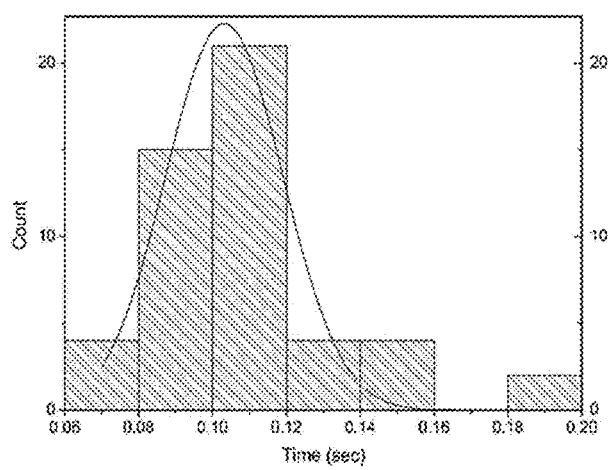
FIGS. 51A-51C demonstrate single entity electrophoretic mobility through PMMA nanochannels.
Figure 51B:
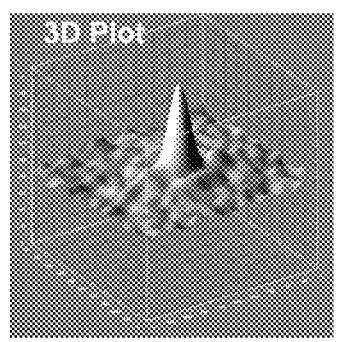
Figure 51C:
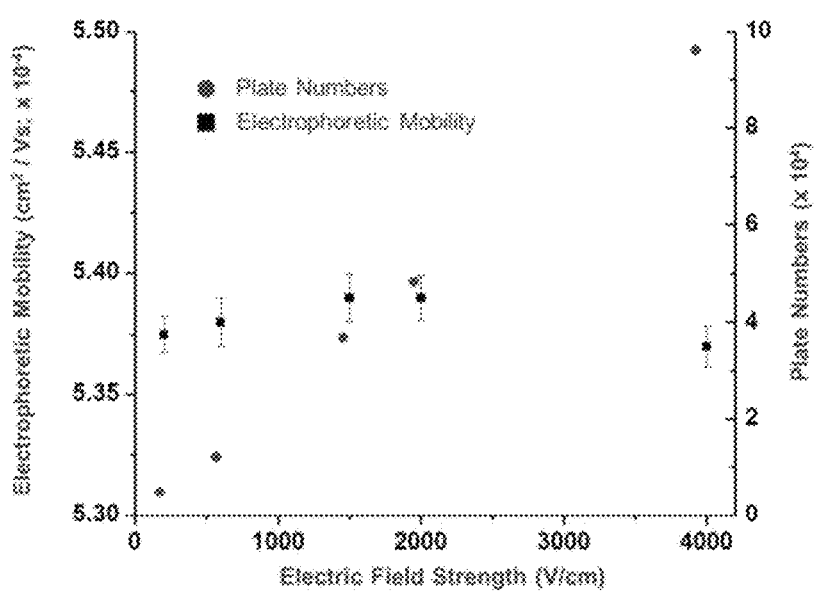

FIG. 51B is an image (3D-plot) of a single Ag-NP showing high intensity for the particle when placed (stationary) in the polymer nanochannel. The single molecules were electrophoresed through the polymer nanochannel at different electric field strengths and their motion was optically tracked. Translocation times were histogrammed to determine the variance in the measured flight times as a function of the electric field strengths. The smallest variance was noted for the highest electric field strength (4000 V/cm) as shown in FIG. 51A. As can be seen from FIG. 51C, the electrophoretic mobility of the Ag-NP (10 nm) was independent of the applied electric field, but the plate numbers, which inversely relate to the variance in the flight time distribution, increased with higher electric field strengths. This is in line with the fact that the variance is primarily arising from longitudinal diffusion and not any other artifact associated with the translocation events, because the diffusional spreading is proportional to the $(2Dt)^{1/2}$, where D is the Ag-NP diffusion coefficient and t is time. Higher electric field strengths result in shorter translocation times and thus, smaller diffusional spreading times.

Example 12—Longitudinal Current Blockage Events for T4 DNA and λDNA

PMMA nanofluidic device fabrication was carried out as described supra. Optical measurements of DNA translocation events through the device were made using an inverted microscope (Zeiss Axiovert 200). The fluorescence microscope was fitted with an EMCCD camera (iXon3 888 Andor). Two Faraday Cages were used for shielding the fluidic chip for electrical measurements, one was used to shield the sample stage, and the other covered the entire microscope. Video images were recorded and processed by MetaMorph (Molecular Devices). Overlap mode of the EMCCD was used during video recording with shutter time ranging from 5 ms to 20 ms.

Current measurements were performed using the whole cell mode of an Axopatch 200B amplifier and Digidata 1440A (Molecule Devices). Data acquisition and analysis was performed using the pCLAMP 10 software. Signals were sampled at a rate of 100 kHz with internal low-pass Bessel filter set at 10 kHz. Ag/AgCl wires were used as electrodes. For all the measurements, DNA was driven under 1 V applied by the patch clamp.

T4 DNA solutions (0.5 μg/ml) were prepared in 1×TBE buffer (89 mM tris-borate and 2 mM EDTA, pH 8.3). DNA was stained with YOYO®-1 in a 20:1 ratio (bp/dye). β-mercaptoethanol (3%) was added as an anti-photobleaching agent and an enzymatic oxygen scavenger system consisting of 0.2 mg/ml glucose oxidase, 0.04 mg/mL catalase, and 4 mg/ml (3-D-glucose was also added to the buffer to remove oxygen. A vacuum pump was used to initially wet the channels and to introduce the DNA solution into the device.

Figures 52A, 52B, 52C, 52D, 52E, 52F, 52G, 52H, 52I:
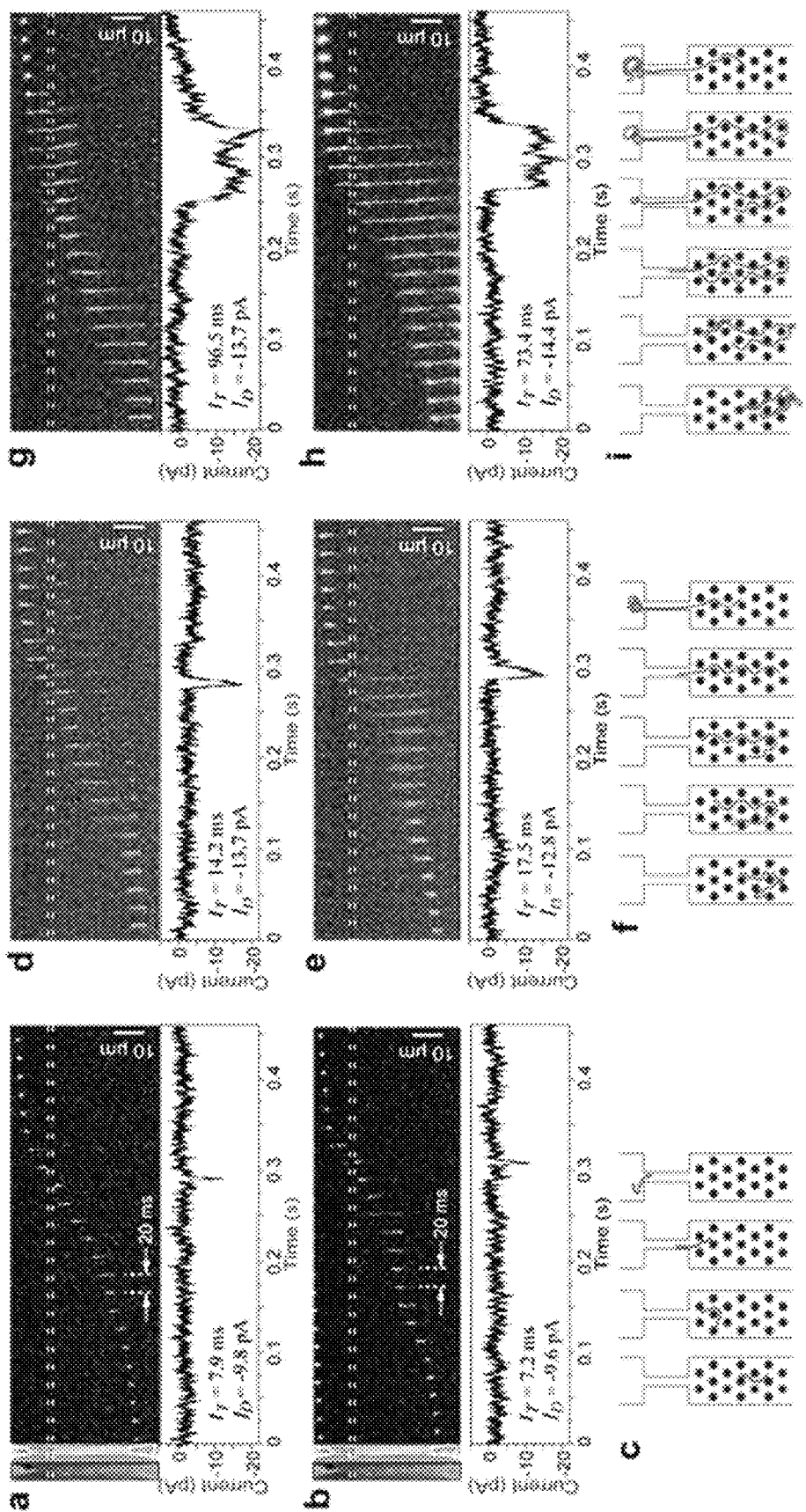
FIGS. 52A-52I depict optical and electrical measurements of T4 DNA translocation events through PMMA nanochannels.

FIGS. 52A-H are optical and electrical depictions of DNA translocation events for T4 DNA, moving electrically through PMMA nanochannels. These translocation events generated current responses, with the spikes occurring exactly when the DNA translocated through the nanochannel as observed optically. At the start of the translocation event, the DNA molecule moved slowly in the microchannel due to the low electric field strength. When the DNA molecule threaded into the nanopillar array, which was placed at the input end to the nanochannel, the molecule elongated by colliding with and hooking with the nanopillars. Once reaching the nanochannel, the DNA passed rapidly through the nanochannel due to the strong electric field, which was concentrated inside nanochannel due to its high resistance. After leaving the nanochannel, the DNA molecule slowed down and recoiled quickly. Among these translocation processes, only the process of DNA passing through the nanochannel generated ionic current drops. From the ionic current drops at the moment of DNA entering the nanochannel, it took 1-3 ms for the current to drop from the baseline to the bottom of the spike. The ionic current persisted with a current drop of ~15 pA with a time that was proportional to the length of the DNA molecule. To transfer the entire T4 DNA chain through the nanochannel took 2~3 frames (40~60 ms) as is shown in the fluorescence images. The time matched the reading from the I-t curve, where the width of the spike was 52 ms for intact T4 DNA molecules (FIGS. 52G and 52H).

Here $t_T$ stands for the duration of the current drop spike (DNA translocation time), $I_D$ stands for the amplitude of the current drop. FIGS. 52A-52C show ionic current spikes generated by translocation of short DNA molecules. Those small DNA segments were usually generated from damage of T4 DNA by photonicking under fluorescent excitation light or the shearing force during sample preparation. The lengths of these DNA segments, measured from the fluorescence image, were usually less than 5 μm. Faster electrophoretic mobility and small length allowed those DNA to translocate through nanochannel within a short time; $t_T$=5-10 ms and $I_D$ varied from 5-10 pA.

FIGS. 52D-52F show longer DNAs translocating through the nanochannel. Those DNA passed in 20~60 ms and $I_D$ was around 15 pA. They were assumed to be nicked DNA molecules, but did not correspond to full length T4 DNA molecules. Full length T4 DNA molecules translocating through the nanochannel are shown in FIGS. 52G-52I. Here, the time duration of the current transients was more in line with full length T4 DNA molecules.

This data indicates that DNA molecules can be detected exclusively with electrical measurements, and that the length of the DNA correlates to the length of the current transients generated. In these measurements, the current transients were deduced from longitudinal measurements, in which no nanoelectrodes were used, but instead, microelectrodes placed at the anodic and cathodic reservoirs of the device. These longitudinal current measurements can be made during an electrically driven translocation event. From these measurements, the duration of the transient can be correlated to DNA length. While optical measurements were made in these cases, they are not necessary for the electrical transduction. The optical measurements were made only to substantiate the nature of the electrical measurement.

Example 13—Creation of Nanogaps in Layered Nanowires Using Electrochemistry

A two-step methodology was developed to create nanogaps in segmented nanowires. These steps include (1) electrodepositing multisegmented nanowires, and (2) electrochemically etch a gap from an embedded sacrificial layer. As a demonstration of the electrodeposition technique, a nanoporous, polycarbonate template (Whatman, ~$10^8$ nanopores/cm² with a stated pore diameter of 100 nm) was used as the cathode in a two electrode cell. To create a conductive electrode one side of the polycarbonate template was sputtered with gold. The anode was a platinum mesh. Five nanowire segments were fabricated in the following sequential order: FeNiCo/Au/Cu/Au/FeNiCo. The FeNiCo nanowire segments were at the top and bottom of the nanowires, and served as a way to magnetically manipulate the resulting nanowires. The FeNiCo was an Fe-rich alloy (~64 wt % Fe, 31 wt % Ni, 5 wt % Co) deposited from an electrolyte containing: 0.72 M nickel sulfamate, 0.155 M ferrous sulfate, 0.005 M cobalt sulfate, 0.5 M boric acid, 0.001 M sodium lauryl sulfate, 0.011 M ascorbic acid, at a pH of 2 and temperature of 40° C., using a pulse deposition of −25 mA/cm² (20% porosity), duty cycle of 0.5, and on/off times of 2 seconds. Gold segments were fabricated at a current density of −1 mA/cm² at temperature of 60° C. by using a commercial gold solution (TG-25E RTU, Technic Inc.). A copper middle layer was deposited galvanostatically at −3 mA/cm². The copper electrolyte contained 0.15 M copper sulfate, 0.01 M sodium sulfate, 0.45 M sodium citrate, and 0.40 M boric acid. After deposition, the membrane was dissolved in dichloromethane and then washed with ethanol three times. The copper served as the sacrificial layer and the time of deposition was proportional to the gap size. In the second step, dissolution of the copper layer was controlled electrochemically by etching the nanowires placed on a conductive carbon surface. The applied working potential was +0.1 V vs SCE, and the solution was the same citrate-boric acid electrolyte as used for copper plating.

Figures 53A, 53B:
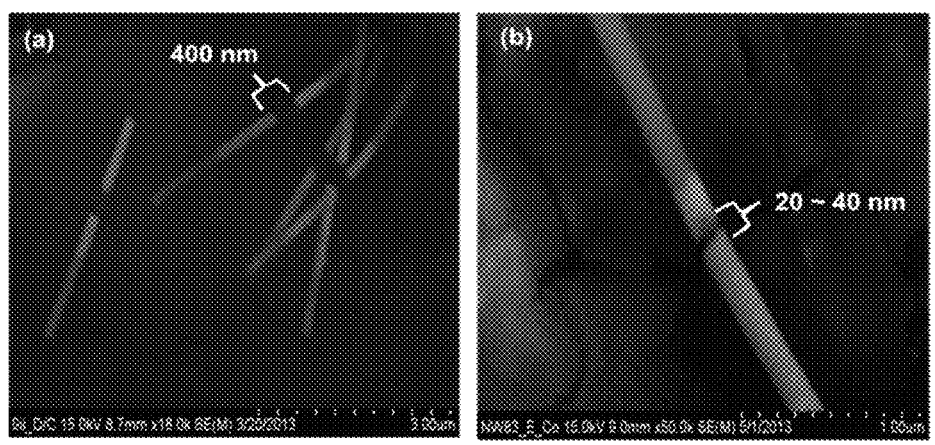
FIGS. 53A-53B are images of segmented nanowires containing nanogaps that were produced by electrochemical etching.

The procedure was successful in creating nanowires with gaps that can be controlled at different dimensions (see FIGS. 53A-53B). A critical feature is that during etching the FeNiCo and Au regions are not attacked, based on the selection of the applied potential. The Au is not dissolved because it is more noble than copper, and the FeNiCo is not attacked because the potential and electrolyte is selected to create a passive film onto its surface in a core-shell type of configuration. Thick, large diameter nanowires were used to develop the technique and will be extended to smaller diameter wires. To create more discrete gaps and thinner gap sizes the deposition of the copper layer is being examined with a pulse and pulse-reverse plating scheme.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A device comprising:
   a biomolecular processor, each biomolecular processor comprising:
   one or more bioreactor chambers defined by a solid substrate;
   a support structure within each bioreactor chamber and attached to the solid substrate;
   a cleaving enzyme immobilized to the support structure and operatively positioned within said bioreactor chamber to cleave monomer or multimer units of a biopolymer molecule operatively engaged by said cleaving enzyme; and
   one or more time-of-flight channels formed in the solid substrate and fluidically coupled to said one or more bioreactor chambers, each of said one or more time-of-flight channels having an input end and an output end, wherein each of said one or more time-of-flight channels comprise two or more sensors including at least (i) a first sensor contacting each of the one or more time-of-flight channels proximate to the input end of the time-of-flight channel and forming a first nanogap within the time-of-flight channel, wherein said nanogap has a width that is less than the width of the time-of-flight channel, and (ii) a second sensor contacting each of the one or more time-of-flight channels proximate to the output end of the time-of-flight channel and forming a second nanogap within the time-of-flight channel, wherein said second nanogap has a width that is less than the width of the time-of-flight channel.

2. The device of claim 1 further comprising:
   an electric field generator operatively positioned to create an electric field in said one or more bioreactor chambers and along the length of said one or more time-of-flight channels.

3. The device of claim 1, wherein said one or more time-of-flight channels is less than or equal to 50 nm wide and less than or equal to 50 nm deep.

4. The device of claim 1, wherein the first nanogap within the time-of-flight channel is about 1 nm to about 10 nm wide.

5. The device of claim 1, wherein the second nanogap within the time-of-flight channel is about 1 nm to about 10 nm wide.

6. The device of claim 1, wherein said one or more time-of-flight channels is 5 µm-250 µm long.

7. The device of claim 1, wherein said one or more bioreactor chambers is 100 nm-1000 nm wide.

8. The device of claim 1, wherein the support structure within the one or more bioreactor chambers is 50 nm-900 nm wide.

9. The device of claim 1, wherein the solid substrate is a made of a polymeric material.

10. The device of claim 1, wherein the cleaving enzyme is an exonuclease or exoribonuclease.

11. The device of claim 1, wherein the cleaving enzyme is a protease.

12. The device of claim 1, wherein the one or more time-of-flight channels comprise three or more sensors.

13. The device of claim 1, wherein the biomolecular processor further comprises:
a feeder channel defined by walls of said solid substrate, said feeder channel having a length extending from an input end proximate to a surface of the solid substrate to an output end proximate to said one or more bioreactor chambers.

14. The device of claim 1 further comprising:
a sensor contacting said feeder channel proximate to the input end of the feeder channel.

15. The device of claim 14, wherein the feeder channel sensor forms a nanogap within the feeder channel, wherein said nanogap has a width that is less than the width of the feeder channel.

16. The device of claim 13, wherein the feeder channel comprises one or more entropic traps between the input and output ends.

17. The device of claim 13, wherein the feeder channel is less than or equal to 100 nm wide and less than or equal to 100 nm deep.

18. The device of claim 1, wherein one or more the time-of-flight channels comprise a charge neutral hydrophilic wall surface, a charged hydrophilic wall surface, or a charge neutral hydrophobic wall surface.

19. The device of claim 1, wherein the device comprises 10,000 or more biomolecular processors.

20. The device of claim 1, wherein the device comprises 100,000 or more biomolecular processors.

21. A method for nucleic acid molecule sequencing comprising:
providing the device of claim 1;
feeding a sample comprising one or more nucleic acid molecules into said biomolecular processor of said device under conditions effective for the immobilized cleaving enzyme within the bioreactor chamber to engage the one or more nucleic acid molecules in the sample and to cleave the one or more nucleic acid molecules into monomer nucleotides that individually enter the input end of the one or more time-of-flight channels;
applying an electric field across the one or more bioreactor chambers and along the length of the one or more time-of-flight channels to transport the cleaved monomer nucleotides through the one or more time-of-flight channels;
detecting, based on said applying, the cleaved monomer nucleotides as they pass at least the first and second sensors in the one or more time-of-flight channels;
measuring, based on said detecting, how long it takes for each cleaved monomer nucleotide to pass at least the first and second sensors in the one or more time-of-flight channels; and
identifying the monomer nucleotides based on said measuring.

22. The method of claim 21, wherein said measuring further comprises:
measuring electrical peak amplitude of each cleaved monomer nucleotide as it passes at least one of the first or second sensors in the one or more time-of-flight channels.

23. A method for identifying one or more proteins or polypeptides comprising:
providing the device of claim 1;
feeding a sample comprising one or more proteins or polypeptides into the biomolecular processor of the device under conditions effective for the immobilized cleaving enzyme within the bioreactor chamber to engage the one or more proteins or polypeptides in the sample and to cleave the one or more proteins or polypeptides into smaller peptide fragments that enter the input end of the one or more time-of-flight channels;
applying an electric field across the one or more bioreactor chambers and along the length of the one or more time-of-flight channels to transport the cleaved peptide fragments through the one or more time-of-flight channels;
detecting, based on said applying, the peptide fragments as they pass at least the first and second sensors in the one or more time-of-flight channels;
measuring, based on said detecting, (i) how long it takes for each peptide fragment to pass at least the first and second sensors of the one or more time-of-flight channels, and/or (ii) electrical peak amplitude of each peptide fragment as it passes at least one of the first or second sensors in the one or more time-of-flight channels; and
identifying at least a portion of the one or more proteins or polypeptides in the sample based on said measuring of the peptide fragments.

* * * * *

SEQUENCE LISTING

```
<160> NUMBER OF SEQ ID NOS: 6

<210> SEQ ID NO 1
<211> LENGTH: 36
<212> TYPE: DNA
<213> ORGANISM: Artificial
<220> FEATURE:
<223> OTHER INFORMATION: Oligonucleotide Adapter
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(20)
<223> OTHER INFORMATION: n is a, c, g, or t
<220> FEATURE:
<221> NAME/KEY: misc_feature
<222> LOCATION: (27)..(30)
<223> OTHER INFORMATION: n is a, c, g, or t

<400> SEQUENCE: 1
cgntngnanc nnnnnnnnnn ccgagcnnnn gctcgg                                  36

<210> SEQ ID NO 2
<211> LENGTH: 11
<212> TYPE: DNA
<213> ORGANISM: Artificial
<220> FEATURE:
<223> OTHER INFORMATION: Oligonucleotide Adapter
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
```

```
<222> LOCATION: (8)..(8)
<223> OTHER INFORMATION: n is a, c, g, or t

<400> SEQUENCE: 2
gntncnancg t                                                               11

<210> SEQ ID NO 3
<211> LENGTH: 38
<212> TYPE: DNA
<213> ORGANISM: Artificial
<220> FEATURE:
<223> OTHER INFORMATION: Oligonucleotide Adapter
<220> FEATURE:
<221> NAME/KEY: misc_feature
<222> LOCATION: (3)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (29)..(32)
<223> OTHER INFORMATION: n is a, c, g, or t

<400> SEQUENCE: 3
ggnnnnnnnn nncgntngna ncccgagcnn nngctcgg                                  38

<210> SEQ ID NO 4
<211> LENGTH: 13
<212> TYPE: DNA
<213> ORGANISM: Artificial
<220> FEATURE:
<223> OTHER INFORMATION: Oligonucleotide Adapter
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 4
tttgntncna ncg                                                             13

<210> SEQ ID NO 5
<211> LENGTH: 25
<212> TYPE: DNA
<213> ORGANISM: Artificial
<220> FEATURE:
<223> OTHER INFORMATION: Oligonucleotide Adapter
<220> FEATURE:
```

```
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(23)
<223> OTHER INFORMATION: n is a, c, g, or t

<400> SEQUENCE: 5
tttgntncna ncgnnnnnnn nnncc                                         25

<210> SEQ ID NO 6
<211> LENGTH: 26
<212> TYPE: DNA
<213> ORGANISM: Artificial
<220> FEATURE:
<223> OTHER INFORMATION: Oligonucleotide Adapter
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (14)..(23)
<223> OTHER INFORMATION: n is a, c, g, or t

<400> SEQUENCE: 6
tttgntncna ncgnnnnnnn nnncca                                        26
```